US012558494B2

(12) United States Patent　　　(10) Patent No.:　US 12,558,494 B2
Mayle, Jr. et al.　　　　　　　　(45) **Date of Patent:　\*Feb. 24, 2026**

(54) INJECTION DEVICE

(71) Applicant: VELOJECT, LLC, San Francisco, CA (US)

(72) Inventors: Robert E. Mayle, Jr., Kentfield, CA (US); Erik J. Shahoian, Sonoma, CA (US); Terrence C. Smith, Portland, OR (US); Alexander Jasso, Portland, OR (US)

(73) Assignee: VELOJECT, LLC, San Francisco, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 18/175,470

(22) Filed: Feb. 27, 2023

(65) Prior Publication Data

US 2023/0211091 A1　　Jul. 6, 2023

Related U.S. Application Data

(63) Continuation of application No. 17/575,604, filed on Jan. 13, 2022, now Pat. No. 11,590,292, which is a continuation of application No. 17/223,976, filed on Apr. 6, 2021, now Pat. No. 11,229,750.

(60) Provisional application No. 63/006,056, filed on Apr. 6, 2020.

(51) Int. Cl.
　*A61M 5/315*　　(2006.01)
　*A61M 39/24*　　(2006.01)

(52) U.S. Cl.
　CPC ........ *A61M 5/31596* (2013.01); *A61M 39/24* (2013.01); *A61M 2205/18* (2013.01); *A61M 2205/3331* (2013.01); *A61M 2205/8206* (2013.01)

(58) Field of Classification Search
　CPC ............ A61M 5/31596; A61M 5/1422; A61M 5/14216; A61M 5/19; A61M 39/24; A61M 2205/18; A61M 2205/3331; A61M 2205/8206; F04B 1/02
　See application file for complete search history.

(56) References Cited

U.S. PATENT DOCUMENTS

| | | | |
|---|---|---|---|
| 3,597,113 | A | 8/1971 | Dumoulin |
| 5,076,769 | A | 12/1991 | Shao |
| 5,232,024 | A | 8/1993 | Williams |

(Continued)

FOREIGN PATENT DOCUMENTS

| | | |
|---|---|---|
| JP | H06142199 A | 5/1994 |
| WO | WO88/003815 A1 | 6/1988 |

(Continued)

*Primary Examiner* — James D Ponton
*Assistant Examiner* — John A Doubrava
(74) *Attorney, Agent, or Firm* — Shay Glenn LLP

(57)　　　ABSTRACT

Apparatuses and methods for delivering a fluid, including a viscous fluid. These apparatuses may include a fluid reservoir, two or more piston chambers, a manifold, a delivery port, and a drive assembly and may be configured to inject either a predetermined amount of fluid or a continuous stream of fluid. These apparatuses may also be configured to switch between filling, injection and aspiration modes. These apparatuses may generally be hand-held and lightweight and may provide a significant mechanical advantage to the user.

20 Claims, 44 Drawing Sheets

(56)            References Cited

U.S. PATENT DOCUMENTS

| | | | |
|---|---|---|---|
| 5,492,535 | A * | 2/1996 | Reed .................. A61M 60/113 |
| | | | 604/152 |
| 5,755,224 | A | 5/1998 | Good et al. |
| 5,916,197 | A | 6/1999 | Reilly et al. |
| 5,921,951 | A | 7/1999 | Morris |
| 6,022,329 | A | 2/2000 | Amett et al. |
| 6,428,518 | B1 | 8/2002 | Brengle et al. |
| 7,638,958 | B2 | 12/2009 | Philipp et al. |
| 8,382,703 | B1 | 2/2013 | Abdelaal |
| 9,770,551 | B1 | 9/2017 | Faden |
| 10,463,791 | B2 | 11/2019 | Shergold et al. |
| 11,229,750 | B2 | 1/2022 | Mayle et al. |
| 11,565,055 | B2 * | 1/2023 | Mayle, Jr. ............. A61M 39/24 |
| 11,590,292 | B2 * | 2/2023 | Mayle, Jr. ........... A61M 5/1422 |
| 2006/0292304 | A1 | 12/2006 | Tisone |
| 2008/0045925 | A1 * | 2/2008 | Stepovich ......... A61M 5/16827 |
| | | | 604/82 |
| 2008/0167621 | A1 | 7/2008 | Wagner et al. |
| 2009/0043441 | A1 | 2/2009 | Breed |
| 2010/0160900 | A1 | 6/2010 | Khoun et al. |
| 2010/0286650 | A1 | 11/2010 | Fitzgerald |
| 2011/0002802 | A1 | 1/2011 | Capone et al. |
| 2011/0196309 | A1 * | 8/2011 | Wells ................ A61M 5/14216 |
| | | | 604/173 |
| 2012/0053557 | A1 | 3/2012 | Abal |
| 2012/0244018 | A1 | 9/2012 | Reilly |
| 2012/0265128 | A1 | 10/2012 | Kolin |
| 2013/0053816 | A1 | 2/2013 | Diperna et al. |
| 2013/0150825 | A1 | 6/2013 | Rimsa et al. |
| 2014/0134001 | A1 | 5/2014 | Uchida et al. |
| 2014/0224829 | A1 | 8/2014 | Capone et al. |
| 2015/0029816 | A1 | 1/2015 | Beyer et al. |
| 2015/0032054 | A1 | 1/2015 | Eberhard |
| 2015/0157789 | A1 | 6/2015 | Capone et al. |
| 2015/0174321 | A1 | 6/2015 | Cohen |
| 2015/0182685 | A1 | 7/2015 | Henniges et al. |
| 2015/0320964 | A1 | 11/2015 | Guzman |
| 2015/0343137 | A1 | 12/2015 | Bonnette et al. |
| 2016/0235920 | A1 | 8/2016 | Finke et al. |
| 2016/0263319 | A1 * | 9/2016 | Brandeis ............... A61M 1/815 |
| 2017/0021951 | A1 | 1/2017 | Teague |
| 2017/0119953 | A1 | 5/2017 | Wen |
| 2017/0290987 | A1 | 10/2017 | Mandaroux et al. |
| 2017/0298929 | A1 | 10/2017 | Littich |
| 2018/0043088 | A1 | 2/2018 | Adams et al. |
| 2019/0117921 | A1 | 4/2019 | Bender et al. |
| 2019/0201615 | A1 | 7/2019 | You et al. |
| 2019/0247569 | A1 | 8/2019 | Dern et al. |
| 2019/0365993 | A1 | 12/2019 | Staub et al. |
| 2020/0129695 | A1 * | 4/2020 | Brandeis .......... A61M 5/31581 |
| 2024/0091457 | A1 | 3/2024 | Mayle et al. |

FOREIGN PATENT DOCUMENTS

| | | | |
|---|---|---|---|
| WO | WO2014/104338 | A1 | 7/2014 |
| WO | WO2018/203203 | A1 | 11/2018 |
| WO | WO2019/003220 | A1 | 1/2019 |

* cited by examiner

4

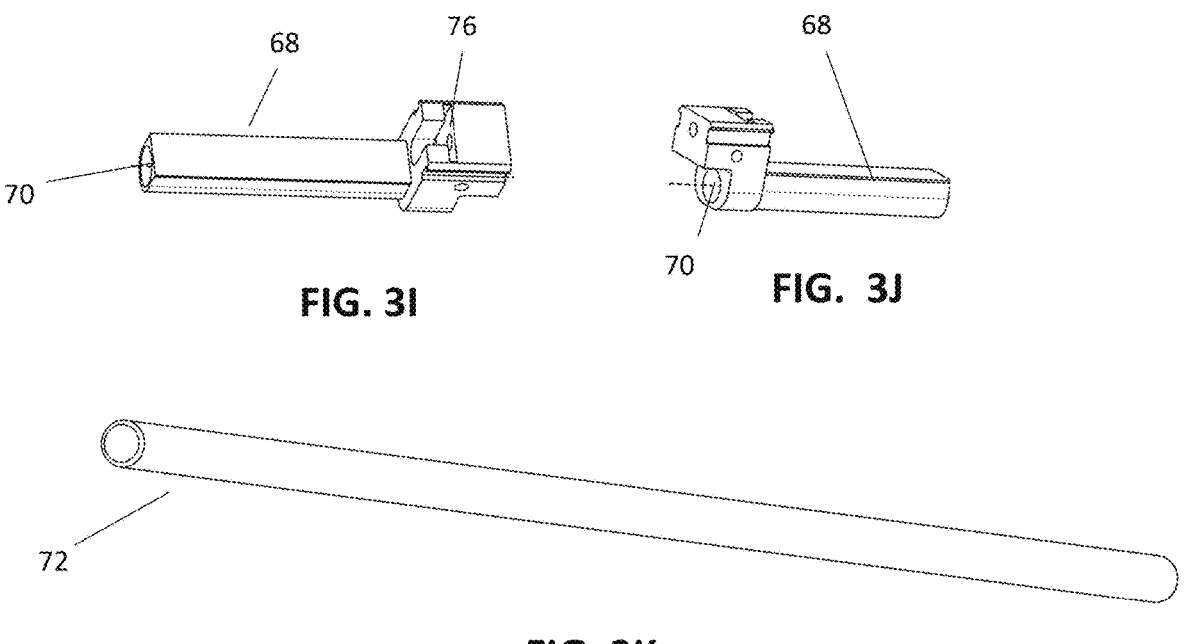
FIG. 3I          FIG. 3J
FIG. 3K
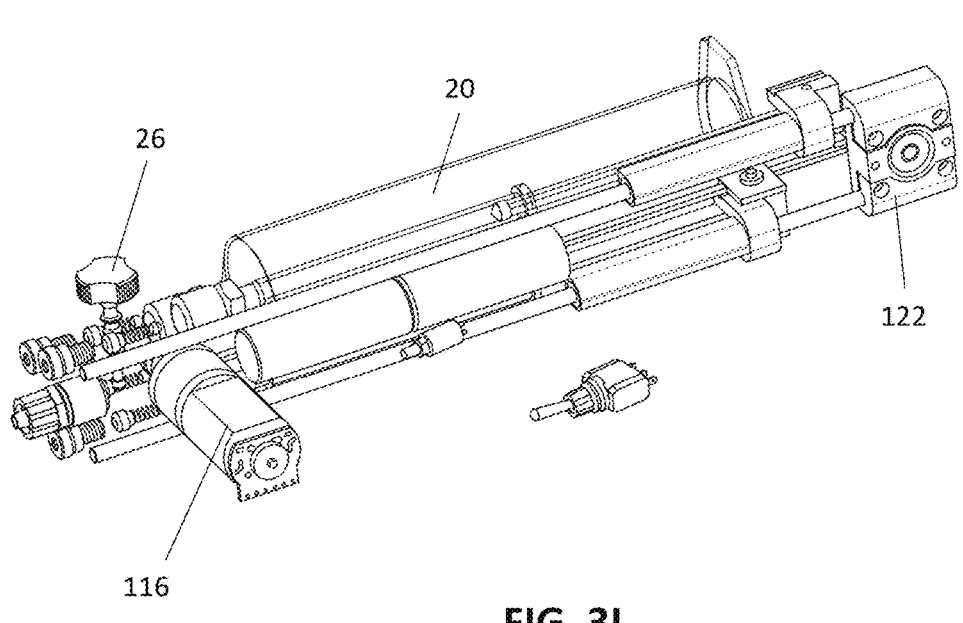
FIG. 3L

44

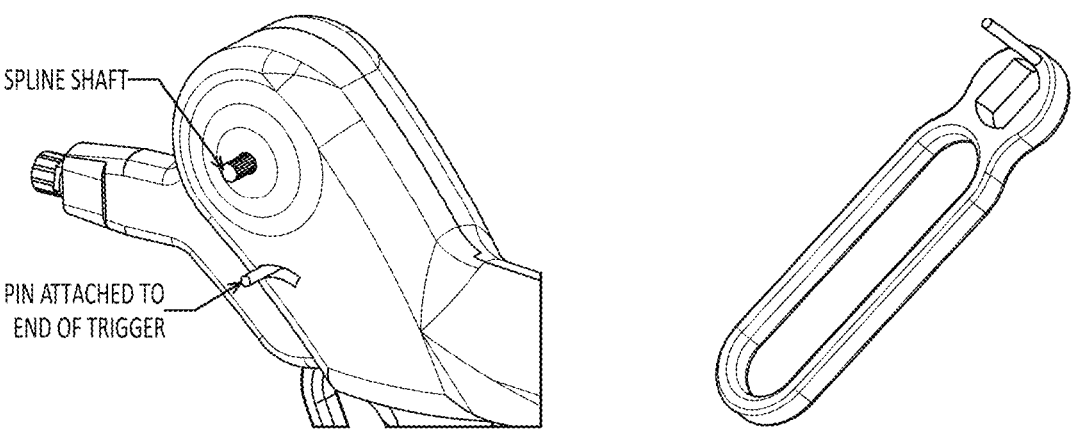
FIG. 5A                  FIG. 5B
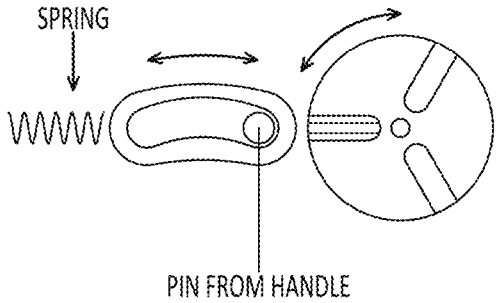
FIG. 6

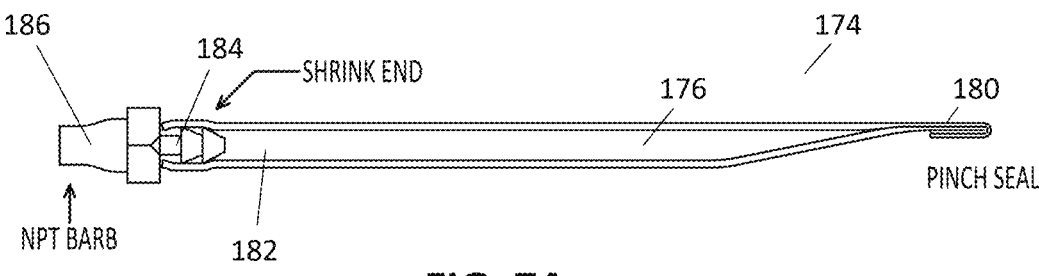
186
184 — SHRINK END
174
176
180
NPT BARB
182
PINCH SEAL
FIG. 7A
174
NPT BARB
— SPRING LOADED ROLLER
200
192
180
PINCH
204
FLUID
184
176
204 FLUID
TUBE
SHAFT
200
198
194
190
196
FIG. 7B
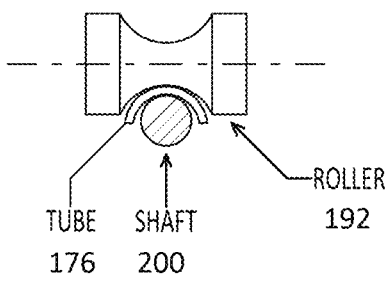
TUBE    SHAFT
— ROLLER
192
TUBE   SHAFT
176    200
FIG. 7C

'10' CLICKS = 10cc

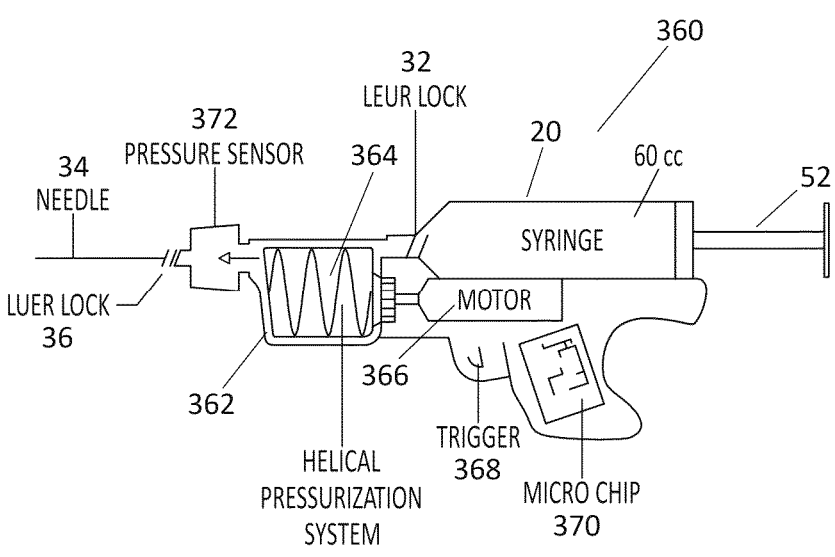

FIG. 14

(Optionally) set volume and/or pressure and/or flow rate for delivery of viscus fluid (e.g., by operating control(s) on hand-held injector
2101

Actuate a control on the hand-held injector to deliver a predetermined amount and/or flow rate of viscus fluid
2103

Reciprocally, until the predetermined amount is delivered (or all fluid has been injected): pressurize & eject, and refill a plurality of different delivery chambers, where the delivery chambers are refilled from a storage chamber of the viscus fluid. The device may switch between ejecting from pre-pressurized delivery chambers, and refill the one or more delivery chambers that are not currently ejecting during the ejection stage. Optionally, pressurizing may occur prior switching (pre-pressurizing).
2105

FIG. 15A

Figure 15B:
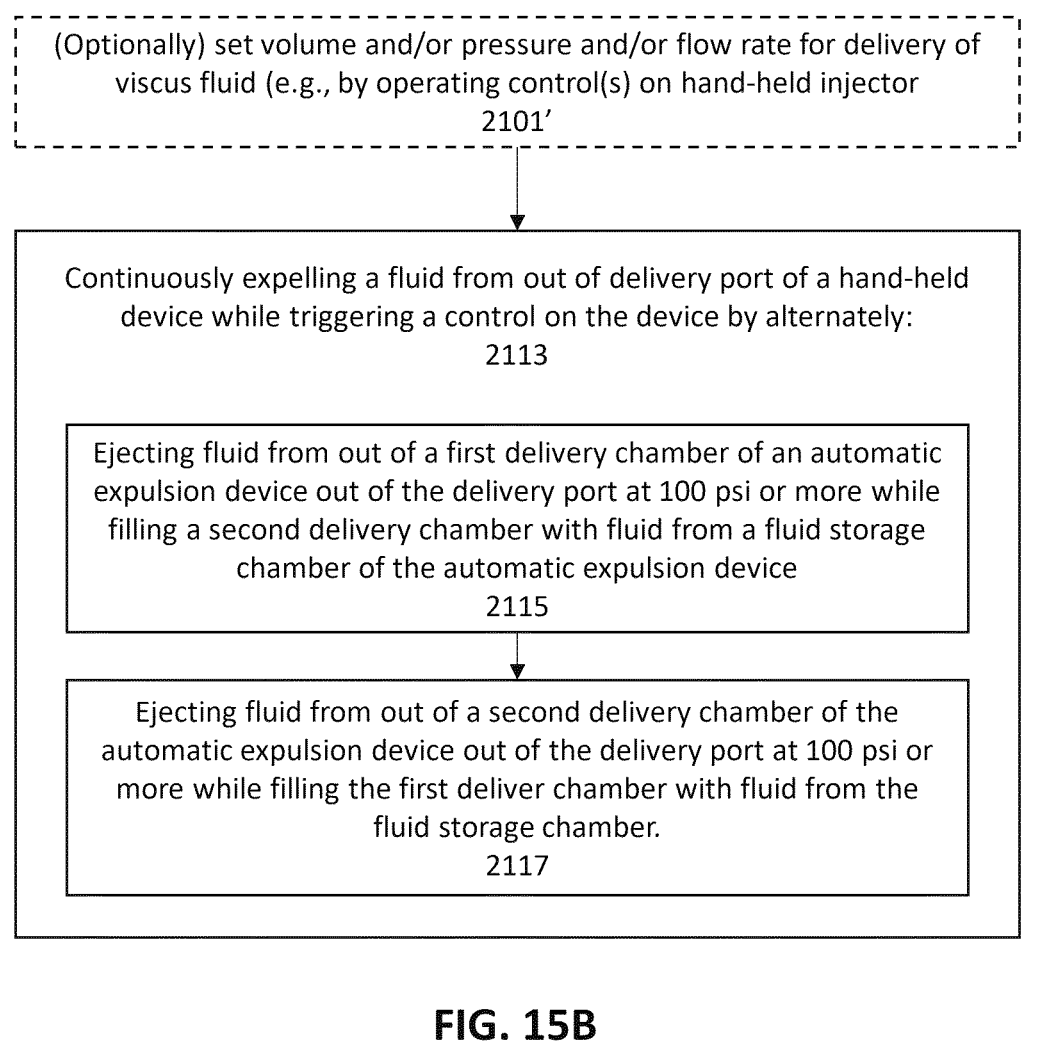

(Optionally) set volume and/or pressure and/or flow rate for delivery of viscus fluid (e.g., by operating control(s) on hand-held injector
2101'

Continuously expelling a fluid from out of delivery port of a hand-held device while triggering a control on the device by alternately:
2113

Ejecting fluid from out of a first delivery chamber of an automatic expulsion device out of the delivery port at 100 psi or more while filling a second delivery chamber with fluid from a fluid storage chamber of the automatic expulsion device
2115

Ejecting fluid from out of a second delivery chamber of the automatic expulsion device out of the delivery port at 100 psi or more while filling the first deliver chamber with fluid from the fluid storage chamber.
2117

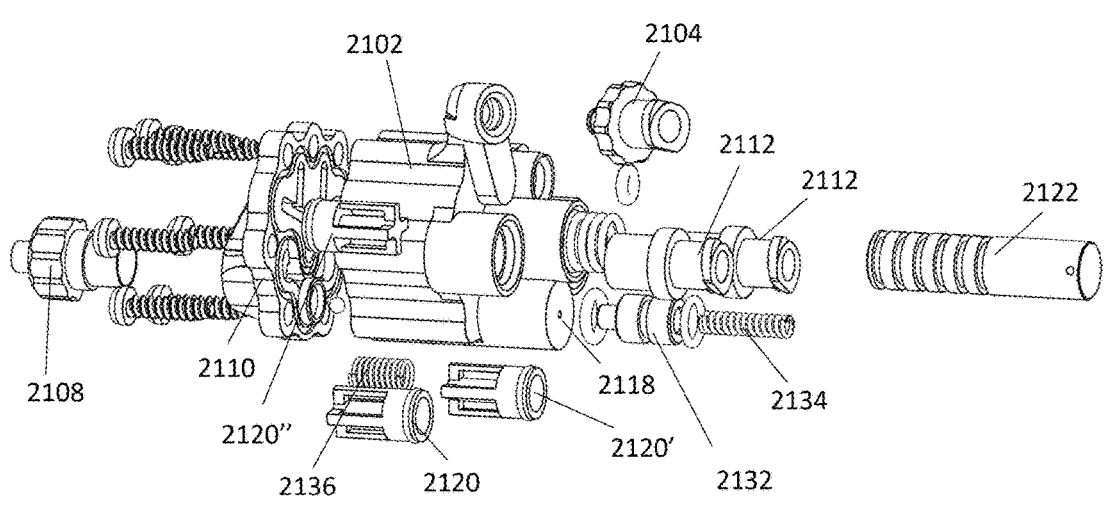
FIG. 21D
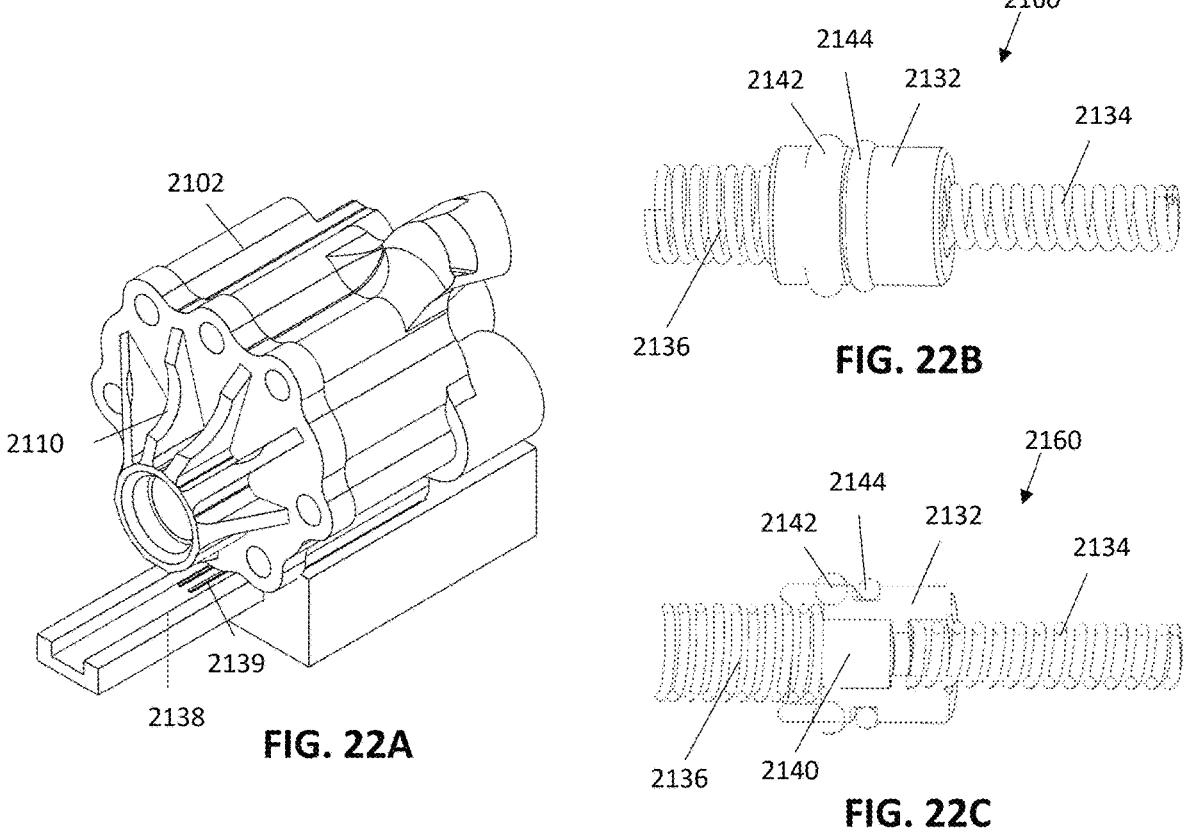
FIG. 22B
FIG. 22A
FIG. 22C

2700

2703

2703

2700          2703

2703

2709

2711

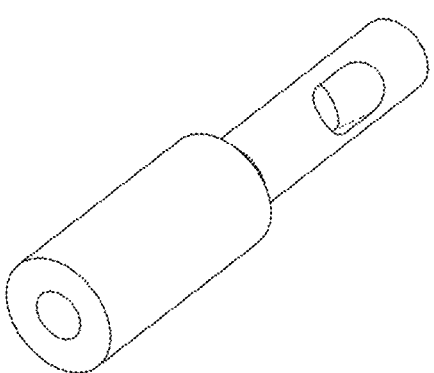
FIG. 31
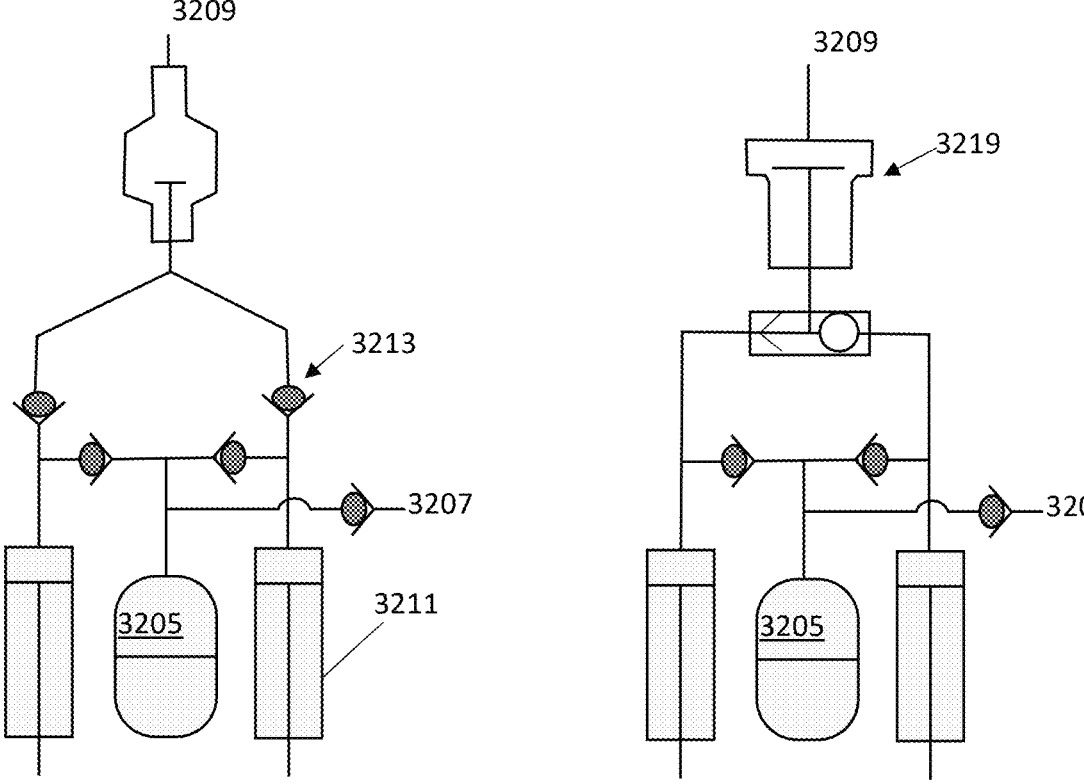
FIG. 32A          FIG. 32B

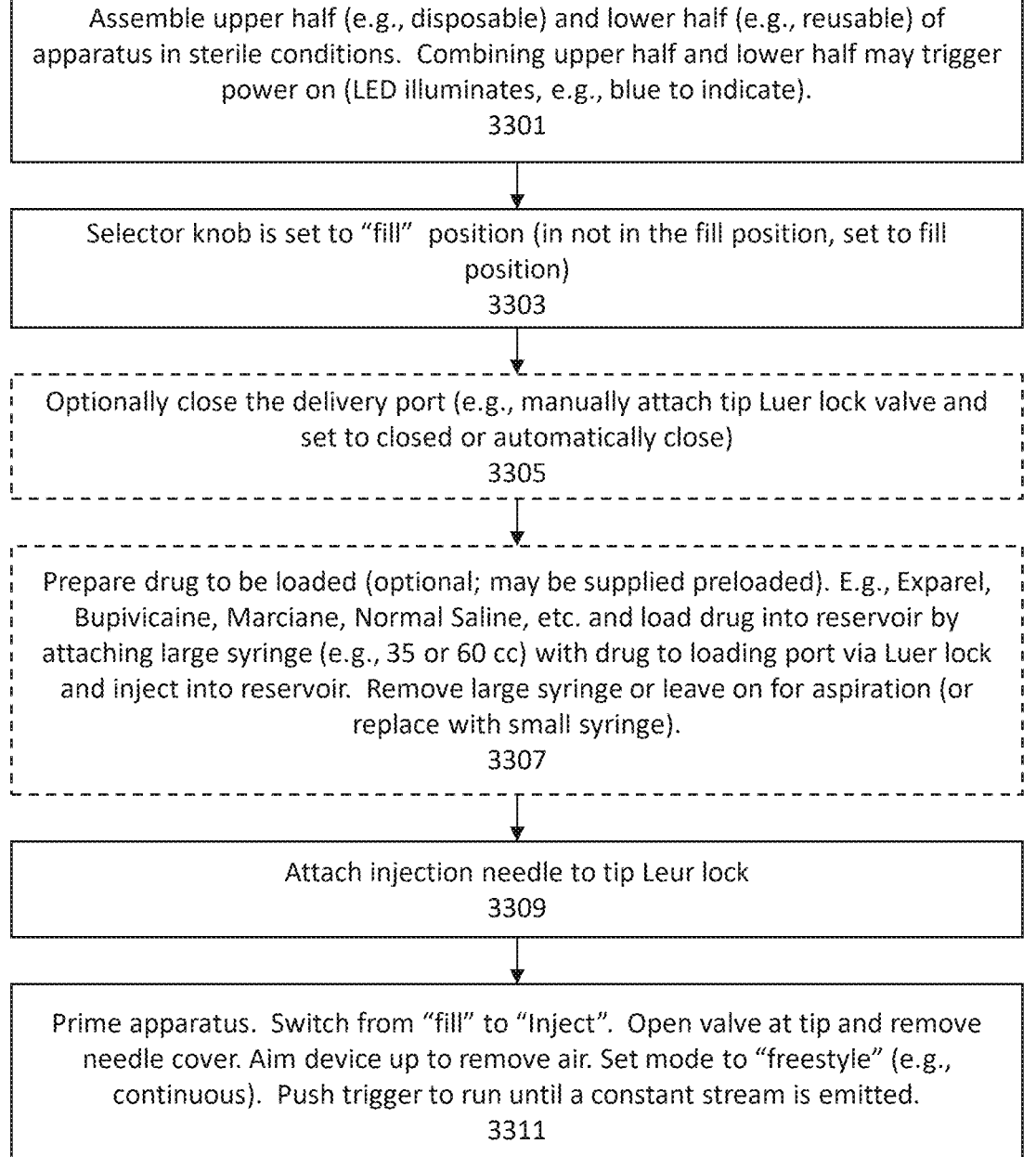

Assemble upper half (e.g., disposable) and lower half (e.g., reusable) of apparatus in sterile conditions. Combining upper half and lower half may trigger power on (LED illuminates, e.g., blue to indicate).
3301

Selector knob is set to "fill" position (in not in the fill position, set to fill position)
3303

Optionally close the delivery port (e.g., manually attach tip Luer lock valve and set to closed or automatically close)
3305

Prepare drug to be loaded (optional; may be supplied preloaded). E.g., Exparel, Bupivicaine, Marciane, Normal Saline, etc. and load drug into reservoir by attaching large syringe (e.g., 35 or 60 cc) with drug to loading port via Luer lock and inject into reservoir. Remove large syringe or leave on for aspiration (or replace with small syringe).
3307

Attach injection needle to tip Leur lock
3309

Prime apparatus. Switch from "fill" to "Inject". Open valve at tip and remove needle cover. Aim device up to remove air. Set mode to "freestyle" (e.g., continuous). Push trigger to run until a constant stream is emitted.
3311

FIG. 33

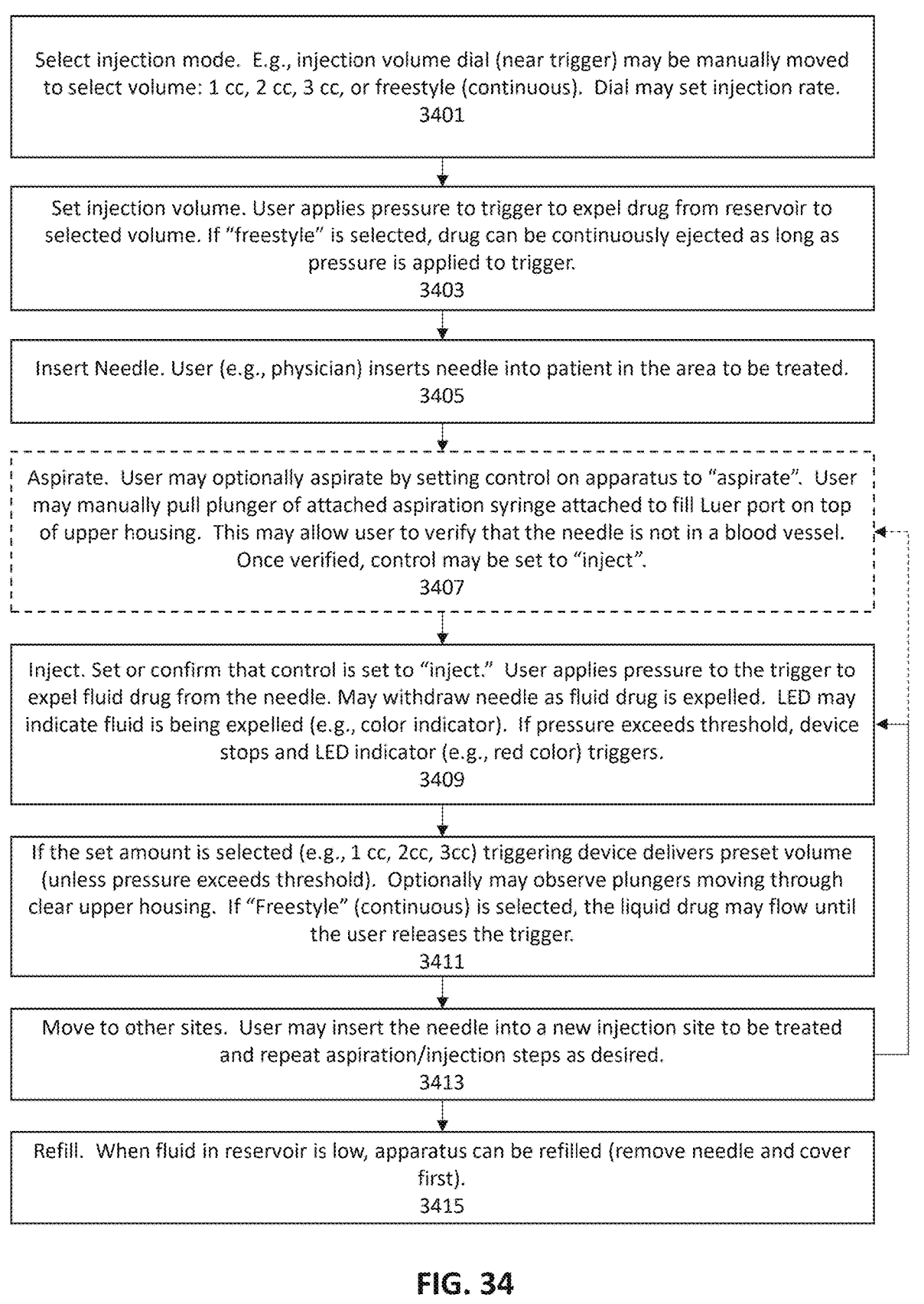

Select injection mode. E.g., injection volume dial (near trigger) may be manually moved to select volume: 1 cc, 2 cc, 3 cc, or freestyle (continuous). Dial may set injection rate.
3401

Set injection volume. User applies pressure to trigger to expel drug from reservoir to selected volume. If "freestyle" is selected, drug can be continuously ejected as long as pressure is applied to trigger.
3403

Insert Needle. User (e.g., physician) inserts needle into patient in the area to be treated.
3405

Aspirate. User may optionally aspirate by setting control on apparatus to "aspirate". User may manually pull plunger of attached aspiration syringe attached to fill Luer port on top of upper housing. This may allow user to verify that the needle is not in a blood vessel. Once verified, control may be set to "inject".
3407

Inject. Set or confirm that control is set to "inject." User applies pressure to the trigger to expel fluid drug from the needle. May withdraw needle as fluid drug is expelled. LED may indicate fluid is being expelled (e.g., color indicator). If pressure exceeds threshold, device stops and LED indicator (e.g., red color) triggers.
3409

If the set amount is selected (e.g., 1 cc, 2cc, 3cc) triggering device delivers preset volume (unless pressure exceeds threshold). Optionally may observe plungers moving through clear upper housing. If "Freestyle" (continuous) is selected, the liquid drug may flow until the user releases the trigger.
3411

Move to other sites. User may insert the needle into a new injection site to be treated and repeat aspiration/injection steps as desired.
3413

Refill. When fluid in reservoir is low, apparatus can be refilled (remove needle and cover first).
3415

FIG. 34

INJECTION DEVICE

CROSS REFERENCE TO RELATED APPLICATIONS

This patent application is a continuation of U.S. patent application Ser. No. 17/575,604, filed Jan. 13, 2022, titled "INJECTION DEVICE," now U.S. Pat. No. 11,590,292, which is a continuation of U.S. patent application Ser. No. 17/223,976, filed Apr. 6, 2021, titled "INJECTION DEVICE," now U.S. Pat. No. 11,229,750, which claims priority to U.S. Provisional Patent Application No. 63/006,056 filed Apr. 6, 2020, and titled "AUTOMATIC FLUID EXPULSION DEVICE," each of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is generally related to apparatuses and methods for delivering a fluid to a patient. More specifically, this disclosure relates to delivering a viscous fluid, such as a pharmaceutical drug or an injectable material, to a patient.

BACKGROUND

Every year, more than 600,000 knee replacements and more than 300,000 hip replacements are performed in the United States alone. Some 2.6 million people get facial cosmetic surgery. Pain medications for replacements and fillers for cosmetic surgery are delivered into multiple locations on a knee, hip or face, requiring a relatively large number of injections of significant volumes. Tissues in the knee, hip, and face, such as muscle, ligaments, and tendons, and other connective tissue are dense and fibrous and resist injection, at least in part because pain medications for replacements and fillers for cosmetic surgery are viscous. Viscous fluid typically does not flow well. Viscous fluids can be difficult to expel from a syringe (the current method for delivering these fluids. Expelling a viscous fluid or injecting a resistant tissue requires higher pressure; thus viscous solutions generally take more time to inject, and injecting large quantities of pain medications and fillers can be time-consuming. Expelling a viscous fluid from a syringe can be hard on the operator's hands, and in particular, expelling a large quantity of fluid from a syringe can be hard on the operator's hands. This difficulty may be compounded when injecting a fluid into resistant tissues.

Current methods of delivering viscous fluids using hand-held syringes suffers from these and other many drawbacks. Described herein are apparatuses and methods to deliver viscous fluids in a manner that may address these drawbacks and delivers pain medications, fillers, and other viscous fluids in a manner that is easy, safe, and fast for the benefit of both the patient and the operator providing the treatment.

SUMMARY OF THE DISCLOSURE

Described herein are methods and apparatuses (e.g., devices, systems, assemblies, etc.) for injecting fluid, and particularly viscus fluid, into a tissue. These apparatuses may be hand-held apparatuses that can deliver multiple doses of pre-set (e.g., selectable) volumes and/or pressures and/or flow rates of viscus material into the tissue.

For example, described herein are apparatuses for automatic expulsion of a fluid having a body configured to be held in a user's hand, the body comprising: a storage chamber; a first delivery chamber fluidically connected to the storage chamber through a first port; a second delivery chamber fluidically connected to the storage chamber through a second port; a delivery port fluidically connected to the first delivery chamber and the second delivery chamber; and a drive system comprising a transmission operatively connected to the first delivery chamber and the second delivery chamber, wherein the drive system is configured to provide a continuous expulsion of fluid from the delivery port by alternately expelling fluid from the first delivery chamber out of the delivery port while filing the second delivery chamber with fluid from the storage chamber and ejecting fluid from the second delivery chamber out of the delivery port while filling the first delivery chamber with fluid from the storage chamber.

Any of these devices for automatic expulsion of a fluid may include: a hand-held housing configured to hold a storage chamber, a first delivery chamber, and a second delivery chamber, a fluid transfer manifold, and a drive system; a fluid transfer manifold in the housing, the fluid transfer manifold configured to fluidically connect the storage chamber to the first delivery chamber through a first fluidic pathway, to connect the storage chamber to the second delivery chamber through a second fluidic pathway, and to connect the first delivery chamber and the second delivery chamber to an output port; and a drive system in the housing, the drive system comprising a transmission configured to operatively connect to the first delivery chamber and to the second delivery chamber, wherein the drive system is configured to provide a continuous expulsion of fluid from the output port by alternately expelling fluid from the first delivery chamber out of the delivery port at 100 psi or more while filling the second delivery chamber from the storage chamber, and expelling fluid from the second delivery chamber out of the delivery port at 100 psi or more while filling the first delivery chamber from the storage chamber.

The drive system may further comprise a motor configured to drive the transmission and a power source configured to power the motor. In some examples the drive system comprises a battery or a mechanical driver configured to drive the transmission. The transmission may comprise a timing belt. The drive system may be configured to turn the timing belt alternately clockwise and counterclockwise.

Any of these apparatuses may include a fluid transfer manifold connecting the storage chamber, the first delivery chamber, the second delivery chamber, and the delivery port.

The device may be configured to deliver fluid with fluid pressure of at least 100 psi, or at least 150 psi at the delivery port while delivering at least 30 mls fluid, at least 45 mls fluid, at least 60 mls fluid, or at least 100 mls fluid through the fluid manifold.

The device may be configured to deliver fluid through the fluid transfer manifold from 0.5 cc/second to 8 cc per second, or from 1 cc/second to 5 cc/second.

In some examples, the device may include one or more sensors and a controller (e.g., microcontroller) configured to determine an expulsion parameter. For example, the expulsion parameter may correspond to the number of times the first and/or second delivery chamber has been filled, the number of times the first and/or second delivery chamber has been filled emptied, a volume of fluid removed from the device, or a volume of a fluid remaining in the device. In any of these devices, the sensor may comprise a quadrature encoder. Any of these apparatuses may include a limit switch configured to stop device fluid delivery.

In any of these examples, a part of the first fluidic pathway and the second fluidic pathway may be part of the same pathway.

The volume of the storage chamber may be from 15 ml to 175 ml, from 30 ml to 140 ml, and/or from 40 ml to 80 ml, etc. The volume of the storage chamber may be larger than the volume of either or both of the first injection chamber and the second injection chamber. In any of these apparatuses, an inner diameter of the first and/or second delivery chamber may be less than 12.1 mm inner diameter, less than 8.9 mm inner diameter, less than 6.5 mm inner diameter, or less than 4.9 mm inner diameter, etc.

The storage chamber and/or the first delivery chamber and/or the second delivery chamber may comprise a syringe. The syringe may be removable/replaceable. Any of these apparatuses may include an injection needle for fluidically connecting to the output port.

As mentioned, any of these apparatuses may include a controller (e.g., a microcontroller) configured to control the drive system. In some examples the flow rate and/or pressure may be regulated at least in part by the controller. In some examples, the apparatus may be configured to control the flow rate, and/or maintain a constant flow rate and/or constant pressure, by pre-pressurizing the delivery chamber(s) before they are opened for delivering fluid. Thus, any of these methods and apparatuses may include pre-pressurizing (and/or monitoring pressure in) the delivery chambers as part of the reciprocal filling/ejecting cycle.

As mentioned, also described herein are methods of expelling a fluid from an automatic expulsion device, comprising: continuously expelling a fluid from out of delivery port of a hand-held device while triggering a control on the device by alternately: ejecting fluid from out of a first delivery chamber of an automatic expulsion device out of the delivery port at 100 psi or more while filling a second delivery chamber with fluid from a fluid storage chamber of the automatic expulsion device and ejecting fluid from out of a second delivery chamber of the automatic expulsion device out of the delivery port at 100 psi or more while filling the first deliver chamber with fluid from the fluid storage chamber.

Any of these methods may include repeating the expelling and filling steps at least two times, at least five times, or at least ten times, etc. Any of these methods may include measuring or determining an expulsion parameter using a sensor of the automatic expulsion device.

In general, the expulsion parameter may correspond to a number of times the first and/or second delivery chamber has been filled, emptied or moved, a volume of fluid removed from the device, a volume of a fluid remaining in the device, or a fluid pressure. A fluid pressure in a fluid manifold of the device may be between 3 psi and 500 psi, or between 5 psi and 250 psi, etc. Any of these methods may include measuring a fluid pressure of the fluid with a fluid sensor in the device. Thus, any of these methods may include maintaining a pressure and/or flow rate out of the device. As mentioned, a diameter of the first delivery chamber may be less than 12.1 mm inner diameter, less than 8.9 mm inner diameter, less than 6.5 mm inner diameter, or less than 4.9 mm inner diameter, etc. The device may comprise a fluid transfer manifold, the method further comprising delivering fluid having a fluid pressure of at least 100 psi, or at least 150 psi in the fluid transfer manifold.

Any of these methods may include delivering fluid through the fluid transfer manifold from 0.5 cc/second to 8 cc per second, or from 1 cc/second to 5 cc/second, etc.

In any of these methods and apparatuses, the drive system may comprise a motor and a pulley or a roller, and expelling and filling may further comprise rotating the motor and engendering relative motion between the pulley or roller and the first and/or second delivery chambers, to alternately expel and fill the first delivery chamber and the second delivery chamber with fluid. Further, any of these methods may include inserting a hollow sharp needle coupled to the delivery port into a first tissue of a patient. Expelling may include expelling the fluid into a subject through the hollow sharp needle, and/or stopping expelling, moving the hollow sharp needle into a second tissue of the patient, and resuming expelling. This may be repeated (e.g., repeating the stopping step) at least one time, at least two times, at least five times, at least ten times or at least twenty times, etc. Any of these methods may further include taking a tissue sample from a patient through the hollow sharp needle and determining if the tissue sample is a blood sample and removing the hollow sharp needle from the patient without expelling fluid if the tissue sample is a blood sample.

The automatic expulsion device may include a battery or a mechanical energy storage component, the method further comprising powering the expelling and filling steps using the battery or mechanical energy storage component. For example, the automatic expulsion device may comprise a mechanical energy storage component, further comprising manually charging the mechanical energy storage component by moving a lever on the automatic expulsion device.

For example, described herein are apparatuses (e.g., devices and systems) for injecting a fluid (e.g., a medication, including but not limited to viscus or highly viscus fluids). These devices are hand-held and do not require the use of additional cord/connectors. These devices may include multiple operational modes, including filling, injecting and aspirating. In the injecting mode, the device may be configured to run continuously ("freestyle") or inject a predefined volume of fluid (e.g., 1 cc, 2 cc, 3 cc, 5 cc, 10 cc, etc.).

An apparatus (e.g., a system, a device, etc.) for injecting a fluid may include: a reservoir; a first piston chamber fluidically connected to the reservoir through a manifold; a second piston chamber fluidically connected to the reservoir through the manifold; a plurality of check valves in the manifold; a delivery port fluidically connected to the first piston chamber and the second piston chamber through the manifold; a drive assembly comprising a transmission operatively connected to a first piston in the first piston chamber and a second piston in the second piston chamber, wherein the drive assembly reciprocally moves the first piston and the second piston to drive fluid in a continuous flow out of the delivery port by alternately driving fluid from the second piston chamber and the first piston chamber out of the delivery port while alternately transferring fluid from the reservoir into the first piston chamber and the second piston chamber; a motor coupled to the drive assembly; and a trigger control configured to activate the motor.

The apparatus may include one or more housings enclosing all or some of the components. For example, the apparatus may include a housing comprising a grip region configured to be held in a user's hand. The grip region may be shaped to fit and held into the palm of the user's hand (either left or right hand) and may be generally cylindrical.

In some examples the apparatus has two or more portions (such as a fluid-handling portion and a handle portion) that are connected together to form the apparatus (e.g., the device); each of these portions may include a housing at least partially enclosing components specific to each portion. For example, the handle portion may include a housing configured as a grip, as mentioned, and may include a control (e.g., trigger control) that the user may actuate. The handle portion or the fluid-handling portion may include a control (e.g., a fluid volume control) that the user may adjust to select between one or more predetermined delivery volumes and/or a continuous delivery mode in which fluid is delivery continuously while the trigger control is activated by the user.

In general, the apparatuses (e.g., devices) described herein may be configured to deliver fluid from the reservoir at relatively high pressure so as to be able to inject into body tissue that are otherwise resistant to injection. For example, the apparatuses described herein be configured, including the structure and/or arrangement of the manifold, the first piston chamber and the second piston chamber, to drive fluid in the continuous flow at 100 psi or more from the delivery port. In general, the first and second piston chambers may be sized so that they are relatively smaller volume (e.g., 1 cc, 2 cc, 3 cc, 5 cc, etc.) and communicate with the manifold through a small diameter (e.g., 5 mm or less, 4 mm or less, 3 mm or less, 2 mm or less, 1 mm or less) opening. Force is applied by the motor actuating the drive system so that the pistons within each piston chamber are moved in and out reciprocally, so that as one is moved into the piston chambers, the other is moved out of the piston chambers. The movement of the motor may be constant or variable. As will be described below in greater detail in some cases the movement of the motor (the rate) and therefore the movement of the drive system and pistons, may be adjusted based on the user actuation of the trigger control.

Any of these apparatuses (e.g., devices) may include a selector that may be coupled to the manifold and may be configured to select between an injection configuration of the manifold, a filling configuration of the manifold and an aspiration configuration of the manifold. In the injection configuration, the delivery port is in fluid communication with the first piston chamber and the second piston chamber. In the filling configuration the delivery port is closed (manually and/or automatically) and the reservoir is in fluid communication with a fill port. In the aspiration configuration the deliver port is in fluid communication with the fill port through the manifold.

As mentioned, any of these apparatuses may include a fluid volume control configured to select between one or more predetermined delivery volumes or a continuous mode. The device may deliver a volume of fluid based on a setting of the fluid volume control when a user actuates the trigger control. In some examples the fluid volume control is on the handle portion; in some examples the fluid volume control is on the fluid-handling portion. In some examples the controller controls the motor to deliver a volume of fluid based on a setting of the fluid volume control when a user actuates the trigger control.

Any of these apparatuses (e.g., devices) may include on or more indicators for indicating a status of the apparatus. For example, an indicator may be configured to indicate that the power is on/active. The same of a different indicator may indicate that a two (or more) component device is fully connected/assembled. The same of a different indicator may indicate that the reservoir is empty or not empty (and in some cases may indicate an approximate volume of fluid remaining in the reservoir or in the reservoir and piston chambers). The same or a different indicator may indicate that the pressure within the device (e.g., within the manifold) is above or below one or more thresholds. For example, any of these apparatuses (e.g., devices) may) include an indicator indicating when the reservoir is empty. For example, the apparatus may include an indicator may indicate when a pressure within the manifold exceeds a threshold value.

The apparatuses described herein may also include a pressure relief valve. For example, the apparatus may include a pressure relief value in the manifold.

The manifold is described in greater detail herein and may be configured in any of these apparatuses to be compact. The manifold may be configured to change configuration, as mentioned above, to switch between two or more different modes of operation, such as filling, injecting and aspirating. For example, in some cases the manifold may be configured to include a plurality of vales to direct fluid within the valve. Any of the valves described herein may be check valves. For example any of these apparatuses may include a manifold that includes a first check valve and a second check valve that are fluidly coupled to an input to the first piston chamber so that when the manifold is in an injection configuration fluid is passed from the reservoir into the first piston chamber as the first piston is withdrawn in the first piston chamber and fluid is passed from the first piston chamber out of the delivery port when the first piston is advanced in the first piston chamber, wherein the manifold is further configured so that a third check valve and a fourth check valve are fluidly coupled to an input to the second piston chamber so that in when the manifold is in the injection configuration fluid is passed from the reservoir into the second piston chamber as the second piston is withdrawn in the second piston chamber and fluid is passed from the second piston chamber out of the delivery port when the second piston is advanced in the second piston chamber.

In general, the apparatuses described herein may be configured so that they may include or be adapted to couple to a needle. For example, any of these apparatuses may include a delivery port is configured to couple to a needle, e.g., the delivery port may be threaded, or may be configured to couple with a Luer-Lock fitting.

For example, a device for injecting a fluid may include a housing; a reservoir comprising a bag at least partially within the housing; a first piston chamber fluidically connected to the reservoir through a manifold; a second piston chamber fluidically connected to the reservoir through the manifold; a delivery port fluidically connected to the first piston chamber and the second piston chamber through the manifold; a drive assembly comprising a transmission operatively connected to a first piston in the first piston chamber and a second piston in the second piston chamber, wherein the drive assembly reciprocally moves the first piston and the second piston; wherein the manifold is configured so that a first check valve and a second check valve are fluidly coupled to an input to the first piston chamber so that in when the manifold is in an injection configuration, fluid is passed from the reservoir into the first piston chamber as the first piston is withdrawn in the first piston chamber and fluid is passed from the first piston chamber out of the delivery port when the first piston is advanced in the first piston chamber, wherein the manifold is further configured so that a third check valve and a fourth check valve are fluidly coupled to an input to the second piston chamber so that when the manifold is in the injection configuration, fluid is passed from the reservoir into the second piston chamber as the second piston is withdrawn in the second piston chamber and fluid is passed from the second piston chamber out of the delivery port when the second piston is advanced in the second piston chamber; a motor coupled to the drive assembly; and a trigger control configured to activate the motor.

For example, described herein are apparatuses (e.g., devices) for injection of a fluid that include: a reservoir; a manifold comprising a plurality of check valves; a fill port fluidly connected to, or part of, the manifold; a first piston chamber fluidically connected to the manifold; a second piston chamber fluidically connected to the manifold; a drive assembly coupled to a first piston in the first piston chamber and a second piston in the second piston chamber; a delivery port fluidically connected to the manifold; a selector having a first position and a second position; and a spool (also referred to herein as a spool valve) within the manifold that is translationally coupled to the selector, so that: when the selector is in the first position, the delivery port is in fluid communication with the first piston chamber, the second piston chamber and the reservoir through the plurality of check valves so that as the drive assembly reciprocally drives the first piston and the second piston, fluid is alternately transferred from the reservoir and into the first piston chamber and the second piston chamber, and fluid is alternately driven from the second piston chamber and the first piston chamber and out of the delivery port, and when the selector is in the second position the reservoir is in fluid communication with the fill port.

Any of these apparatuses may be configured so that the selector includes a third position, and wherein when the selector is in the third position the delivery port is in fluid communication with the fill port and the reservoir, first piston chamber and second piston chamber are not in fluid communication with the delivery port.

As mentioned above, comprising an overpressure valve within the manifold configured to open when a pressure within the manifold exceeds a threshold value. In some cases, the apparatus may include a pressure sensor within the manifold configured to emit one or more alerts when the pressure sensor detects a pressure greater than a first threshold value or less than a second threshold value. For example, any of these apparatuses may include a pressure sensing chamber within the manifold comprising one or more biases configured to deflect a magnet within the pressure sensing chamber based on a pressure within the manifold.

In general, the manifold may be compact. For example, the manifold may be configured to have a length of about 5 cm or less (e.g., less than 5 cm, 4 cm or less, 3 cm or less, etc.) and height of about 6 cm or less (e.g., less than 6 cm, 5 cm or less, 4 cm or less, 3 cm or less, etc.).

In some examples the apparatus (e.g., device) includes a housing at least partially enclosing the manifold, and/or reservoir, and/or first piston chamber and/or second piston chamber. In some examples this housing may be a first housing, also referred to herein in some examples as an upper housing; this first housing may be coupled to a second housing (e.g., a lower housing). For example, the housing may be configured to couple with a hand-held base comprising a power supply and a motor so that the drive assembly engages with the motor to reciprocate the first piston and the second piston.

As mentioned, any of these apparatuses may include a control for selecting the mode of operation of the apparatus, and in particular for adjusting the state of the manifold. This control may be referred to herein as a selector. In some examples, the selector comprises a cam driving axial movement of the spool within the manifold.

For example, a device for injection of a fluid may include: a reservoir; a manifold comprising a plurality of check valves; a fill port fluidly connected to, or part of, the manifold; a first piston chamber fluidically connected to the manifold; a second piston chamber fluidically connected to the manifold; a drive assembly coupled to a first piston in the first piston chamber and a second piston in the second piston chamber; a delivery port fluidically connected to the manifold; a selector having a first position, a second position, and a third position; and a spool (e.g., spool valve) within the manifold that is translationally coupled to the selector, so that: when the selector is in the first position, the delivery port is in fluid communication with the first piston chamber, the second piston chamber and the reservoir through the plurality of check valves so when that the drive assembly reciprocally drives the first piston and the second piston, fluid is alternately transferred from the reservoir and into the first piston chamber and the second piston chamber and fluid is alternately driven from the second piston chamber and the first piston chamber out of the delivery port in a continuous flow, when the selector is in the second position, the reservoir is in fluid communication with the fill port, and when the selector is in the third position, the delivery port is in fluid communication with the fill port, and the reservoir, the first piston chamber and the second piston chamber are not in fluid communication with the delivery port.

In some examples an apparatus (e.g., a device) for injection of a fluid may include: a reservoir; a manifold comprising a plurality of check valves; a fill port fluidly connected to, or part of, the manifold; a first piston chamber fluidically connected to the manifold; a second piston chamber fluidically connected to the manifold; a drive assembly coupled to a first piston in the first piston chamber and a second piston in the second piston chamber; a delivery port fluidically connected to the manifold; a selector having a first position, a second position, and a third position; a spool within the manifold that is translationally coupled to the selector, so that: when the selector is in the first position, the spool is moved relative to the manifold so that the delivery port is in fluid communication with the first piston chamber, the second piston chamber and the reservoir through the plurality of check valves so that when that the drive assembly reciprocally drives the first piston and the second piston, fluid is alternately transferred from the reservoir and into the first piston chamber and the second piston chamber and fluid is alternately driven from the second piston chamber and the first piston chamber out of the delivery port in a continuous flow, when the selector is in the second position, the spool is moved so that the reservoir is in fluid communication with the fill port, and when the selector is in the third position, the spool is moved relative to the manifold so that the delivery port is in fluid communication with the fill port, and the reservoir, the first piston chamber and the second piston chamber are not in fluid communication with the delivery port; a pressure sensor within the manifold; and an indictor configured to emit one or more alerts when the pressure sensor detects a pressure greater than a first threshold value or less than a second threshold value.

Also described herein are methods of using any of the apparatuses described herein. For example, a method of injecting a fluid may include: maintaining a selector of a hand-held injection device to a first position so that a delivery port of the hand-held injection device is closed and a reservoir within the hand-held injection device is in fluid communication with a fill port; applying the fluid into the reservoir through the fill port of the hand-held injection device; moving the selector of the hand-held injection device to a second position so that the delivery port is in fluid communication with a first piston chamber of the hand-held injection device, a second piston chamber of the hand-held injection device and the reservoir through a plurality of check valves; and engaging a drive assembly of the hand-held injection device when a user engaged a trigger of the hand-held injection device while the selector is in the second position to reciprocally drive a first piston in the first piston chamber and a second piston in the second piston chamber to alternately transfer fluid from the reservoir and into the first piston chamber and the second piston chamber, and to alternately drive fluid from the second piston chamber and the first piston chamber out of the delivery port in a continuous flow.

Maintaining the selector of the hand-held injection device in the first position may include receiving the device with the selector already in the first position, or it may include moving the selector into the first position, or it may include confirming (e.g., by visual inspection or the like) that the selector is in the first position.

Any of these methods may include aspirating fluid through the device (e.g., from a needle attached to the tip). Any of these methods may include moving a selector of the hand-held injection device to a third position so that the delivery port is in fluid communication with the fill port, and the reservoir, the first piston chamber and the second piston chamber are not in fluid communication with the delivery port. For example, the methods described herein may include applying suction on the fill port to aspirate fluid from the delivery port when the selector is in the third position.

For example, a method may include coupling a handle portion of the hand-held injection device to a fluid-handing portion of the hand-held injection device, wherein the fluid-handing portion comprises the delivery port, the fill port, the reservoir, the first piston chamber and the second piston chamber, and wherein the handle portion comprises a power source and a motor.

The methods described herein may include assembling the apparatus from a fluid-handing component and a handle component. For example, any of the methods may include coupling by mechanically coupling the motor with a drive assembly in the fluid-handing portion, wherein the drive assembly couples to a first piston in the first piston chamber and a second piston in the second piston chamber to reciprocally drive the first piston and the second piston.

In any of these methods moving the selector of the hand-held injection device to the first position may comprise translating a spool in a manifold of the hand-held injection device.

Also described herein are apparatuses (and methods for using them) that allow a user (e.g., doctor, surgeon, nurse, assistant, etc.) to control the rate at which fluid is applied by the apparatus, and/or the force or pressure that fluid is applied, based on the force applied to the trigger control (or another control). This may be particularly useful when the apparatus is operated in the continuous (e.g., "freestyle") mode of operation. For example, described herein are apparatuses (e.g., devices) for injecting a fluid, the device comprising: a reservoir; a first piston chamber fluidically connected to the reservoir through a manifold; a second piston chamber fluidically connected to the reservoir through the manifold; a plurality of check valves in the manifold; a delivery port fluidically connected to the first piston chamber and the second piston chamber through the manifold; a drive assembly comprising a transmission operatively connected to a first piston in the first piston chamber and a second piston in the second piston chamber, wherein the drive assembly reciprocally moves the first piston and the second piston to drive fluid in a continuous flow out of the delivery port by alternately driving fluid from the second piston chamber and the first piston chamber out of the delivery port while alternately transferring fluid from the reservoir into the first piston chamber and the second piston chamber; a motor coupled to the drive assembly; a housing comprising a grip region configured to be held in a user's hand; a trigger control comprising a trigger sensor configured to detect force applied to the trigger control; and a controller, wherein the controller is configured to adjust a rate of the motor based on the force applied to the trigger control.

In some examples the trigger sensor comprises a force sensitive resistor. In some examples, the trigger sensor comprises a pressure sensor. In some examples the trigger control comprises a lever. Alternatively in some examples a separate control on the apparatus (either the handle portion of the fluid-handling portion) may be configured to adjust the rate at which fluid is applied by controlling the rate of movement of the motor and therefore of the drive assembly (and pistons).

As mentioned, any of these apparatuses may include a selector coupled to the manifold and configured to select between an injection configuration of the manifold, a filling configuration of the manifold and an aspiration configuration of the manifold, wherein in the injection configuration the delivery port is in fluid communication with the first piston chamber and the second piston chamber, wherein in the filling configuration the delivery port is closed and the reservoir is in fluid communication with the fill port, and wherein in the aspiration configuration the delivery port is in fluid communication with the fill port through the manifold.

Any of these apparatuses may include a fluid volume control configured to select between one or more predetermined delivery volumes (e.g., 1 cc, 2 cc, 3 cc, 4 cc, 5 cc, 6 cc, 7 cc, 8 cc, 9 cc, 10 cc, 15 cc, etc.) and a continuous mode; the controller may control the motor to deliver a volume of fluid based on a setting of the fluid volume control when the user actuates the trigger control. For example, the controller may be configured to adjust the rate of the motor based on the force applied to the trigger control when the fluid volume control is in the continuous mode.

As mentioned, any of these apparatuses may include an indicator indicating when the reservoir is empty, and/or a pressure relief value in the manifold. Any of these apparatuses may include an indicator indicating when a pressure within the manifold exceeds a threshold value. The manifold may be configured so that a first check valve and a second check valve are fluidly coupled to an input to the first piston chamber so that when the manifold is in an injection configuration fluid is passed from the reservoir into the first piston chamber as the first piston is withdrawn in the first piston chamber and fluid is passed from the first piston chamber out of the delivery port when the first piston is advanced in the first piston chamber, wherein the manifold is further configured so that a third check valve and a fourth check valve are fluidly coupled to an input to the second piston chamber so that in when the manifold is in the injection configuration fluid is passed from the reservoir into the second piston chamber as the second piston is withdrawn in the second piston chamber and fluid is passed from the second piston chamber out of the delivery port when the second piston is advanced in the second piston chamber.

For example, a device for injecting a fluid may include: a reservoir; a first piston chamber fluidically connected to the reservoir through a manifold; a second piston chamber fluidically connected to the reservoir through the manifold; a plurality of check valves in the manifold; a delivery port fluidically connected to the first piston chamber and the second piston chamber through the manifold; a drive assembly comprising a transmission operatively connected to a first piston in the first piston chamber and a second piston in the second piston chamber, wherein the drive assembly reciprocally moves the first piston and the second piston to drive fluid in a continuous flow out of the delivery port by alternately driving fluid from the second piston chamber and the first piston chamber out of the delivery port while alternately transferring fluid from the reservoir into the first piston chamber and the second piston chamber; a motor coupled to the drive assembly; a housing comprising a grip region configured to be held in a user's hand; a trigger control comprising a trigger sensor configured to detect force applied to the trigger control; a fluid volume control configured to select between one or more predetermined delivery volumes and a continuous mode; and a controller, wherein the controller is configured to adjust a rate of the motor based on the force applied to the trigger control when the fluid volume control is set to the continuous mode.

Any of these apparatuses may be configured as two (or more) component devices that may be assembled together by the user (or another) prior to using the apparatus. For example, in some cases the combined apparatus (e.g., a system or device) may include a first fluid-handling portion that coupled to a second handle portion. The two may engage with each other so that a power source and driver (e.g., motor) in the handle portion engages with the drive system in the fluid-handling portion.

In some cases one component (e.g., the fluid handling component) is disposable or single-patient use, while the handle portion may be reusable (e.g., with different patients). Any of these apparatuses (e.g., devices or systems) for injecting a fluid may include: a fluid-handing portion and a handle portion that are coupled together for use. The assembled apparatus may also and equivalently be referred to as a system or as a device; in addition, the individual fluid-handling component may be referred to as a sub-assembly or as a device.

For example, described herein are systems for injecting a fluid, the system comprising: a fluid-handing portion comprising: a reservoir; a first piston chamber fluidically connected to the reservoir through a manifold; a second piston chamber fluidically connected to the reservoir through the manifold; a plurality of check valves in the manifold; a delivery port fluidically connected to the first piston chamber and the second piston chamber through the manifold; a drive assembly comprising a transmission operatively connected to a first piston in the first piston chamber and a second piston in the second piston chamber, wherein the drive assembly reciprocally moves the first piston and the second piston to drive fluid in a continuous flow out of the delivery port by alternately driving fluid from the second piston chamber and the first piston chamber out of the delivery port while alternately transferring fluid from the reservoir into the first piston chamber and the second piston chamber; a first housing at least partially covering the reservoir, manifold, first piston chamber and second piston chamber; and a handle portion comprising: a motor coupled to the drive assembly; a trigger control configured to activate the motor; and a second housing comprising a grip region configured to be held in a user's hand, wherein the handle portion and the fluid-handling portion are configured to releasably couple so that the motor engages with the drive assembly to reciprocate the first piston and the second piston.

Any of these apparatuses may include a securement to hold two (or more) components, such as the fluid-handling portion and the handle portion, together. For example, any of these apparatuses may include a latch configured to releasably secure the fluid-handing portion to the handle portion. The securement may include a lock. In some examples the two (or more) components may be permanently coupled together or may be temporarily (e.g., releasably) coupled together.

In general, the apparatuses described herein may include one or more sensors, such as pressure sensors, that may monitor and react to pressure within the apparatus, and particularly within the manifold, such as by applying a warning, releasing a pressure release valve, triggering an alert, etc. For example, any of these apparatuses (e.g., systems) described herein may include a magnet within the manifold of the fluid-handling portion configured to move relative to an internal fluid pressure within the manifold, wherein the handle portion comprises a magnetic sensor configured to detect a position or a change in position of the magnet.

In some examples the fluid-handling portion may include a selector coupled to the manifold and configured to select between an injection configuration of the manifold, a filling configuration of the manifold and an aspiration configuration of the manifold, wherein in the injection configuration the delivery port is in fluid communication with the first piston chamber and the second piston chamber, wherein in the filling configuration the delivery port is closed and the reservoir is in fluid communication with a fill port, and wherein in the aspiration configuration the delivery port is in fluid communication with the fill port through the manifold.

In some examples the apparatus may include a fluid volume control on the handle portion configured to select between one or more predetermined delivery volumes or a continuous mode, wherein the system delivers a volume of fluid based on a setting of the fluid volume control when the user actuates the trigger control.

In some examples, the handle portion comprises a fluid volume control selectable by the user and configured to select between one or more predetermined delivery volumes and a continuous mode, and a controller, wherein the controller controls the motor to deliver a volume of fluid based on a setting of the fluid volume control when the user actuates the trigger control.

As mentioned, any of these apparatuses may include a manifold that is configured so that a first check valve and a second check valve are fluidly coupled to an input to the first piston chamber so that when the manifold is in an injection configuration fluid is passed from the reservoir into the first piston chamber as the first piston is withdrawn in the first piston chamber and fluid is passed from the first piston chamber out of the delivery port when the first piston is advanced in the first piston chamber, wherein the manifold is further configured so that a third check valve and a fourth check valve are fluidly coupled to an input to the second piston chamber so that in when the manifold is in the injection configuration fluid is passed from the reservoir into the second piston chamber as the second piston is withdrawn in the second piston chamber and fluid is passed from the second piston chamber out of the delivery port when the second piston is advanced in the second piston chamber.

The apparatuses described herein may be operated as part of a surgical or non-surgical, including cosmetic indications.

For example, although the majority of the examples described herein may be used to apply a medication to a patient (human and non-human patients, including animals), these apparatuses and methods may also or alternatively be used to apply a fluid to plants and other organisms. These apparatuses may be used to apply fluid (including in particular a viscus fluid) as part of any method that would benefit from the controlled injection of fluid.

For example, described herein are methods, comprising: assembling a fluid-handing portion of an injection system with a handle portion of the injection system by coupling the fluid-handling portion to the handle portion so that a motor in the handle portion engages a drive assembly in the fluid-handling portion; filling a reservoir within the fluid-handling portion with a fluid while a selector on the fluid-handling portion is set to a fill position so that a manifold within the fluid-handling portion is in a fill configuration with the reservoir in fluid communication with a fill port on the fluid-handling portion through the manifold; setting the selector on the fluid-handing portion to an injection position so that the manifold is in an injection configuration in which a delivery port of the fluid-handing portion is in fluid communication with a first piston chamber, a second piston chamber and the reservoir through a plurality of check valves; and ejecting fluid from the delivery port when a trigger control on the handle portion is activated by activating the motor so that the drive assembly reciprocally drives a first piston in the first piston chamber and a second piston in the second piston chamber to alternately transfer fluid from the reservoir and into the first piston chamber and the second piston chamber, and to alternately drive fluid from the second piston chamber and the first piston chamber out of the delivery port in a continuous flow. In some examples, assembling the fluid-handling portion turns on power to the injection system.

Any of these methods may include attaching an injection needle to the delivery port (e.g., via a Lure lock attachment on the delivery port). Any of these methods may include setting the selector to a fill position prior to filling the reservoir. Fluid may be filled by applying (e.g., from a syringe or other connector attached to the fill port on the apparatus (e.g., on the fluid-handling portion, coupled to the manifold). In one example a 60 cc syringe of fluid material to be injected with the device may be loaded via the fill port (via a Luer lock connector). When filling the delivery port may be closed, automatically (e.g., by the change in configuration of the manifold, e.g., by one or more valves, include a ball valve) and/or manually by capping or closing the delivery port. For example, any of these methods may include closing the delivery port before filling the reservoir. Prior to injection, any of these methods may include priming the injection system.

In some examples, the method includes setting a fluid volume control to a pre-set volume mode (e.g., to deliver a pre-set volume such as 1 cc, 2 cc, 3 cc, etc.) or to a continuous delivery mode prior to ejecting fluid from the delivery port.

In any of these methods, ejecting fluid from the delivery port may include ejecting fluid to a predefined volume when a fluid volume control is set to a predefined volume mode. In some examples, ejecting fluid to the predefined volume comprises encoding movement of the drive assembly and comparing the encoded movement to a predefined value. In some examples ejecting fluid from the delivery port comprises adjusting a rate of movement of the drive assembly based on force applied to the trigger control. For example, ejecting fluid from the delivery port may comprise continu-ously ejecting fluid from the delivery port while the trigger control is activated by a user.

Any of the methods may include ejecting fluid from the delivery port by reciprocating the motor so that the motor is driven alternately clockwise and counterclockwise. The reciprocating movement of the motor may thus drive the drive assembly (e.g., a pulley, belt, etc.) in a reciprocating manner to move the attached pistons in and out of their respective piston chambers.

Any of these methods may include setting the selector on the fluid-handing portion to an aspiration position so that the manifold is in an aspiration configuration in which delivery port is in fluid communication with the fill port and the reservoir, the first piston chamber and the second piston chamber are not in fluid communication with the delivery port. For example, these methods may include aspirating through the injection system by applying suction to the fill port.

Thus, described herein are methods comprising: filling a reservoir within a hand-held injection system with a fluid while a selector on the hand-held injection system is set to a fill position so that a manifold within the hand-held injection system is in a fill configuration with the reservoir in fluid communication with a fill port on the hand-held injection system through the manifold; setting the selector to an injection position so that the manifold is in an injection configuration in which a delivery port of the hand-held injection system is in fluid communication with a first piston chamber, a second piston chamber and the reservoir through a plurality of check valves; and ejecting fluid from the delivery port when a trigger control on a handle of the hand-held injection system is activated so that a drive assembly reciprocally drives a first piston in the first piston chamber and a second piston in the second piston chamber to alternately transfer fluid from the reservoir and into the first piston chamber and the second piston chamber, and to alternately drive fluid from the second piston chamber and the first piston chamber out of the delivery port in a continuous flow.

In some examples, the reservoir of any of the apparatuses described herein may be configured as a collapsible/conformable bag. The bag may be biased within a housing of the apparatus so that there is a pressure applied to drive the fluid out of the reservoir, even when not actively pumped (e.g., by the action of the piston movement in the piston chambers). This may help assist the apparatus in injecting fluid and in rapidly reloading the piston chambers.

For example, described herein are apparatuses in which the reservoir comprises a bag and a foam material arranged against the bag to provide a compressive force. In some examples the device includes: a housing; a reservoir comprising a bag at least partially within the housing; a compressible foam within the housing and adjacent to the reservoir, and configured to apply a compressive force to collapse the reservoir; a first piston chamber fluidically connected to the reservoir through a manifold; a second piston chamber fluidically connected to the reservoir through the manifold; a delivery port fluidically connected to the first piston chamber and the second piston chamber through the manifold; a drive assembly comprising a transmission operatively connected to a first piston in the first piston chamber and a second piston in the second piston chamber, wherein the drive assembly reciprocally moves the first piston and the second piston; wherein the manifold is configured so that a first check valve and a second check valve are fluidly coupled to an input to the first piston chamber so that in when the manifold is in an injection configuration, fluid is passed from the reservoir into the first piston chamber as the first piston is withdrawn in the first piston chamber and fluid is passed from the first piston chamber out of the delivery port when the first piston is advanced in the first piston chamber, wherein the manifold is further configured so that a third check valve and a fourth check valve are fluidly coupled to an input to the second piston chamber so that when the manifold is in the injection configuration, fluid is passed from the reservoir into the second piston chamber as the second piston is withdrawn in the second piston chamber and fluid is passed from the second piston chamber out of the delivery port when the second piston is advanced in the second piston chamber. In some examples the compressive foam is an open cell foam. The reservoir may be driven against the housing by the compressible foam.

These apparatuses may include any of the features described above. For example, the apparatus (e.g., device) may include a selector on the housing having a first position and second position, wherein the selector is configured to transition the manifold between the injection configuration corresponding to the first position and a fill configuration corresponding to the second position, wherein in the fill configuration the reservoir is in fluid communication with a fill port in fluid communication with the manifold. The device of may include an overpressure valve within the manifold configured to open when a pressure within the manifold exceeds a threshold value. In some examples, the device may include a pressure sensor within the manifold configured to emit one or more alerts when the pressure sensor detects a pressure greater than a first threshold value or less than a second threshold value. For example, the device may include a pressure sensing chamber within the manifold comprising one or more biases configured to deflect a magnet within the pressure sensing chamber based on a pressure within the manifold.

In some examples a device for injecting a fluid may include: a housing; a reservoir comprising a bag at least partially within the housing; a compressible foam within the housing and adjacent to the reservoir, and configured to apply a compressive force to collapse the reservoir; a first piston chamber fluidically connected to the reservoir through a manifold; a second piston chamber fluidically connected to the reservoir through the manifold; a plurality of check valves in the manifold; a delivery port fluidically connected to the first piston chamber and the second piston chamber through the manifold; and a drive assembly comprising a transmission operatively connected to a first piston in the first piston chamber and a second piston in the second piston chamber, wherein the drive assembly reciprocally moves the first piston and the second piston to drive fluid in a continuous flow out of the delivery port by alternately driving fluid from the second piston chamber and the first piston chamber out of the delivery port while alternately transferring fluid from the reservoir into the first piston chamber and the second piston chamber.

Thus, in general, the apparatuses described herein may include devices for injecting a fluid that include: a reservoir; two or more piston chamber fluidically connected to a reservoir through a manifold and to the reservoir, and a drive assembly and motor for driving the injection of fluid from the two or more piston chambers into the manifold and out of a delivery port (to which an needle may be attached). The device may also include a handle with a control to actuate the device (such as a trigger control). Any of these devices may include a controller that may control activation of the device. The manifold may be configured with valves for switching between the two or more piston chambers so that a continuous flow out of the delivery port may be achieved. In some examples the device may include a control (switch, lever, etc.) for switching between a continuous mode or a pre-set volume delivery mode. Any of these device may include a control for switching between injection/injecting, re-filling of the reservoir, and in some examples, aspirating from the injection port.

Also described herein are apparatuses (devices and systems) in which the drive assembly includes a belt coupled to the pistons to alternately drive and retract the pistons of the piston chambers. The belt may be a chain, wire, robe, etc. The belt let may be reciprocated (e.g., driven in a first direction, then a second direction, based on the gearing and/or under control of a controller. The controller may control the operation (and/or direction of rotation) of one or more motors.

Any of the apparatuses described herein may include one or more registration checkpoints as described herein. The registration check points may be used for tracking and/or controlling movement and/or operation of the apparatus. For example, one or more registration checkpoints may be present on the front, back, left side, right side, top and/or bottom.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative examples, in which the principles of the invention are utilized, and the accompanying drawings of which:

FIG. 3I shows a top perspective view of a carriage useful for translating part of a delivery chamber.

FIG. 3J shows a perspective view of the proximal end of the carriage shown in FIG. 3H.

FIG. 3K shows a side perspective view of a shaft configured to fit into the carriage shown in FIG. 3H and FIG. 3I.

FIG. 3L shows a bottom perspective view of the injection apparatus shown in FIG. 2A with a motor and switches.

FIG. 5A illustrates one portion of an interface of an apparatus as described herein.

FIG. 5B illustrates a portion of an apparatus as described herein.

FIG. 6 illustrates an example of a portion of an actuator assembly as described herein, showing one example of a selector control that may be used.

FIG. 7A shows a side schematic of part of a peristaltic fluid delivery system, including portions of an actuator assembly as described herein, showing a pressure driven (e.g., pump) mechanism including a plurality of rollers acting on a compressible hose or tube.

FIG. 7B shows a side schematic of the peristaltic fluid delivery system shown in FIG. 7A.

FIG. 7C shows a schematic cross-sectional view of the peristaltic fluid delivery system shown in FIG. 7B.

FIG. 14 shows another example of an injection apparatus with a pressurized fluid chamber.

FIG. 15A schematically illustrates one example of a method of operation a hand-held injection apparatus as described herein.

FIG. 15B schematically illustrates an example of a method of operating an injection apparatus as described herein.

FIG. 18A shows a front perspective view of some of the components of the apparatus. Other components are removed (such as the housing, storage chamber and fluid delivery chambers. FIG. 18B shows a rear partially exploded view. FIG. 18C shows a front perspective view in which a portion of the front housing has been made transparent to show the configuration of the components within this portion of the housing.

FIG. 19A shows the results of injection with a 25 gauge needle. FIG. 19B shows the results of an injection with a 22 gauge needle.

FIG. 21D is an exploded view of a manifold assembly similar to that shown in FIGS. 21A-21C.

FIG. 22A shows an example of a manifold assembly and a magnetic position sensor configured to detect pressure within the manifold assembly.

FIGS. 22B-22C show side perspective and sectioned views, respectively, of a portion of the pressure sensing assembly within a manifold assembly similar to that shown in FIG. 22A.

FIG. 31 shows an example of a shuttle that may be used within an injection apparatus similar to that shown in FIGS. 30A-30C.

FIG. 32A schematically illustrates one example of a fluid circuit for an injection apparatus as described herein.

FIG. 32B schematically illustrates an example of a fluid circuit (including an aspiration port) as described herein.

FIG. 33 is a chart illustrating a method of preparing an injection apparatus for use, including (optionally) assembling the apparatus, filling the apparatus and/or priming the apparatus.

FIG. 34 is a chart illustrating a method of operating an injection apparatus as described herein, including selecting the mode of operation (e.g., injection), selecting continuous or preset volume injection, optionally confirming the position of the needle by aspiration, and injecting material using the apparatus.

DETAILED DESCRIPTION

Figure 1A:
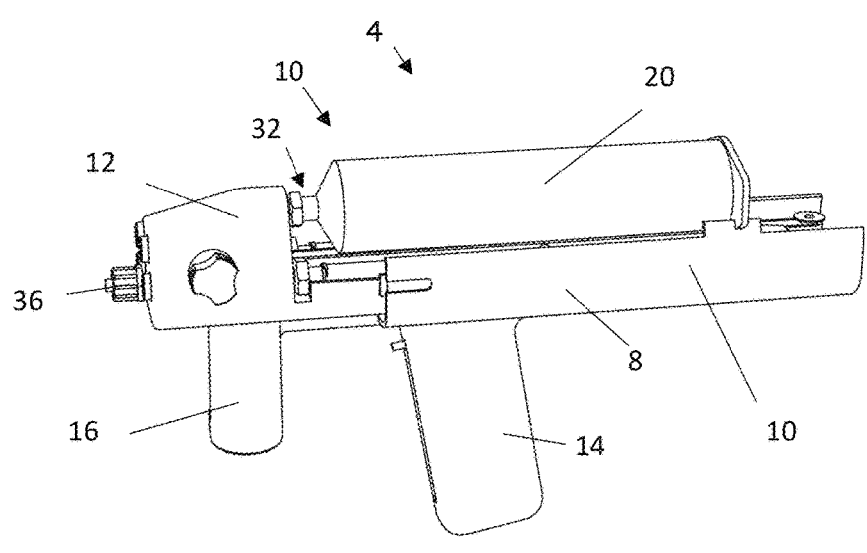
FIG. 1A shows a side perspective view of one example of an injection apparatus as described herein.

The apparatuses (e.g., devices, systems, etc., including in particular high-pressure injectors) described herein may inject a fluid, such as a drug and including, but not limited to, a viscus fluid, through a small-gauge needle into material, including the tissues of a body. The apparatus may provide the mechanical energy rejected to inject the fluid thereby reducing the operating force on the user's hand during an injection. These apparatuses may also inject within a set pressure range, and may inject a preset volume (e.g., 1 cc, 2 cc, 3 cc, 5 cc, 10 cc, etc.) and/or continuously. The injection may be at a constant rate or a rate that is input by the user as the user is injecting.

The apparatuses described herein may provide the injection energy during the injection. These apparatuses may be used for more than 15 (more than 20, more than 25, etc.) separate injections, and may include a refillable reservoir of between 30 cc to 60 cc (or more) capacity.

One particular advantage of these apparatuses is the ability of the device to both aspirate and to inject (in addition to filling). For example, a user (e.g., a doctor, surgeon, etc.) may aspirate through the same needle from which injections are performed. This may allow the user to confirm the absence/presence of any arterial inflow.

These apparatuses may inject materials at an injection rate that is greater than 0.25 cc/sec (e.g., 9.5 cc/sec, 0.75 cc/sec, 1 cc/sec, 1.25 cc/sec, etc.). The injection rate may be substantially constant. This injection rate may be significantly faster than manual injection (which may be less than 0.2 cc/sec and may require significant manual force). The apparatus may use any appropriate gauge needle, such as between 20G-32G (e.g., 20-22G needle, 30-32G needle, etc.), and any appropriate length of needle (such as between ½ inch to 3 inches, e.g., 1 inch, 1.5 inch, 2 inches, etc.).

As used herein a viscous material that may be injected using the apparatuses described herein may have a viscosity of between about 10 mPa*s and about 5000 mPa*s (at about 20 degrees C.). Thus, as will be described in greater detail here, these apparatuses may be used for a viscous fluid having a viscosity of less than about 5000 mPa*s (e.g., less than about 4000 mPa*s, less than about 3000 mPa*s, less than about 2000 mPa*s, less than about 1000 mPa*s, less than about 500 mPa*s, less than about 300 mPa*s, less than about 200 mPa*s, less than about 100 mPa*s, etc. at about 20 degrees C.).

In some examples, the apparatuses (e.g., systems, devices, kits and assemblies) and methods are described herein for delivering fluid to a patient, and particularly for delivering one or more doses of a viscous fluid using an apparatus that is configured to automatically and selectively deliver a predetermined dose at a high pressure. In some examples the material delivered may be highly viscus. These apparatuses may store multiple doses of the viscous material and are configured to provide sufficiently high fluid pressure to deliver the multiple doses of the viscous fluid, e.g., at set and/or selectable volumes, to the patient in ways that may be fast, easy, and safe for both the patient receiving the fluid and the operator delivering the fluid.

The apparatuses and methods described herein may be especially useful for delivering (e.g., topically or by injecting) viscous material into a patient's tissue. A viscous fluid may, for example, have viscosity of greater than $1\times10^{-4}$ Pa*S, greater than $5\times10^{-4}$ Pa*S, greater than $1\times10^{-3}$ Pa*S, greater than $5\times10^{-3}$ Pa*S, or greater than $1\times10^{-2}$ Pa*S. The apparatuses and methods described herein may be especially useful for delivering (e.g., topically or by injecting) a relatively large quantity of fluid to a patient. In some examples, a fluid of interest may be viscous and diluted prior to injection to reduce its viscosity, resulting in a large amount of diluted fluid to be delivered. The devices described herein, which may be automatic and/or continuous filling, may allow effective and safe injection of a viscous fluid and/or a relative large quantity of any fluid. In some particular examples, the apparatuses may be configured to provide sufficiently high fluid pressure to inject the viscous fluid into a plurality of tissues, some or all of which may be highly resistant to injection. For example, the apparatuses may be useful for injecting a fluid (medicament) into tissues of a joint, such as periosteum, (a dense layer of vascular connective tissue enveloping a bone), ligaments, tendons, and other joint tissues. The apparatuses and methods described herein may be especially useful for delivering (topically or by injecting) a viscous fluid to a patient.

The viscosity of a fluid is related to its internal resistance to flow. Viscosity can be defined in two ways: "kinematic viscosity" or "absolute viscosity." Kinematic viscosity is a measure of the resistive flow of a fluid under an applied force. The SI unit of kinematic viscosity is $mm^2$/sec, which is 1 centistoke (cSt). Absolute viscosity, sometimes called dynamic or simple viscosity, is the product of kinematic viscosity and fluid density. The SI unit of absolute viscosity is the millipascal-second (mPa-sec) or centipoise (cP), where 1 cP=1 mPa-sec.

The apparatuses described herein may generally be configured for continuous delivery of a material (e.g., a viscus material) into a patient, as described below. In some examples the material may be intermittently delivered, e.g., by pulsatile injection.

These apparatuses, which may be referred to herein a injectors, injector devices, devices for automatic expulsion of a fluid, or the like, are typically hand-held devices that may include a trigger or other control that may be actuated by the user to deliver a flow of material (viscus material) a constant or variable flow rate. The flow rate may be set by the user either before or during operation and may be adjustable. In some examples the flow rate is constant. In some examples the flow rate is pulsatile.

Any of these apparatuses may be configured as automatic or semi-automatic. For example, these apparatuses may include a drive motor that is generally located on the hand-held device. In some examples, the drive motor may be positioned at the proximal end of the hand-held device, e.g., near or at the upper end of the handle, so that it does not interface with the injection site. These devices may generally include a needle (hollow sharp distal end) extending from the distal end of the device. The device may include a plurality of valves to allow the control of flow from multiple sources, including multiple storages sources, such as multiple chambers and/or multiple removable bodies (e.g., in some examples syringe bodies). In some examples the plurality of valves may be held within and/or formed integrally as part of a fluid valve body, such as a fluid valve body assembly. The fluid valve body may be configured for injection molding processing and assembly. Any of these apparatuses may also include a controller, such as an electronic or electronics controller, which may be held within a housing in/on the device. The controller may control and/or coordinate operation of the apparatus as will be described in greater detail below.

In some examples the apparatus may include a control, such as a switch, selector, dial, valve, etc. configured as an injection selection switch. This control may have multiple settings that may control operation of the apparatus, including the selection of the amount of material to be injected per actuation of the device (e.g., by pulling or holding the trigger). For example, the switch may include settings for two or more of: continuous, 1 cc, 2 cc, 4 cc, 10 cc, etc., to control the device to deliver the selected amount per trigger pull. In general, the selection may be controlled based on the volume to be delivered. Alternatively or additionally, the apparatus may be configured to control delivery pressure (e.g., selecting among multiple delivery pressures). In some examples the apparatus may be calibrated to deliver a predetermined volume based on a selected delivery pressure, or vice versa.

Any of the apparatuses described herein may also or alternatively include one or more indicators on the body of the apparatus for indication the status of the apparatus, including the operational status and/or the amount of material delivered, to be delivered and/or remaining the body of the apparatus. For example, in some examples the apparatus includes one or more light emitting diodes (LEDs) that are configured to indicate injection status (ready to inject, injecting/system OK, over pressure/fault/motor stall fault, etc.) These different states may be indicated by color and/or position (e.g., yellow, green, red, etc.). To transition between operational states, the apparatus may be configured so that the user operates a control (such as the trigger), e.g., by releasing and/or sequentially releasing and engaging the trigger, etc. This may be indicated by the one or more indicators.

In some examples, the apparatus may be configured so that the user may apply a selectable amount of pressure to the grip and/or control (e.g., trigger) in order to control operation of the device, including control operation of the speed/rate of injection, the pressure, etc. For example, in some examples the apparatus may include one or more force sensitive resistors (FSRs) embedded in the handle grip. The selector may sense an amount of force (grip strength) on the handle or a region of the handle and may adjust the sleep of the injection. For example, if the injector is in a continuous position then squeezing the handle may be detected by the force sensor(s) and may adjust the speed of injection. The force sensor may be coupled to the controller (e.g., a micro-controller) that may then adjust the operation of the apparatus.

Figure 1B:
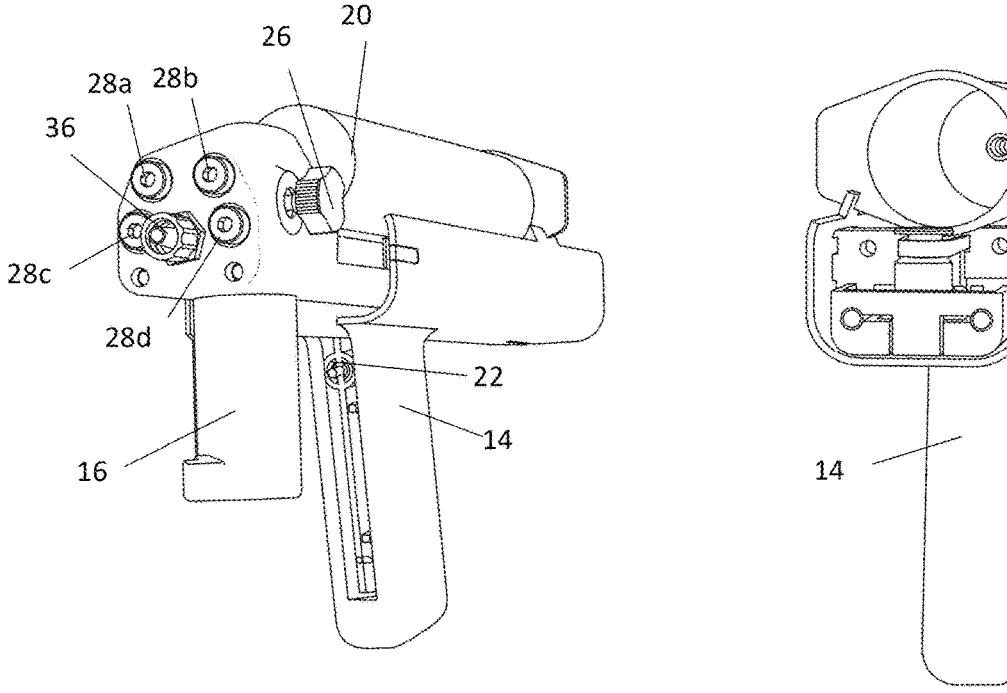
FIG. 1B shows a front perspective view of the injection apparatus shown in FIG. 1A.
Figure 1C:
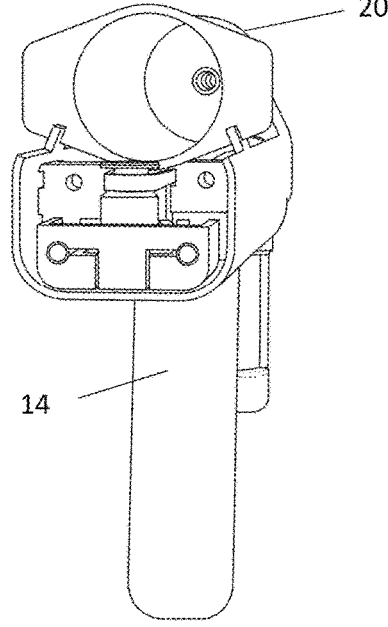
FIG. 1C shows a back perspective view of the injection apparatus shown in FIG. 1A.

FIGS. 1A-1C show different views of one example of an injection device 4 for delivering a fluid (e.g., a viscus fluid) to a patient. FIG. 1A shows a side perspective view of the device 4. The device 4 has a housing 8, a body region 10, and a head region 12. The body region 10 includes a storage chamber 20 for storing a fluid for delivery and a first grip 14. A storage chamber connector 32 fluidically connects the storage chamber 20 to a fluid transfer manifold 44 (shown in FIG. 2A) in the head region 12. The first grip 14 can be sized and shaped to be gripped by a user's hand. The first grip 14 includes a trigger 22 configured to control fluid delivery. The head region 12 also includes a delivery connector 36 configured to connect with and pass fluid from the fluid transfer manifold 44 in the head region 12 to a fluid delivery element, such as a needle (not shown in this view), for delivery to a patient. The delivery connector 36 may be a first fitting configured to mate with a second fitting, such as a sharp (needle). The delivery connection 36 and the connection on the second fitting may be a slip tip, such as a Luer lock or Luer slip fitting. FIG. 1A also shows head region 12 with a thumbscrew 26 and a second grip 16. FIG. 1B shows a front perspective view of the injection device shown in FIG. 1A. The first grip 14 and/or second grip 16 may be ergonomically sized and shaped, such as being curved for easier gripping or having finger and/or indents that may make for more secure gripping. The first grip 14 and/or second grip 16 may be made from plastic, and may be coated or covered for usability and comfort such as with a tacky or cushioned material. The device may be readily sterilizeable.

FIG. 1B shows the trigger 22 for controlling fluid movement and the switch 24 for turning the device on and off.

Figure 1D:
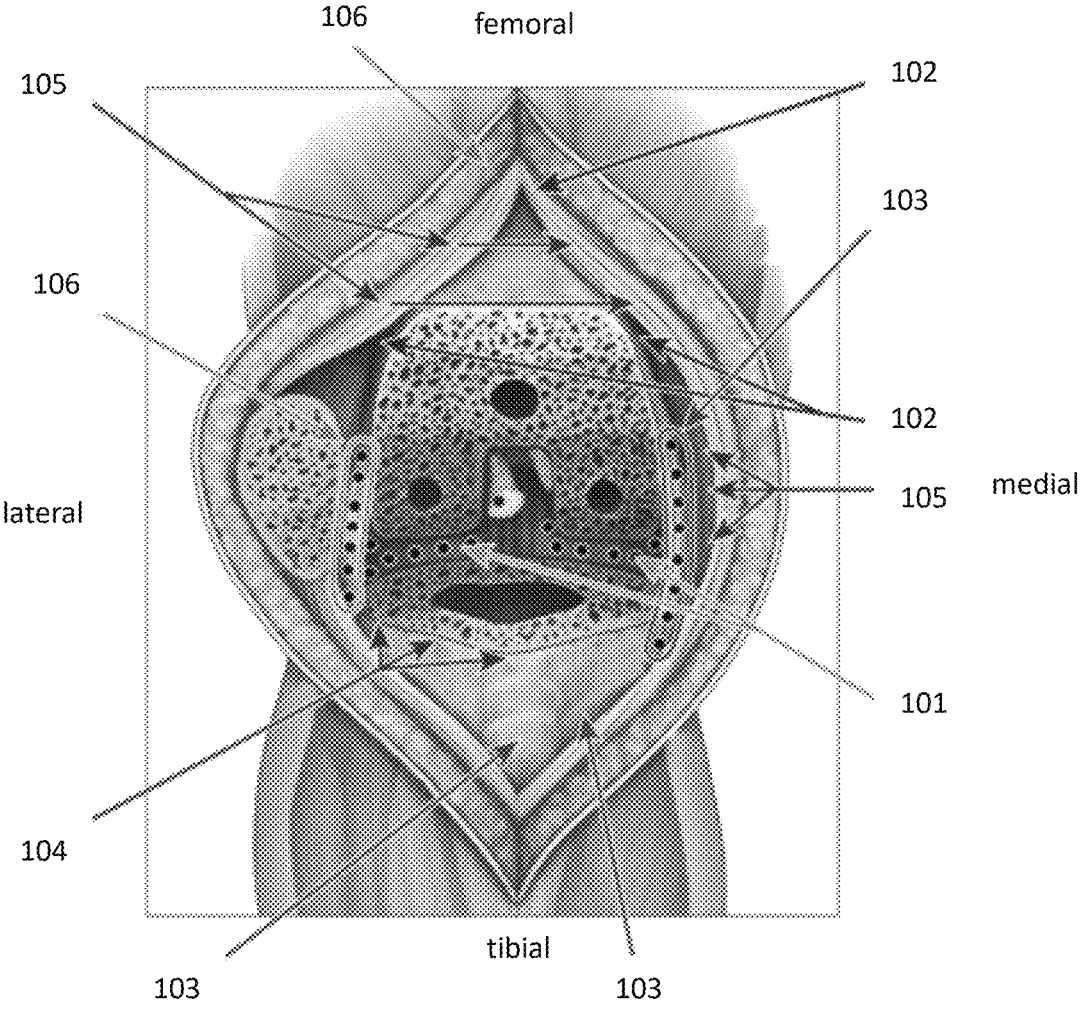
FIG. 1D shows an example of locations for injections into a knee joint.

In addition to the delivery connector 36, FIG. 1B shows the head portions of screws 21A, 21B, 21C, and 21D on the distal end of the device. In some examples, the screws corresponding to these 21A, 21B, 21C, 21D screw into channels in tubing or piping in the fluid transfer manifold 44, sealing the manifold from leakage. FIG. 1C shows a back perspective view of the injection device shown in FIG. 1A, looking down the barrel 30 of the storage chamber 20 from a proximal to distal direction. FIG. 1D shows a diagram of a knee joint and sites in and around the knee joint where an injection of a fluid (e.g., an anti-inflammatory drug or pain medication) may be made during a knee joint procedure using the devices or methods described herein. A plurality of injections may be made to deliver the fluid at a sufficiently high concentration to a sufficient number of tissues. The injections may be made by the injection device described herein by either moving a needle to a variety of different positions within the body, including to positions that are at different depths in the tissue (deeper or shallower in the tissue) or at separate locations (by removing the needle out of the tissue and from one site and reinserting it into a second site).

For example, by way of example only, a knee may be injected as shown in FIG. 1D. In this example, 8-10 sticks may be made, 101, in the medial posterior capsule, 8-10 sticks in the lateral posterior capsule 102, and in the femur-medial and lateral periosteum, posterior periosteum, supra-patellar/quadriceps tendon as shown 103. Five sticks may be made in the tibia fat pad 104, and 15-20 sticks may be made in the circumferential periosteum 105. Ten sticks are shown made in the midline quadriceps tendon 106 and ten sticks in the retinaculum, medial gutter, femoral to tibia 106, ten sticks in the lateral gutter, femoral to tibial and ten sticks subcutaneously for closure. The injections may be made using a continuous injection, or by selecting predetermined volumes or pressures. Each site may be, for example, injected with from 0.5 mls to 3 mls each.

Figure 2A:
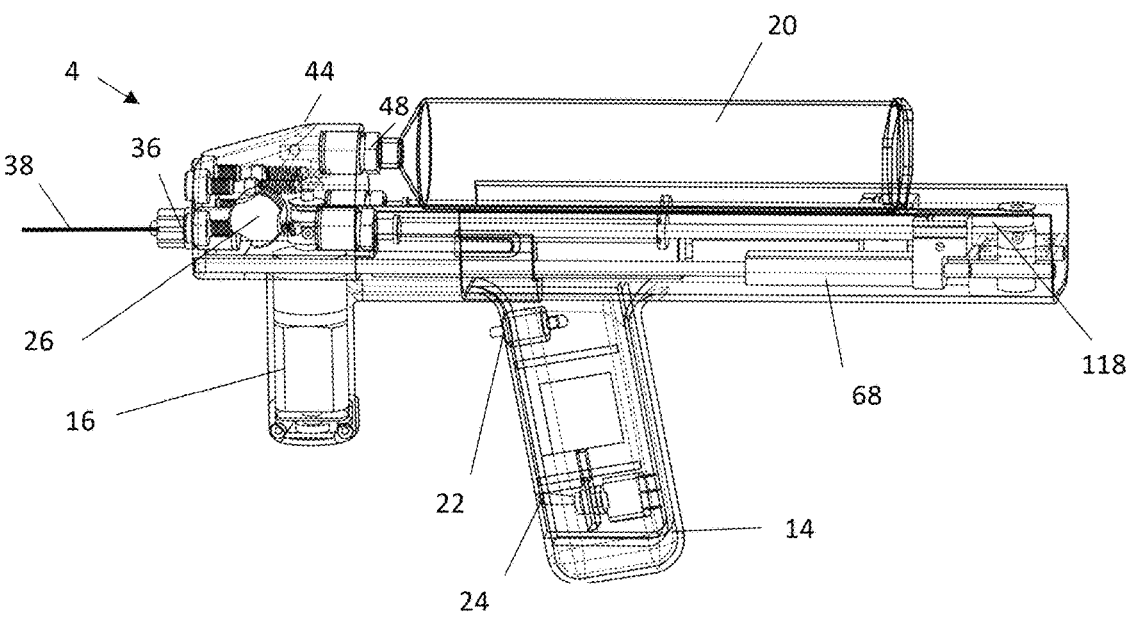
FIG. 2A shows a partially transparent side view of an example of an injection apparatus.
Figure 2B:
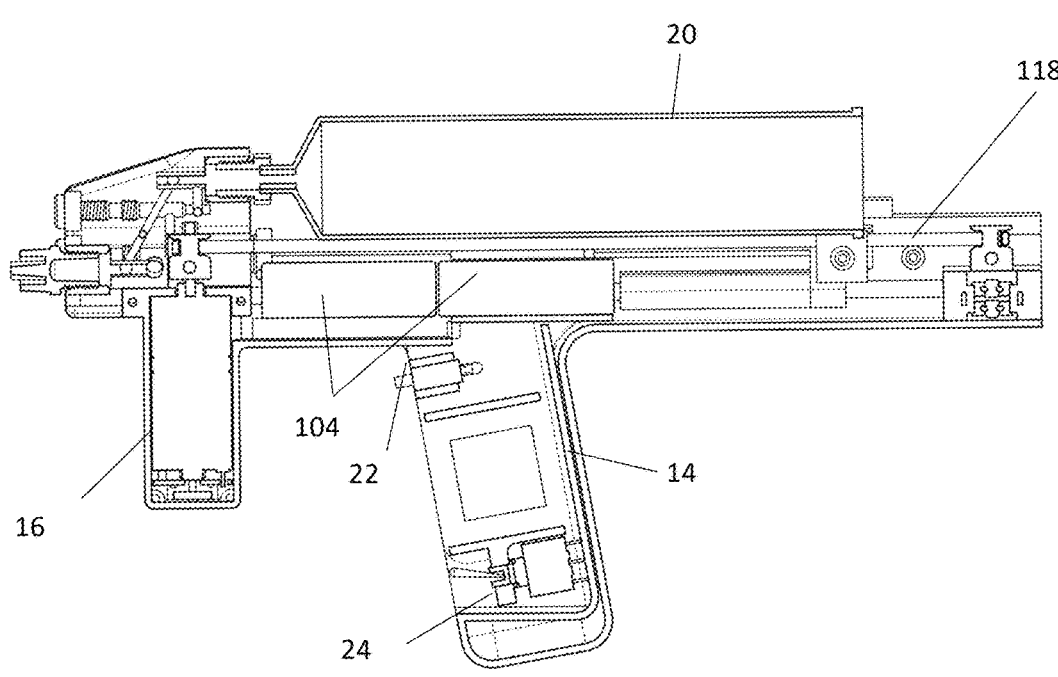
FIG. 2B shows a partial side cross-sectional of the injection apparatus shown in FIG. 2A.

FIGS. 2A-2B show partially transparent views of another example of a device 4 similar to that shown in FIG. 1A. FIG. 2A shows a partially transparent side view and FIG. 2B shows a partial side cross-sectional view. FIG. 2A shows the head region 12 as partially transparent to better illustrate the fluid transfer manifold 44 inside. FIG. 2B shows the second grip 16 as partially transparent to better show the motor 116 inside. The motor 116 is connected to the drive system and moves the timing belt 118. The motor 116 includes a sensor 100. The device 4 also includes a controller. The controller reads information from the sensor 100. The device 4 also includes a hall limit switch to find home on reset. The fluid transfer manifold 44 may be made from piping or tubing, may be assembled from separate pipes or tubing or may be made by additive manufacturing (e.g., 3D printing) as a single or several pieces. The sensor 100 may be an encoder configured to convert mechanical information (e.g., position of the motor shaft) into a usable electrical signal (that can be used by the micro controller to change a signal or data into a code. The encoder may track the turning of the motor shaft and detect movement direction and/or movement speed. The encoder could be a mechanical encoder (an electro-mechanical encoder), a magnetic encoder, an optical recorder, or a resistive encoder. The encoder may be a quadrature encoder configured to detect which way the motor shaft is turning. The encoder may be a rotary encoder and may convert the angular position of the motor shaft into a digital code rotation of the motor shaft. Although shown in the second grip 16 the sensor 100 could also be located elsewhere in the device.

In general, any of the apparatuses described herein may include two or more (e.g., a plurality) of sub-chambers, such as sub-cylinders, as secondary delivery chambers that mechanically multiply for force applied by the apparatus when delivering material from the storage chamber out of the needle. The apparatus may reciprocally pump, via one or more pistons, fluid from the storage chamber (which may be swapped out and/or refilled), into the smaller-volume secondary delivery chambers, and them reciprocally pumped out of the smaller-volume secondary delivery chambers and out of the distal end tip of the device, as described in greater detail below. In some examples, the ratio of the size and dimensions of the secondary delivery chambers may be calibrated so that the force required to pump from the smaller secondary chamber in order to achieve the higher pressure is less than a threshold.

Figure 3A:
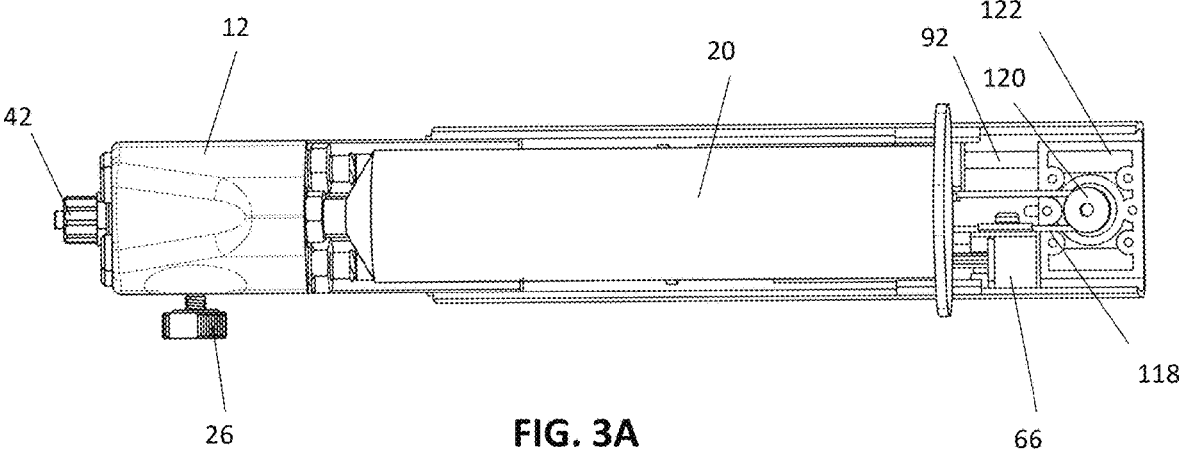
FIG. 3A shows a partial top perspective view of part of the drive system of the injection apparatus shown in FIG. 2A.
Figure 3B:
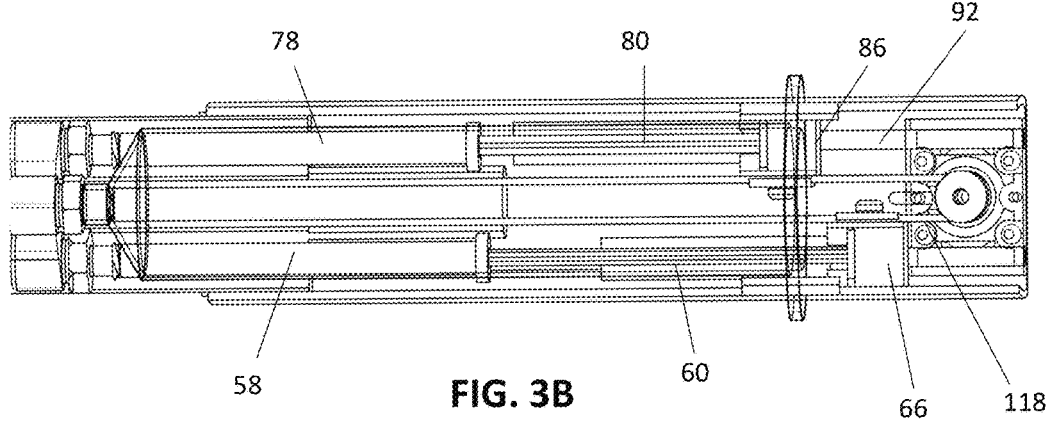
FIG. 3B shows a partial top cross-sectional view of the injection apparatus shown in FIG. 2A.

FIG. 3A-FIG. 3J show different views of the drive system of the device 4 configured to provide delivery of a fluid (e.g., continuous of a high-pressure fluid). In this example, the device 4 provides a continuous flow of high-pressure fluid for delivery by alternately passing fluid through one of two narrow delivery chambers before fluid delivery. FIG. 3A shows a partially cut-away top view of the device 4 shown in FIG. 1A. FIG. 3B shows a similar view as FIG. 3A with the storage chamber 20 and other components removed.

Figure 3C:
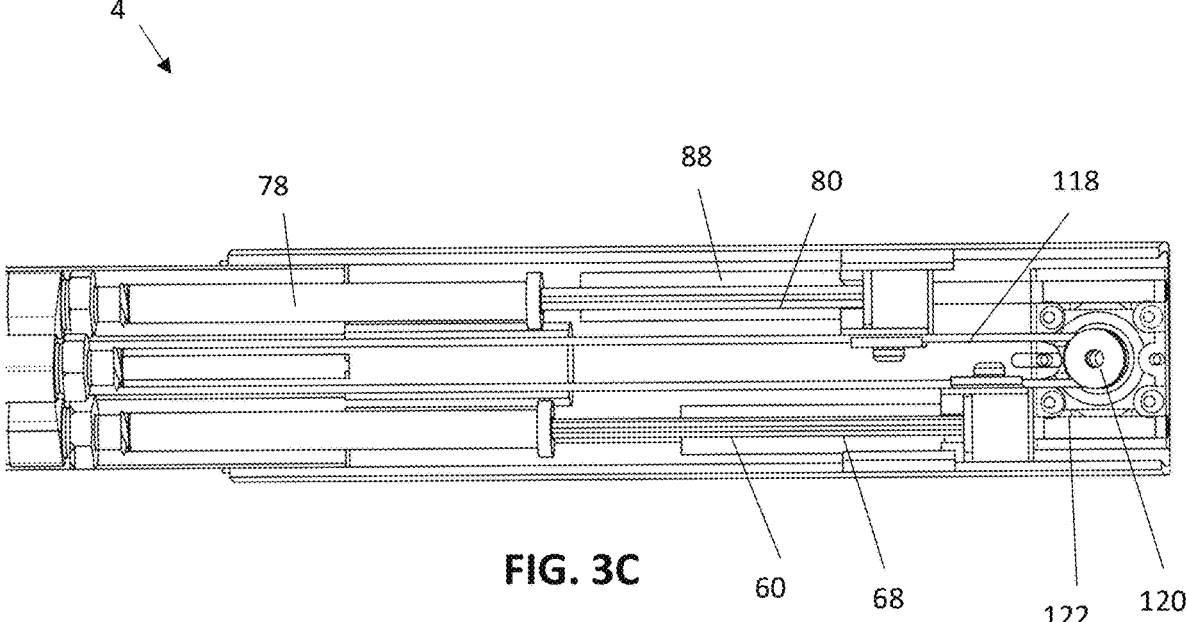
FIG. 3C shows a partial top cross-sectional view of the apparatus shown in FIG. 3B with the batteries removed.
Figure 3D:
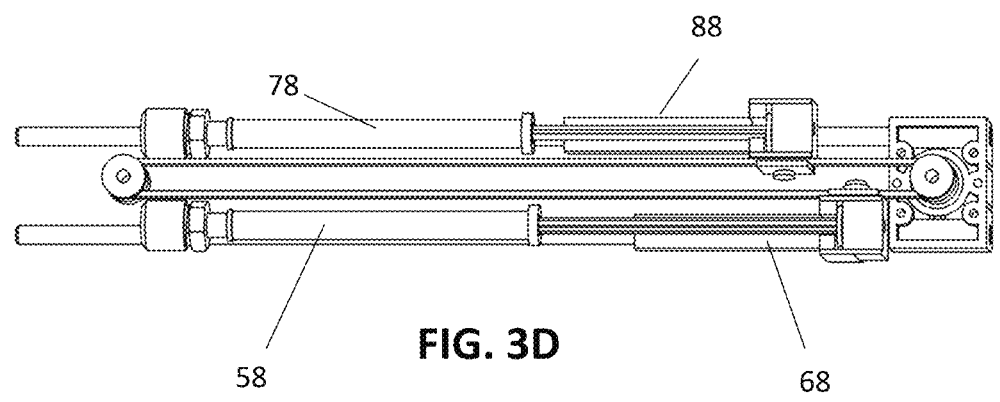
FIG. 3D shows a top cross-sectional view of the apparatus shown in FIG. 3B with various components removed.
Figure 3E:
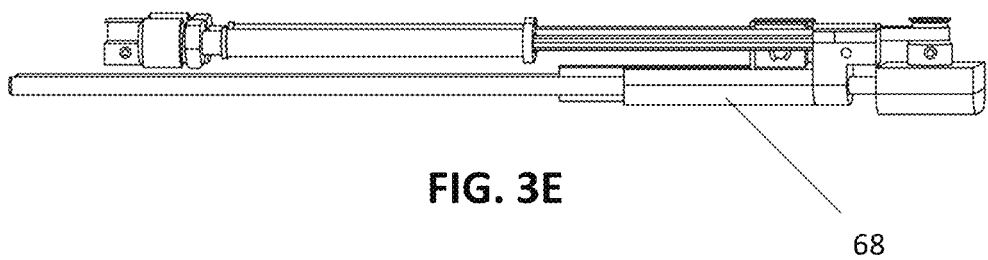
FIG. 3E shows a top cross-sectional view of the apparatus shown in FIG. 3D with additional components removed.

FIG. 3C shows a similar view with the battery 104 and other components removed. FIG. 3D shows a similar view with the housing and some of the other components removed. FIG. 3E shows a side view similar to the view in FIG. 3D with the first delivery chamber removed. FIG. 3A shows the timing belt 118 configured to rotate about the timing belt pulley 120 as the timing belt pulley 120 rotates. The timing belt pulley 120 is operationally connected to the first carriage 68 and the second carriage 84 (better seen in FIG. 3B and FIG. 3C). FIG. 3B and FIG. 3C show an example of the device 4 configured to use narrow delivery chambers, such as small, narrow syringes, as the first and second delivery chambers 58, 78 to provide high pressure out of the device 4 (e.g. for delivery to a patient). The first and second delivery chambers 58, 78 alternately deliver their fluid payloads to the delivery connector 36 and its connected delivery element 38 (for delivering to the patient; not shown in this view) for continuous fluid delivery from the device 4. In particular, while the first delivery chamber 58 is emptying its payload to the delivery connector 36 and its connected delivery element 38, the second delivery chamber 78 is filling with fluid from the storage chamber 20. FIG. 3B and FIG. 3C show first delivery chamber 58 with a corresponding first plunger 60 and second delivery chamber 78 with a corresponding second plunger 80. The first delivery chamber 58 is configured to receive the first plunger 60 and the second delivery chamber 78 is configured to receive the second plunger 80. The first plunger 60 is configured to slide along the inside of the barrel of the first delivery chamber 58 and the second plunger 80 is configured to slide along the inside of the second delivery chamber 78. FIG. 3B and FIG. 3C also show the timing belt 118 operatively connected to the first carriage 68 and the first carriage 68 operatively connected to the first plunger 60 so that when the timing belt 118 moves (rotates) clockwise, the first carriage 68 translates from a proximal location to a distal location. The first carriage carries the first plunger 60 and translates the first plunger 60 from a proximal location to a distal location, moving the first plunger 60 through the first delivery chamber 58, and expelling fluid out of the distal end of the first delivery chamber 58. In this example, the first and second delivery chambers 58, 78 are syringes that alternately empty and fill, although configurations that do not involve a syringe are also contemplated (see below). A delivery chamber or a storage chamber (e.g., a syringe) may be made from glass, metal, or plastic. In some particular examples, a syringe body and plunger made from polypropylene, a plunger or part of a plunger made from polyethylene. A delivery chamber (e.g., a syringe) may be a commercially available component (e.g., syringe, such as made by BD, Becton, Dickinson and Company, Franklin Lakes, NJ) or may be custom made. Delivery chambers may be configured to hold from 0.1 to 10 mls (10 cc). Delivery chambers may be 0.1 ml syringes, 1 ml syringes, 2 ml syringes, 3 ml syringes, 4 ml syringes, 5 ml syringes, 10 ml syringes, (or anything in between these sizes). Smaller syringes (e.g., those with a narrower bore) generally deliver higher pressures than do syringes with a larger bore, and so a narrow syringe with a longer barrel may be used to obtain a combination of high pressure and sufficient volume. An inner diameter of a first or second delivery chamber 58, 78 (syringe) may be less than 12.1 mm (e.g., a 3 ml or smaller syringe), less than 8.9 mm (e.g., a 1 ml or smaller syringe), less than 6.5 mm (e.g., 0.5 ml or smaller), or less than 4.9 mm. The delivery chamber size may be chosen so that it generates sufficient pressure for desired expulsion from the device 4 or injection into a tissue, especially a resistant tissue. A device with a 1 ml delivery chamber syringe may be chosen for injecting tissues with greater resistance, such as knee joint or hip joint tissues. In some examples, the delivery chamber(s) (and storage chamber) are part of a device. In other examples, the device may include some subsystems or parts described herein and exclude others. For example, some examples of devices described herein may include the delivery chamber (s) and/or storage chamber while in other examples, the device does not include the delivery chamber(s) and/or storage chamber. A device may be configured with one or more holder components configured to accept and/or attach some subsystems or parts, such as accepting and attaching a delivery chamber(s) and/or a storage chamber through snap fastener plastic beam snap-in part(s) or plastic cylinder snap-in part(s) on the device. The holder components may be configured to accept and hold an off-the-shelf or custom made part, such as an off-the-shelf or custom made syringe or other delivery chamber. Holder components be configured for accepting and/or holding various parts (e.g., delivery syringe barrel, delivery syringe plunger, storage syringe barrel, storage syringe plunger, battery). A syringe or delivery chamber may connect to other parts of the fluid transfer system of the device through a Luer lock or other connector.

FIG. 3B and FIG. 3C also show the timing belt 118 operatively connected to the first carriage 68 and the first carriage 88 operatively connected to the second plunger 80 so that when the timing belt 118 moves (rotates) clockwise (e.g., around a shaft of the pulley mount 122), the second carriage 88 translates from a more distal location to a more proximal location (e.g., in the opposite direction that the first carriage 58 translates). The second carriage 88 then translates the second plunger 80 from a more distal location to a more proximal location, pulling the second plunger 80 through the second delivery chamber 78, and drawing fluid from the storage chamber (e.g., reservoir) 20 through the second chamber delivery port and into the distal end of the second delivery chamber 78. As explained in more detail below, when the timing belt pulley 120 changes the direction of rotation from clockwise to counterclockwise, the situation is reversed and the second delivery chamber 78 expels fluid while the first delivery chamber 58 fills with fluid. FIG. 3D shows a partial perspective view of the proximal end of the device 4 shown in FIG. 1A. FIG. 3D also shows in more detail the first carriage 68 operatively connected to the timing belt 118 and the head 74 of the first plunger 60 received (attached) to a mating slot 76 in the first carriage 68 so that movement of the timing belt 118 translates both the first carriage 68 and the first plunger 60. Similarly, FIG. 3D also shows the second carriage 88 operatively connected to the timing belt 118 and the head 94 of the second plunger 80 received (attached) to a mating slot 96 to the second carriage 88 so that movement of the timing belt 118 translates both the second carriage 88 and the second plunger 80. In this example, the proximal end of the first carriage 68 and second carriage 88 abut the pulley mount 122, stopping proximal movement of the first carriage 68 and second carriage 88 and preventing the first plunger 60 and the second plunger 80 from moving out of their respective first and second delivery chambers 58, 78, although other methods of stopping proximal translation of the first plunger 60 and the second plunger 80 are also contemplated.

Figure 3F:
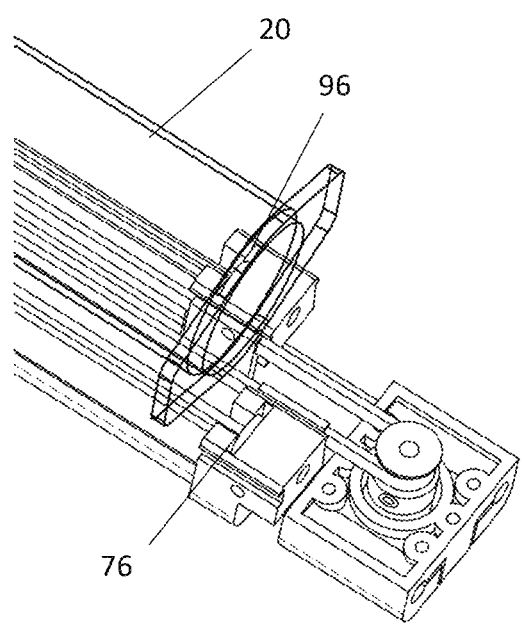
FIG. 3F shows a partial end view of the proximal part of the of the injection apparatus shown in FIG. 3E.
Figure 3G:
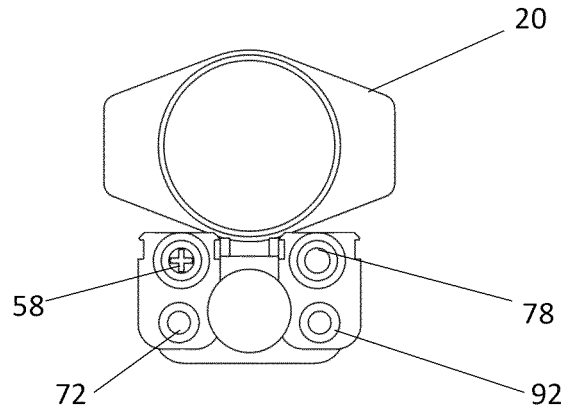
FIG. 3G shows a rear view of the proximal part of the of the injection apparatus shown in FIG. 3E.

FIG. 3G shows a proximal partially perspective view of the device 4 with plunger 52 of the storage chamber (e.g., reservoir) 20 and other components removed. FIG. 3F shows the first delivery chamber 58 and the first guide 72 as well as the second delivery chamber 78 and second guide 92. FIG. 3E also shows the timing belt 118 extending into the plane.

Figure 3H:
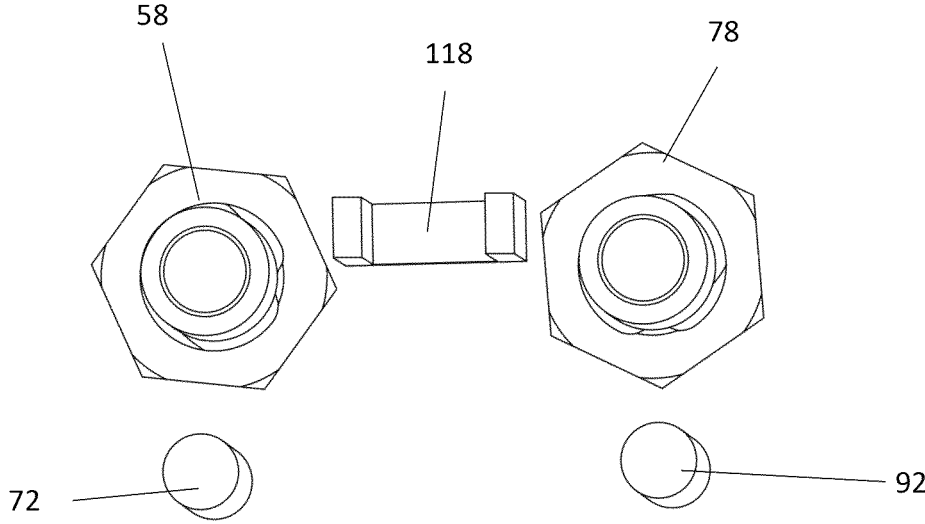
FIG. 3H shows a partial perspective view of the proximal part of the of the injection apparatus.

FIG. 3H shows a top perspective view of a first carriage 68 or second carriage 88. The first carriage 68 and second carriage 88 are shown as the identical in this example, although they do not need to be identical. FIG. 3I shows a side perspective view of the carriage shown in FIG. 3H with the carriage rotated so the view is proximal. FIG. 3H and FIG. 3I show the first carriage channel 70 (or second carriage channel 90) for receiving the first shaft guide 72 (or second shaft guide 92) as shown in FIG. 3J. The first guide shaft 72 and second guide shaft 92 are shown as extending longitudinally and substantially straight in this example, although other examples are contemplated. The first guide shaft 72 and second guide shaft 92 fit inside the first carriage channel 70 and second carriage channel 90 and are together configured so that the first guide shaft 72 and second guide shaft 92 fit inside the first carriage channel 70 and second carriage channel 90 move relative to one another. An outer cross-sectional shape of the guide shaft and an inner cross-sectional shape of the carriage channel may be circular, oval, ovoid, and triangular. FIG. 3K shows a bottom side perspective view of the device 4 with the housing and some other components removed. FIG. 3K shows part of the device transmission. FIG. 3K shows the motor 116 and the battery 104 for providing power to the motor 116. FIG. 3K also shows the second pulley 114 attached to the motor 116. The distal portion of the timing belt 118 is tensioned around the second pulley 114. Rotation of the motor 116 in one direction drives the pulley to rotate and activates the transmission, moving the first plunger 60 and the second plunger 80, filling the first delivery chamber 58 with fluid from the storage chamber 20, while expelling fluid from the second delivery chamber 78. Reversing the direction of rotation of second pulley 114 reverses the actions, expelling fluid from the first delivery chamber 58 while filling the second delivery chamber 78 with fluid from the storage chamber 20.

Figure 4A:
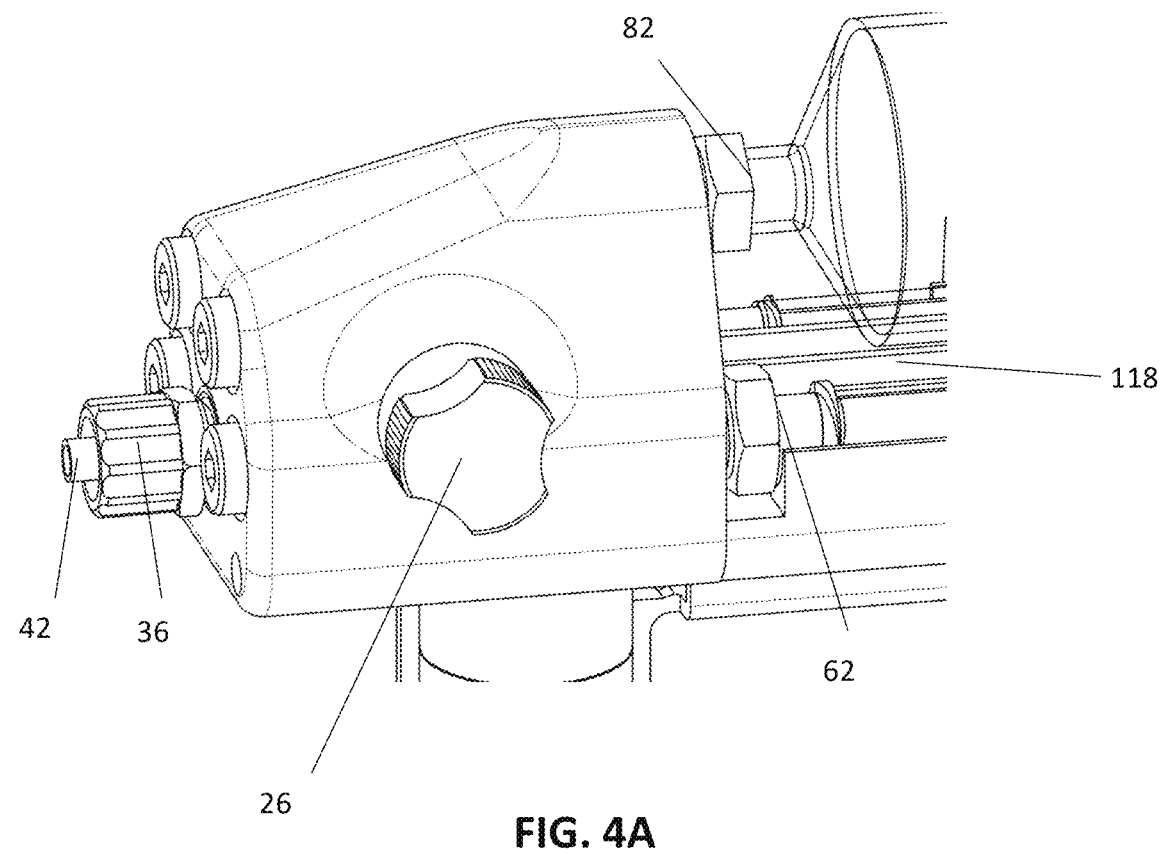
FIG. 4A shows a side perspective view of an example of an injection apparatus.
Figure 4B:
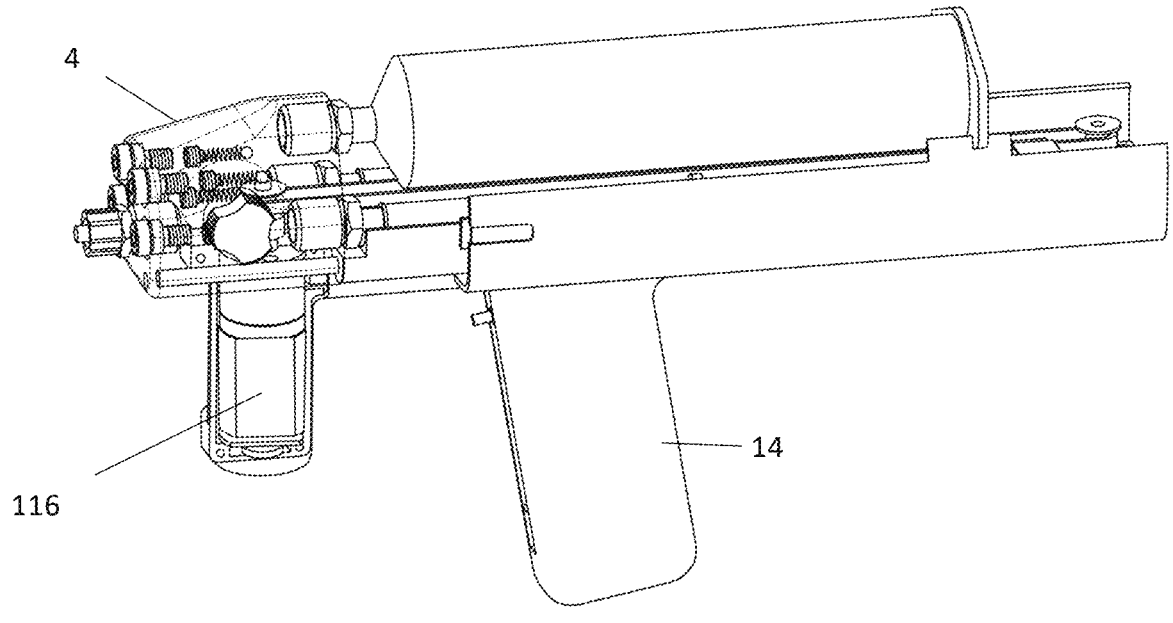
FIG. 4B shows a partial side perspective view of part of the fluid transfer system of the injection apparatus shown in FIG. 4A.
Figure 4C:
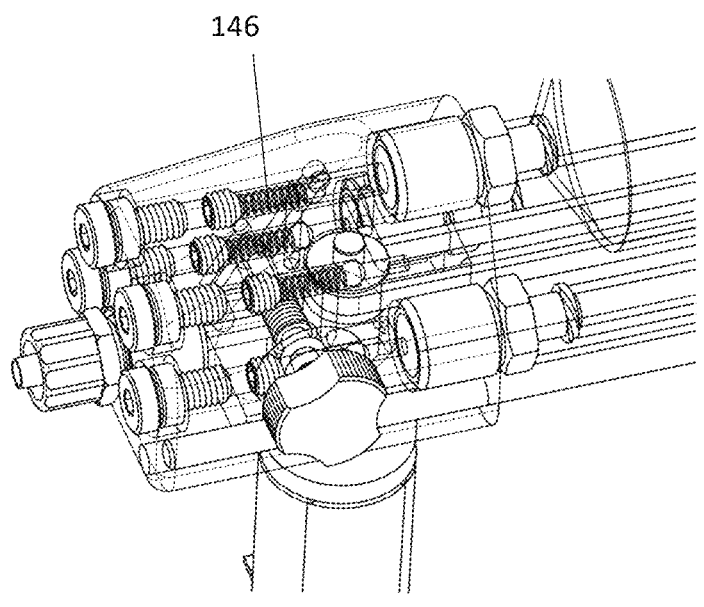
FIG. 4C shows a partial side perspective view of part of the distal part of the fluid transfer system of the injection apparatus shown in FIG. 4A.
Figure 4D:
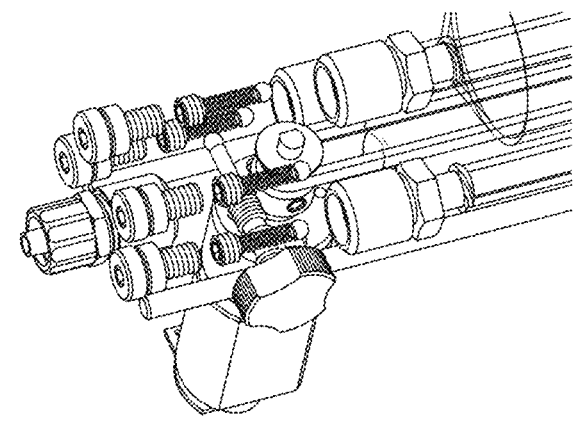
FIG. 4D shows a partial side perspective view of part of the distal part of the fluid transfer system of the injection apparatus shown in FIG. 4A with the internal manifold piping removed.
Figure 4E:
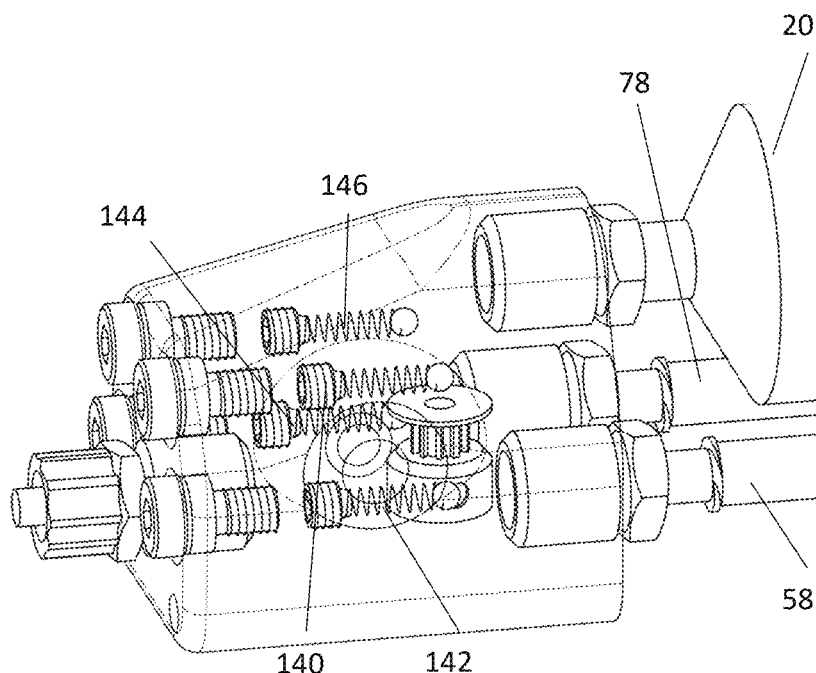
FIG. 4E shows a partial side perspective view of part of the distal part of the fluid transfer system of the injection device shown in FIG. 1A with the internal manifold piping removed.
Figure 4F:
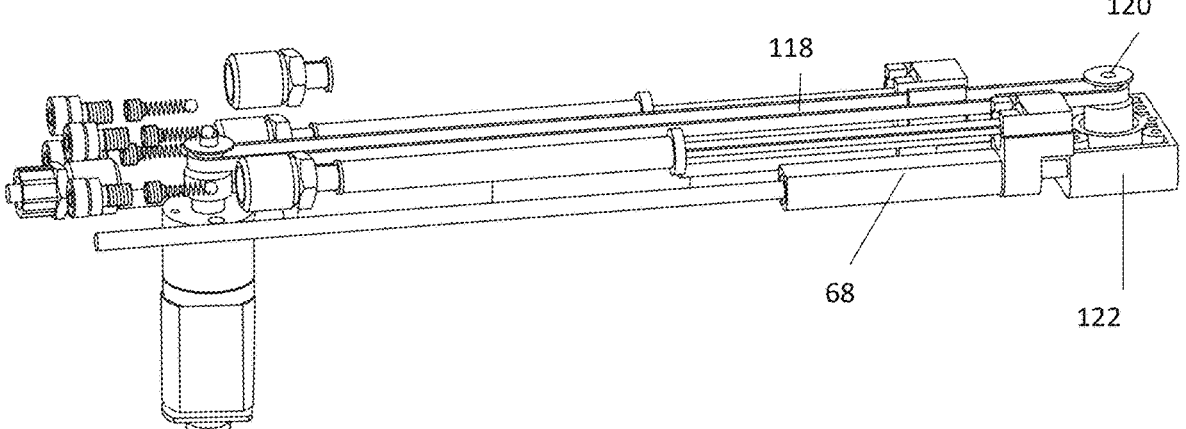
FIG. 4F shows a partial side perspective view of part of the distal part of the fluid transfer system of the injection apparatus shown in FIG. 4A with the fluid transfer manifold piping removed.

FIG. 4A-FIG. 4G show parts of the fluid transfer system of the device 4. FIG. 4A shows a side perspective view of the head region 12, which contains much of the fluid transfer system. FIG. 4B a shows partial side perspective views of part of the fluid transfer system and FIG. 4C shows a closer up view of the head region 12 with the head region housing transparent. FIG. 4B-FIG. 4E, show a first valve 140, a second valve 142, a third valve 144, and a fourth valve 146 in the fluid transfer manifold 44. In some examples another valve (not visible here) may be included for aspiration, as described below. These valves may be, e.g., PTFE ball valves. Thus, in some examples, five conical seats and balls (valves) may be present in the hydraulic head.

The first valve 140 is in the fluidic pathway between the storage chamber 20 and both the first delivery chamber 58 and the second delivery chamber 78. The second valve 142 is in the fluidic pathway between the first delivery chamber 58 and the delivery port 42. The third valve 144 is in the fluidic pathway between the second delivery chamber 78 and the delivery port 42. While the first delivery chamber 58 is expelling its fluid payload to the delivery port 42 (and the patient through a delivery element), the second delivery chamber 78 is filling with fluid from the storage chamber 20; the first valve 140 is open, and fluid flows from first delivery chamber 58 to the delivery port 42. As fluid is pulled into the second delivery chamber 78 from the storage chamber 20 by the pull from the second plunger 80 being withdrawn (by the rotating transmission system), the second valve 142 closes. The first valve 140, the second valve 142, the third valve 144, and the fourth valve 146 may be, for example, one way check valves or other automatic valves. In preparation for using a device 4, the device may be primed. If a device does not already have delivery chambers and/or storage chambers, delivery chambers and/or storage chambers may be loaded or attached to the device. The plunger 52 of the storage chamber 20 may be pushed to load fluid into the first delivery chamber 58 and/or second delivery chamber 78 to prime the device. Some examples include the step of priming (e.g., manually priming or with a trigger) the first delivery chamber 58 or priming (manually priming) the second delivery chamber 78. Once primed, atmospheric pressure on the storage chamber 20 (e.g., syringe or tubing) fills the first delivery chamber 58 and the second delivery chamber 78 on their intake strokes as the transmission rotates. Pressures from about 5 psi to about 400 psi (e.g., between 5 and 300 psi, between 5 and 250 psi, between 5 and 225 psi, between 5 and 200 psi, etc.) may be generated in the device 4. In some examples, the automatic expulsion device may be configured to deliver fluid with a fluid pressure of at least 5 psi, at least 10 psi, at least 50 psi, at least 100 psi, or at least 150 psi, and/or less than 500 psi, less than 400 psi, less than 300 psi, less than 250 psi, less than 200 psi, less than 150 psi, less than 100 psi or anything between these values. The pressure may be determined anywhere in the device. In some examples, the pressure can be determined in the first delivery chamber 58, the second delivery chamber 78 (if the device has one), or at the tip of a combined storage/delivery chamber (see below). In some particular examples, pressure may be determined at the tip of any of these chambers. Any or all of the first delivery chamber 58, the second delivery chamber 78, and/or the combined storage/delivery chamber may include a pressure sensor for detecting the pressure. The pressure sensor may have a feedback loop to the motor/microcircuit. A delivery element 38 may be a hollow sharp 34 such as a needle, such as from a 20 gauge needle to a 32 gauge needle (e.g., a 21 gauge needle, a 22 gauge needle, a 23 gauge needle, a 25 gauge needle, a 27 gauge needle, a 30 gauge needle, 31 gauge needle, or a 32 gauge needle). In some examples, a larger (lower gauge) needle may be useful for injection into a joint. In some examples, a smaller (higher gauge) needle may be useful for facial injection. Pressure between 5 psi and 500 psi (e.g., between 5 and 400, between 5 and 300, between 5 and 250, between 5 and 200, etc.) may be generated with ~3-5 lbf delivered from the motor (e.g., a geared DC motor) and timing belt. The device may be configured to deliver at least 30 mls fluid, at least 45 mls fluid, at least 60 mls fluid, at least 100 mls, or at least 200 mls fluid or up to 200 mls, up to 100 mls, up to 60 mls, up to 45 ml, up to 30 mls at a given pressure. For any of the examples described herein, the device may be configured to deliver fluid (e.g., through the fluid transfer manifold) at a rate of 0.5 cc/second to 8 cc per second, such as from 1 cc/second to 5 cc/second for a given pressure and volume. A timing belt may be low cost, symmetric, and package well.

Figure 4G:
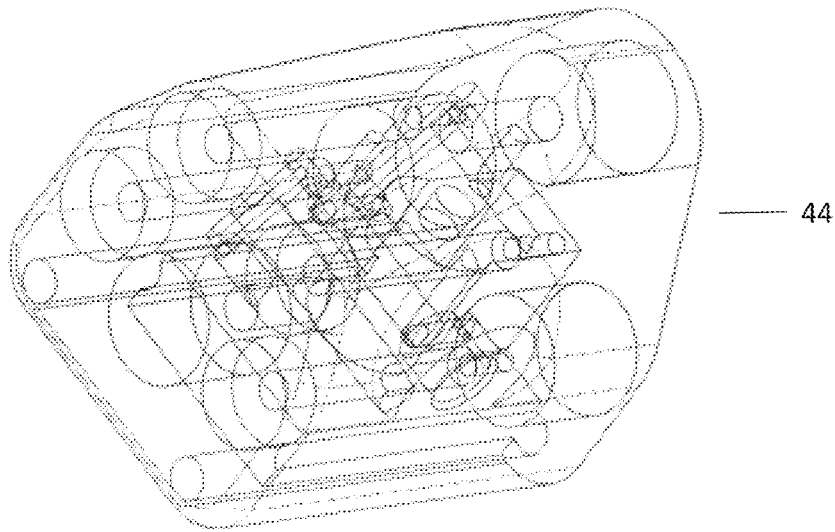
FIG. 4G shows a view of the fluid transfer manifold of the injection apparatus shown in FIG. 4A.

FIG. 4G also shows the fluid transfer manifold 44. The fluid transfer manifold includes a first fluidic pathway connecting the storage chamber 20 to the first delivery chamber 58, a second fluidic pathway connecting the storage chamber 20 to the second delivery chamber pathway 78, a third fluidic pathway connecting the first delivery chamber 58 to the delivery port 42 (and hollow sharp 34 or other delivery element), and a fourth fluidic pathway connecting the second delivery chamber 78 to the delivery port 42 (and hollow sharp 34 or other delivery element). As explained in more detail below, the fluid transfer manifold 44 may also include a fifth fluidic pathway connecting the delivery port 42 (and hollow sharp 34 or other delivery element) to the storage chamber 20. The fluid delivery manifold 44 may be connected to the first delivery chamber 58, the second delivery chamber 78, the storage chamber 20, and the delivery element 38 via Luer lock fittings and the fluid delivery manifold 44 may have three input Luer lock fittings and one output Luer lock fitting.

FIG. 4A-FIG. 4D also show thumb screw 26. Another valve may be in the fluid pathway connecting the storage chamber 20 with the delivery port 42 (and a hollow sharp needle that may be attached to the delivery port 42 and inserted into a patient, not shown in these views) which may be referred to herein as an aspiration pathway. The aspiration pathway may, in some examples, aspirate material, such as a tissue sample, from a patient. The thumb screw 124 can control the operation of the aspiration pathway. The thumb screw 124 controls the operation of the additional (e.g., aspiration) valve. When the thumb screw 124 is rotated in a first direction (e.g., clockwise or counterclockwise), the thumb screw closes the additional valve and fluid cannot flow from the delivery port 42 (or hollow sharp 34 inserted into a patient) to the storage chamber 20. This may close the aspiration pathway. When the thumb screw 124 is rotated in a second direction (e.g. counterclockwise or clockwise, respectively), it may open the aspiration valve and a fluid pathway may be opened between the delivery port 42 (and hollow sharp tip/needle) to the storage chamber 20 (e.g., opened from the delivery port to the storage chamber 20). The aspiration pathway in this configuration is open. Withdrawing the storage chamber plunger 52 in the storage chamber 20 may create a pull or vacuum, and when the sharp tip of the device (e.g., needle) has been inserted into a patient, can draw a sample from the patient in through the hollow sharp needle and into the storage chamber 20. In some examples, a method of operating the device may include determining if the aspirated sample is a blood sample (e.g., from a blood vessel). Determining if the aspirated sample is a blood sample may include the step of inspecting the device (e.g., the storage chamber) for the presence of blood, indicative that the tip of the sharp needle ("sharp") is in a blood vessel. (If fluid is injected from the device into the site, it will be injected into a blood vessel and the fluid will carried away from the local site, rather than having a local effect. Determining may include, for example, visually inspecting the storage chamber by the user to look for the presence of red color in the storage chamber, although other methods (such as use of a light based or sensor) may also or instead be performed. In some examples, it is undesirable to inject the fluid from the device into a blood vessel, and so the user of the device may move the device (e.g., the hollow sharp end of the device) from a first region of the body that is in a blood vessel to a second region of the body to find a body region that is not a blood vessel. Placing the hollow sharp needle (or tip 34) into a second region may include the steps of inserting the hollow sharp needle/tip further into the patient to a second region, partially withdrawing the hollow sharp from the first region of the patient to a second region, or fully withdrawing the hollow sharp needle from the patient, and reinserting the hollow sharp needle into the patient into a second region. The aspiration and visualization process including moving the device may be repeated until it is determined (e.g., automatically and/or manually) that a significant amount of blood is not being withdrawn, indicative that the tip is not located in a blood vessel. It is noted that the distal end of the hollow sharp tip may be placed in a tissue, such as certain dense tissues, and may not aspirate any sample. The absence of a sample upon aspiration may be taken to indicate that the distal tip of the needle is not in a blood vessel. Thus, some examples may include the steps of inserting a hollow sharp tip (needle) into a location in a patient; taking a tissue sample from a patient through a hollow sharp needle; determining if the tissue sample is a blood sample; and removing the hollow sharp needle from the location without expelling fluid from the device if the tissue sample is a blood sample. Some examples may include withdrawing a tissue sample into a storage chamber and/or assaying the sample to detect blood. Some examples may include repeating these steps. In some examples, the device 4 may have a translucent part, a transparent part, and/or a clear part (e.g., window) through which the tissue sample (e.g., blood sample) may be visualized by the user. In some examples, the storage chamber barrel may be translucent, transparent or clear of may have a translucent part, a transparent part, and/or a clear part (e.g., a window). The window may be useful for determining if an aspiration sample is a blood sample. In some examples, the device may be configured so that the plunger 52 of the storage chamber 20 is readily accessible to a device user, and a user may withdraw the plunger 52 a sufficient distance to remove a tissue sample.

Peristaltic Fluid Delivery Systems

Also described herein are peristaltic systems for an injection device for fluid delivery using pressurized fluid to move the fluid through the device. Thus, any of these apparatuses may be configured to operate via peristaltic fluid delivery.

Figure 8:
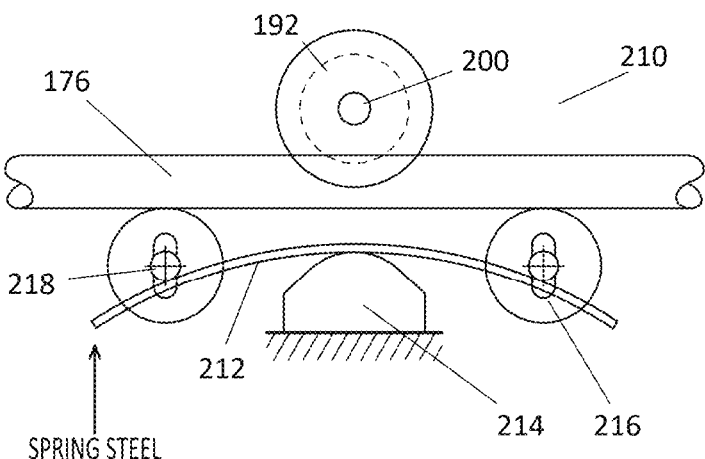
FIG. 8 shows a side schematic of another peristaltic fluid delivery system.
Figure 9:
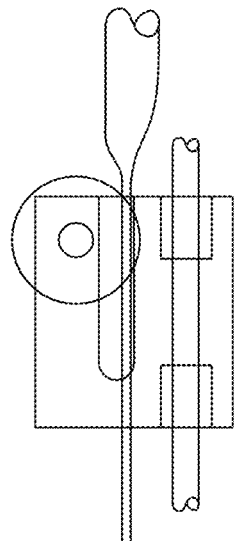
FIG. 9 shows a top view of an apparatus similar to that shown in FIG. 7A-7C.

FIG. 7A-FIG. 7C show an example of part of a peristaltic fluid delivery device 174 for delivering a fluid to a patient. FIG. 7A and FIG. 7B show longitudinal cross-sectional views of parts of the peristaltic fluid delivery device 174. FIG. 7C shows a cross-sectional view of part of the device shown in FIG. 7B. This peristaltic fluid delivery device 174 can be similar to the device 4 described above (e.g., FIG. 1A), and include the same or similar systems and components (e.g., fluid transfer manifold, valves, reservoir, drive system, sensors) and have the same or similar specifications, except that instead of delivery chambers and/or storage chambers being syringes (barrels with plungers) the peristaltic system utilizes fluid filled tubes as delivery chambers for fluid and a compression part to expel the fluid (e.g., instead of a syringe plunger). In some examples, the storage chamber may be a molded part and may be directly connected or directly molded with the fluid transfer manifold. Such directly molding could simplify the device and reduce cost, especially in a disposable or partially disposable device in which the device or parts of the device are not reusable. In some examples, the storage chamber may be located in the handle. FIG. 7A shows the peristaltic fluid delivery device 174 has an elongate first peristaltic delivery chamber 176 having a proximal end 180 and a distal end 182 and a length between. The first peristaltic delivery chamber 176 may be a tubing. The tubing may made from polyether ether ketone (PEEK), polytetrafluoroethylene (PTFE), or another thermoplastic or semi-rigid precision material. The tubing may be configured so it does not diametrically expand under the pressures used (e.g., 3 psi-500 psi, 3 psi-400 psi, 3 psi-300 psi, 3 psi-200 psi, etc.). At the distal end 182 of the first peristaltic delivery chamber 174 is a distal connector 184 configured to connect with the fluid transfer manifold 44 through manifold connector 186, although in some examples the first peristaltic delivery chamber 176 may be directly attached to the manifold connector 186. The distal connector 184 and/or the manifold connector 186 may be a Luer fitting (or part of a Luer fitting) or another suitable fluid fitting, such as a National Pipe Taper (NPT) fitting. The first peristaltic delivery chamber 176 may be connected to the distal connector 184 or the manifold connector 186 by heat shrinking the distal end 182 of the tubing onto the connector. The proximal end 180 may be sealed shut such as by pinching closed and retaining. In some examples, the proximal end 180 is retained in the pulley mount (e.g., pulley mount 122). Similar to as described elsewhere herein, the tubing has a size and diameter to provide a sufficient volume of fluid at a sufficient pressure for delivery to the patient. In some examples, the tubing may be from 1 cm to 25 cm in length, such as from 2 cm to 20 cm or 5 cm to 15 cm. The tubing may be configured to hold at least 0.1 mls, at least 0.5 mls, at least 1.0 ml, at least 2.0 mls, at least 3 mls, at least 4 mls, or at least 5 mls. The tubing may be configured to hold up to 10 mls and to hold any amount between these values, such as to hold from 0.1 mls to 10 mls (10 cc), from 0.5 mls to 5 mls, from 0.5 mls to 3 mls. An inner diameter of the tubing may be less than 20 mm, less than 15 mm, less than 10 mm, or less than 5 mm or larger than 1 mm, larger than 5 mm, larger than 10 mm, larger than 15 mm or anything in between these sizes. The tubing may be from 1 cm to 25 cm in length, such as from 2 cm to 20 cm or 5 cm to 15 cm. In a particular example, the tubing is about 10 cm in length. Although described with reference to the first peristaltic delivery chamber 176 similar to as described elsewhere herein for the device 4, the peristaltic fluid delivery device 174 can have a second peristaltic delivery chamber which is the same or similar to the first peristaltic delivery chamber 176. In some examples, the storage chamber may be a syringe as described elsewhere herein, though in other examples, it may include tubing. A storage chamber (e.g., a storage chamber 20) may include a helper spring to aid in moving a shaft or carriage for filling a first or second delivery chamber. Furthermore the FIG. 7B shows the first peristaltic delivery chamber 176 shown in FIG. 7A with a first delivery tube carriage 190 for controlling fluid flow in and out of the first peristaltic delivery chamber 176. The carriage has a first compression roller 192 and a second compression roller 194 (e.g., a fixed idler roller), which may have a proximal compression roller 196 and a distal compression roller 198. The first compression roller 192 may be a spring loaded compression roller and may include a roller spring 200. FIG. 7B and FIG. 7C also show a shaft 202. The first delivery tube carriage 190 can be connected to the timing belt. The first delivery tube carriage 190 may be configured to move or roll along the shaft 202 from a proximal location to a distal location and from a distal to a proximal location when the timing belt rotates (e.g., oscillates or alternately rotates clockwise and counterclockwise). As the first delivery tube carriage 190 moves or rolls, it successively compresses the tube of the first peristaltic delivery chamber 176 against the shaft 202. The first delivery tube carriage 190 increases pressure inside the tubing, expelling fluid from the tube of the first peristaltic delivery chamber 176 to the delivery port 42 when the first delivery tube carriage 190 is moving distally. The first delivery tube carriage 190 decreases pressure inside the tubing when the first delivery tube carriage 190 is moving proximally, drawing fluid into the tube of the first peristaltic delivery chamber 176 from the storage chamber. These steps may be repeated to repeatedly dispel fluid from one or the other of the first or second delivery chambers to the patient (in the distal pointing direction arrow 204) while filling the other of the first or second delivery chambers (shown by the proximal pointing direction of the arrow 204). In use and as seen in FIG. 7C, the first compression roller 192 and the second compression roller 194 may compress and compress the tubing of the first peristaltic delivery chamber 176. The first compression roller 192 has a roller spring 200 and the roller spring 200 may compress the tube of the first peristaltic delivery chamber between first compression roller 192 and the second compression roller 194 together as the first delivery tube carriage 190 travels distally to expel the fluid or proximally to pull fluid into the tube of first peristaltic delivery chamber 176. The proximal portion of the first peristaltic delivery chamber 176 (tubing) is a collapsed dead volume behind each injection stroke to distal end and when the first delivery tube carriage 190 moves proximally, the first peristaltic delivery chamber 176 (tubing) fills up under atmospheric pressure. Although the first compression roller 192 is shown as having a single roller and the second compression roller 194 is shown as having two rollers, any of the rollers could be or include one roller, two rollers, three rollers, or more than three rollers. The shaft 200 may be from 1 mm to 10 mm in diameter, such as from 3 mm to 6 mm in diameter. In some examples, the shaft is about 4 mm in diameter. FIG. 8 shows peristaltic fluid delivery device 210. The device is similar to as described above for peristaltic fluid delivery device 174. FIG. 9 shows another example of a portion of a peristaltic device.

Figure 10A:
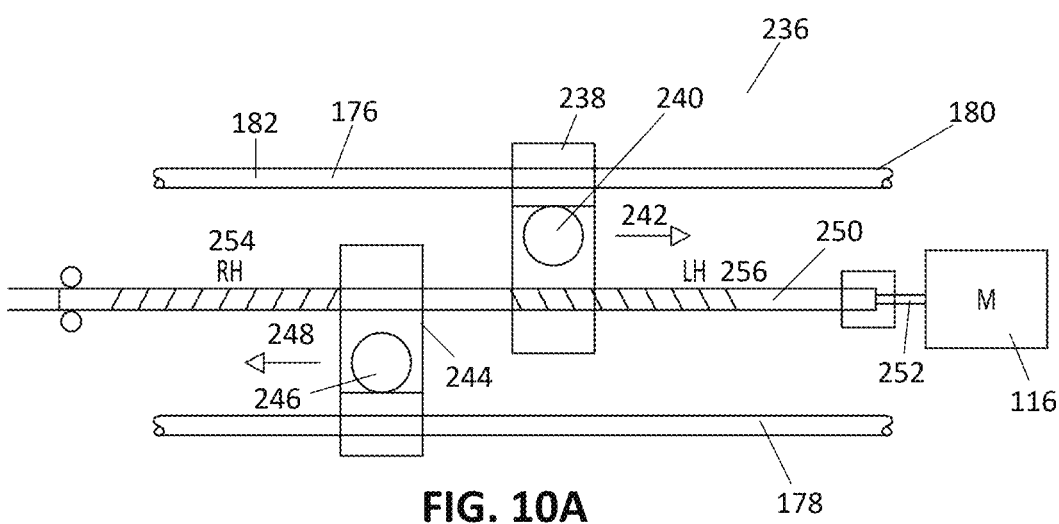
FIG. 10A shows a side schematic of another peristaltic fluid delivery apparatus.
Figure 10B:
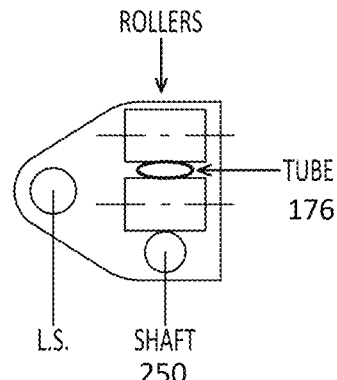
FIG. 10B shows a schematic cross-sectional view of the peristaltic fluid delivery system shown in FIG. 10A.
Figure 10C:
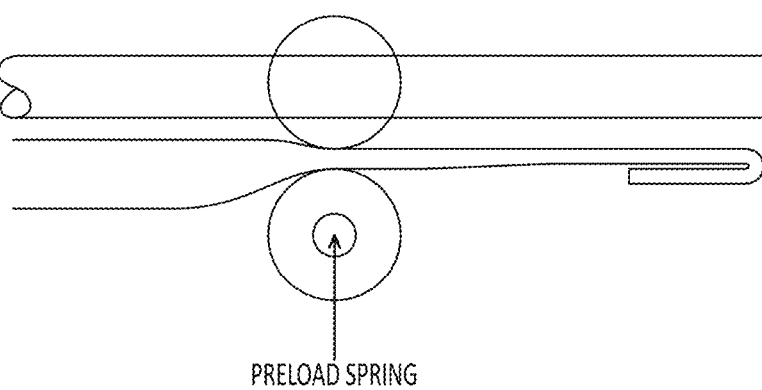
FIG. 10C shows examples of portions of an actuator assembly as described herein.
Figure 11:
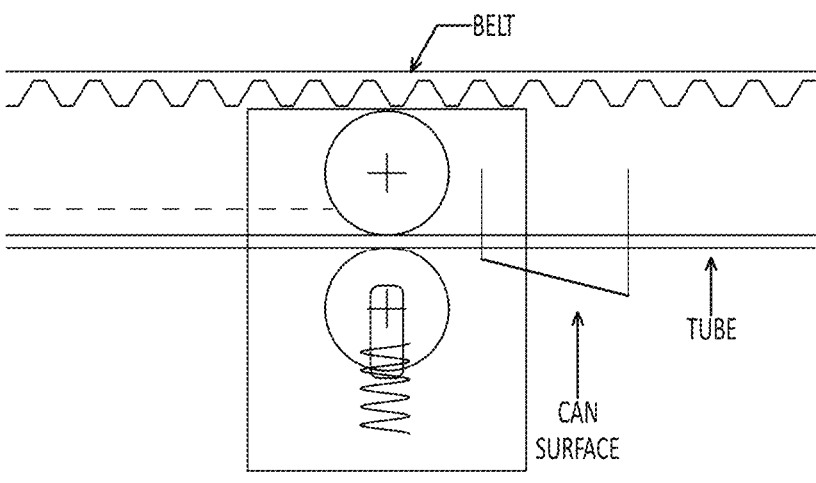
FIG. 11 shows an example of a portion of an actuator assembly (also referred to as a drive assembly) as described herein.

FIG. 10A shows another peristaltic fluid delivery device 236 (e.g., including a drive assembly for such a device). The device is similar to as described above for the peristaltic fluid delivery device 174 except that in this example a lead screw (with a region of right hand threads and a region of left hand threads) is used to simultaneously move/translate both the carriages. With the use of a worm gear, the motor is located proximally in the device. A proximally located motor may eliminate interference with a patient in soft tissue procedures. A proximally located motor may also streamline the volume of the device, creating a more ergonomic device for some applications. FIG. 10A shows the first peristaltic delivery chamber 176 (tubing) with a first lead screw carriage 238 and second peristaltic delivery chamber 178 (tubing) with a second lead screw carriage 240. FIG. 10A also shows lead screw shaft 250 or worm screw with right hand threads 254 and left hand threads 256. The first lead screw carriage 238 is configured to mate with the left hand threads 256 and the second lead screw carriage 240 is configured to mate with the right hand threads 254. When the motor 116 or worm gear turns the lead screw shaft 250 through hub 252, the lead screw shaft simultaneously moves one of the carriages proximally, expelling its fluid contents and moves the other carriage distally, filling the tubing from the storage chamber (not shown in this view) as described elsewhere herein. FIG. 10B shows a side view of the first peristaltic delivery chamber 176 shown in FIG. 10A (and in FIG. 10C) with the roller. FIG. 11 shows another example of a portion of a drive assembly.

Figure 12A:
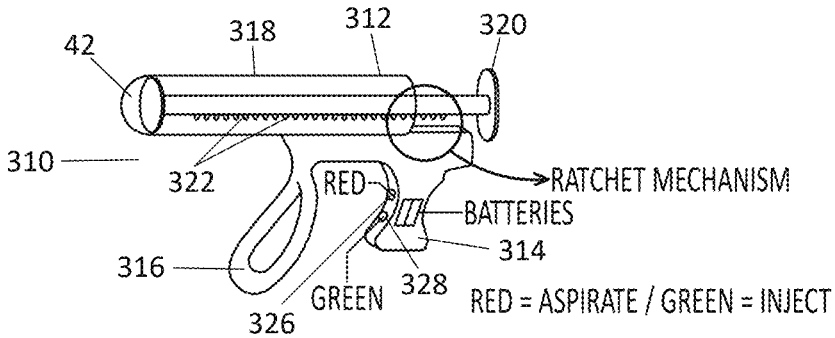
FIG. 12A shows a schematic side perspective view of a fluid delivery (injection) apparatus with a ratchet mechanism.
Figure 12B:
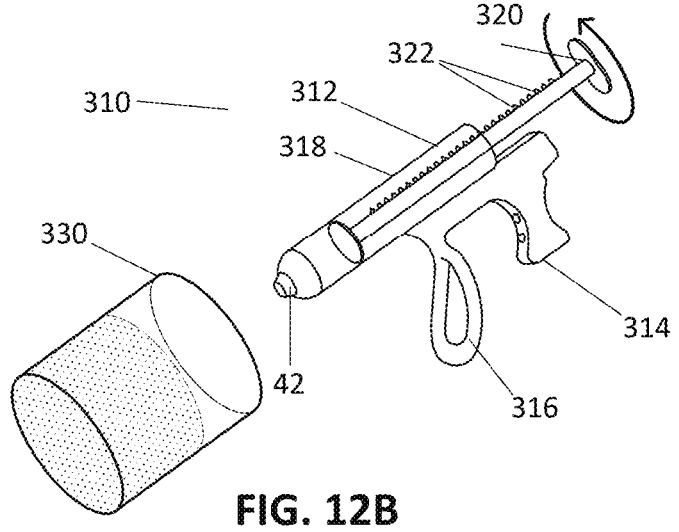
FIG. 12B shows another view of the fluid delivery (injection) apparatus shown in FIG. 12A.
Figure 12C:
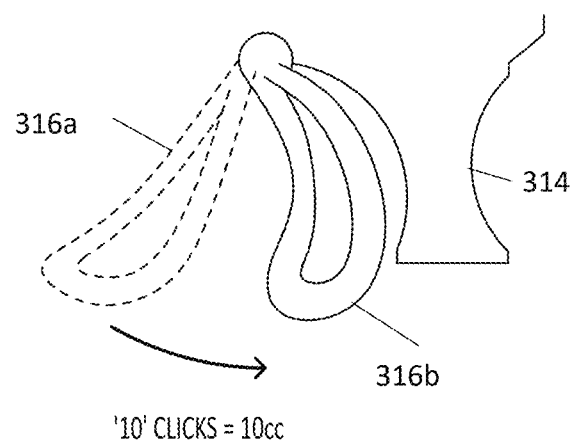
FIG. 12C shows another view of the apparatus shown in FIG. 12A.

FIG. 12A-FIG. 12C show another example of a device, shown as manual device 310, which has a single chamber and maybe manually powered. FIG. 12A shows the device 310 with a fluid delivery chamber 312 with a syringe barrel 318 configured to hold a fluid, a syringe plunger 320 configured to slide within the syringe barrel 318, and teeth 322 of a ratchet system on the underside of the syringe plunger 320. In this example, the teeth 322 run the length of the plunger, though other configurations are possible. FIG. 12A also shows grip 314 with an aspiration control 326 and an expulsion control 328. Activating the aspiration control 326 engages the ratchet, moving the syringe plunger 320 proximally to aspirate a sample (or determine a sample cannot be aspirated) and analyze as described elsewhere herein. Activating the expulsion control 328 engages the ratchet, moving the plunger distally to expel fluid through the delivery port 42 for delivery to a subject.

In FIG. 12B, syringe barrel 318 has been rotated 180° (as indicated by the proximal arrow) to disengage the ratchet mechanism on the syringe plunger 320. Pulling back (proximally) on the syringe plunger 320 will fill the fluid delivery chamber 312 from a source 330 of fluid. FIG. 12C shows pulling the handle and moving the handle from a first position shown as handle 316*a* to a second position shown as handle 316*b*, moves the ratchet a distance to expel 10 cc (10 mls) of fluid from the device 310 to a patient. In this example, each "click" of the handle expels 1 cc (1 ml) though other configurations are possible. However, the relationship between the distance the handle moves (and the number of clicks), controls the amount of fluid expelled so that a controlled dose of a fluid is delivered. For delivery of an opioid or other controlled substance, controlling the dose delivered (or knowing how much is delivered) may be important.

Any of the apparatuses described herein may be reusable or alternatively disposable. In some examples these apparatuses may include a reusable frame that engages with one or more disposable syringes. For example, the example shown in FIGS. 12A-12B may be a semi-disposable unit and may include a reusable frame with a disposable syringe. This example may be manual or battery powered. For example, in some examples, the battery and motor may fit into the handle. The motor may have a toothed gear (e.g., cogwheel) that would interact with the undersurface of the plunger of the syringe (which may also would have a row of teeth/cogs to engage therewith). In some examples, the plunger may or may not need to be rotated to fill the contents of the syringe.

Figure 13:
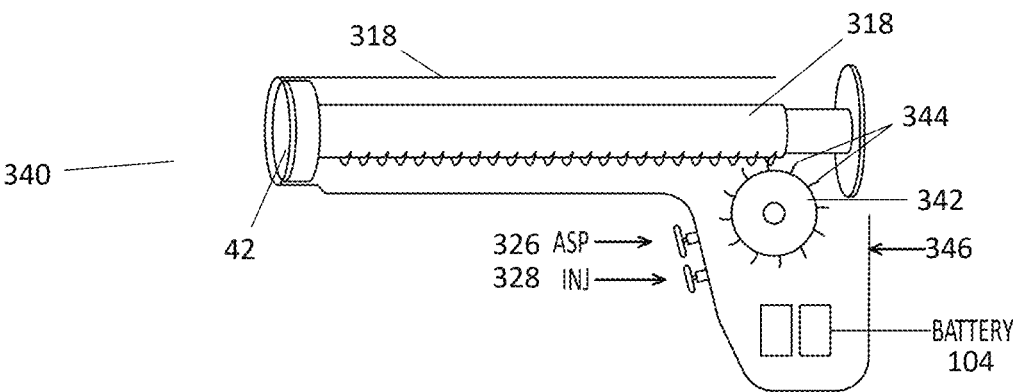
FIG. 13 shows another example of an injection apparatus with a ratchet mechanism.

FIG. 13 show another example of a device, device 340, which has a single chamber for fluid delivery similar to the device shown in FIG. 12A. However, device 340 has a pistol grip 346 with a motor 342 at the top, powered by a battery 104. The motor 342 is controlled by a microcircuit board powered by the battery 104. device 340 has a fluid delivery chamber 312 with a syringe barrel 318 configured to hold a fluid, a syringe plunger 320 configured to slide within syringe barrel 318, and teeth 322 of a ratchet system on the underside of the syringe plunger 320 similar to as shown in FIG. 12A. FIG. 13 also shows motor 342 with mating element 344 configured to mate with teeth 322. Activating the aspiration control 326 rotates the motor in a first direction, engaging the mating element 344 and teeth 322, moving syringe plunger 320 proximally for aspirating a sample from a patient (or determining a sample is not aspirated). The sample can be obtained and analyzed as described elsewhere herein. Activating the expulsion control 328 rotates the motor 342 in a second direction (e.g., opposite direction), engages the ratchet, moving the plunger 320 distally to expel fluid through the delivery port 42 for delivery to a subject. In some examples, the fluid delivery chamber 312 can be filled as described above for FIG. 12B by disengaging the ratchet and drawing the plunger 320 proximally. In some examples, a sample can be aspirated by rotating the plunger 180° to disengage the teeth 322 from the motor 342, and using manual pulling to aspirate fluid. FIG. 21 shows a flow chart of the method of delivering a fluid.

Any of the devices described herein may be configured to be sterilizable, such as by an autoclave and so may include parts that are resistant to heat and/or pressure. Any of the devices described herein may be made to have components that integral, built-in, and disposable so that the whole device is disposable. Any of the devices described herein may have parts that are readily separable such that part of a device is disposable and part is reusable. For example, in some examples, the grip (pistol grip), motor, microcircuit, and/or battery could be reusable and the fluid transfer manifold and first and second delivery chambers are disposable. In some examples, the battery could be a rechargeable battery and the reusable part of the device may be configured so that the battery is available to be recharged. Furthermore, disposable parts may be simple and low cost in order to keep manufacturing costs down. For example, a small timing belt may be low cost, symmetric, and package well. In some examples, part of the device may be removable for separate disposal. For example, a device may be configured to have a readily removable battery so that the battery can be disposed of or recycled separately from the rest of the device.

Fluids

The devices described herein may be used to deliver various fluids, but may be especially useful for delivery of a viscous fluid. Examples of some fluids that may be delivered include abobotulinumtoxinA, an analgesic, articaine, Botox®, botulinum toxin, bupivacaine, calcium hydroxylapatite, collagen, a colloid, dermal filler, dexamethasone, dibucaine, Dysport®, an emulsion, etidocaine, Exparel®, fat, a gel, hyaluronic acid, lidocaine, a liposome encapsulated drug, mepivacaine, onabotulinumtoxinA, poly-L-lactic acid, polymethylmethacrylate (PMMA), prilocaine, procaine, ropivacaine, tetracaine including mixtures and/or salts and/or derivatives thereof. In some particular examples, the automatic expulsion device may be used to deliver a bupivacaine liposome injectable suspension (Exparel®). A fluid as used herein may include a liquid, a suspension. A fluid for delivery with the automatic expulsion device described herein may include particles (microparticles), such as particles with a mean diameter of 0.5 μm to 100 μm, 5 μm to 75 μm, 10 μm to 60 μm, 15 μm to 75 μm, 20 μm to 50 μm.

EXAMPLES

Figure 17:
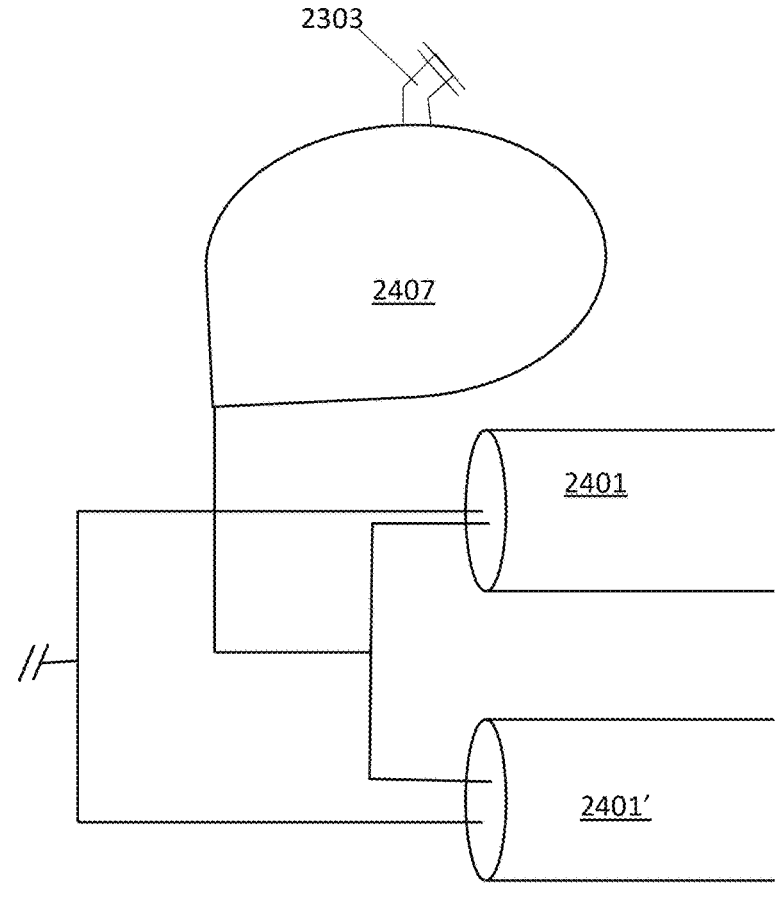
FIG. 17 schematically illustrates another example of a portion of an apparatus as described herein.

FIG. 24 illustrates an example of a storage chamber (e.g., reservoir) and first and second delivery chambers (e.g., first and second piston chambers) that may be used with various examples of the apparatuses described herein. FIG. 17 shows an example in which the storage tank of the apparatus is a tank 2407 that is fluidically connected to a first delivery chamber 2201 and a second delivery chamber 2201' via valved connections, as described and discussed herein. In this example, the tank may include an inlet 2203 in which fluid to be injected may be input. The fluid may be pressurized. Thus in some examples the drive system of the fluid may include a pressurizing subsystem, which may manually or automatically be used to apply and/or remove (e.g., via a one-way pressure release valve 2209) positive pressure within the tank 2207. This pressure may drive or assist in driving fluid from the tank into the delivery chambers, where they may be alternatively used to full and/or deliver material as described above.

In FIG. 17 the storage chamber for holding fluid to be delivered is a pressurized. In this example the storage chamber is a bladder 2407 that can be filled with fluid; the bladder may expand as fluid is filled, pressurizing it. Thus, the bladder may be an elastic material, such as a rubber material or the like. The bladder (also referred to herein as a bag, or a collapsible bag) may be connected via multiple valves to a first delivery chamber 2401 and a second delivery chamber 2401'. The bladder 2407 may alas include an inlet through with fluid and in some examples air or neutral material may be inserted the storage chamber (bladder 2407). Thus, in FIG. 17, the storage chamber may act as a reservoir to hold fluid and feed the alternating smaller volume delivery chambers (e.g., in some examples, 1 cc or 0.5 cc working syringes).

Figure 16:
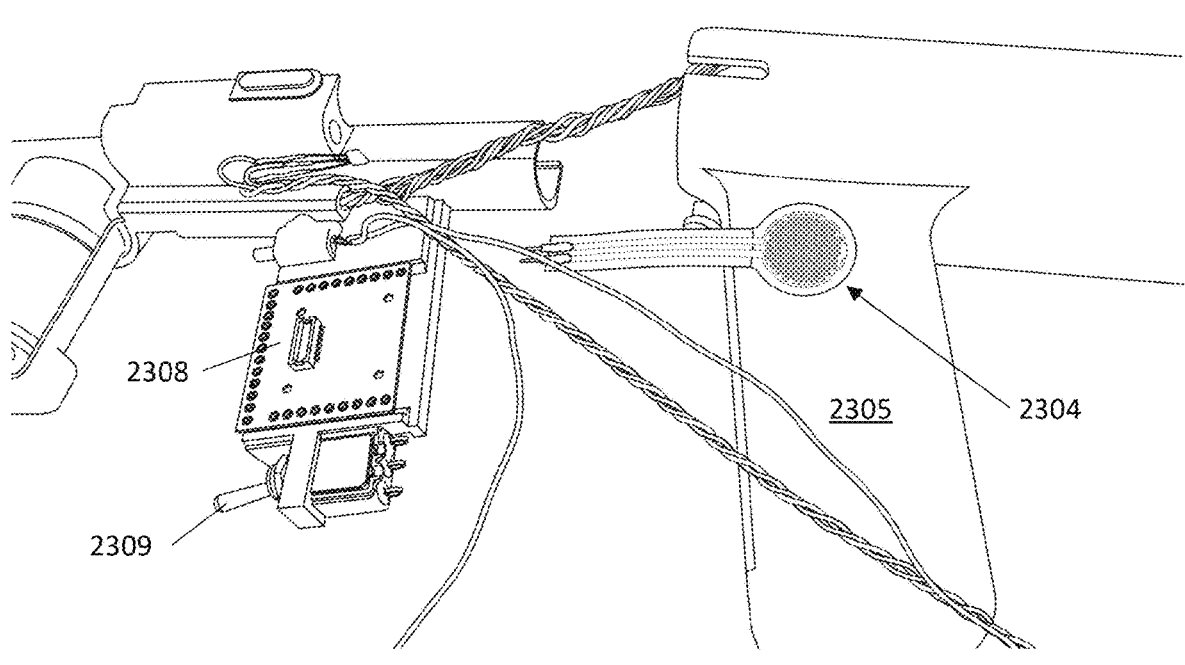
FIG. 16 is an example of a portion of an apparatus including a force sensitive resistor integrated into the handle and configured to adjust the flow rate.

FIG. 16 illustrates an example of an apparatus as described herein including a force sensitive resistor 2304 as part of the handle 2305. The apparatus is shown partially dissembled, showing the connection between the sensor (e.g., force sensitive resistor 2304), control unit 2308 and additional control elements (including switch 2309).

Figure 18A:
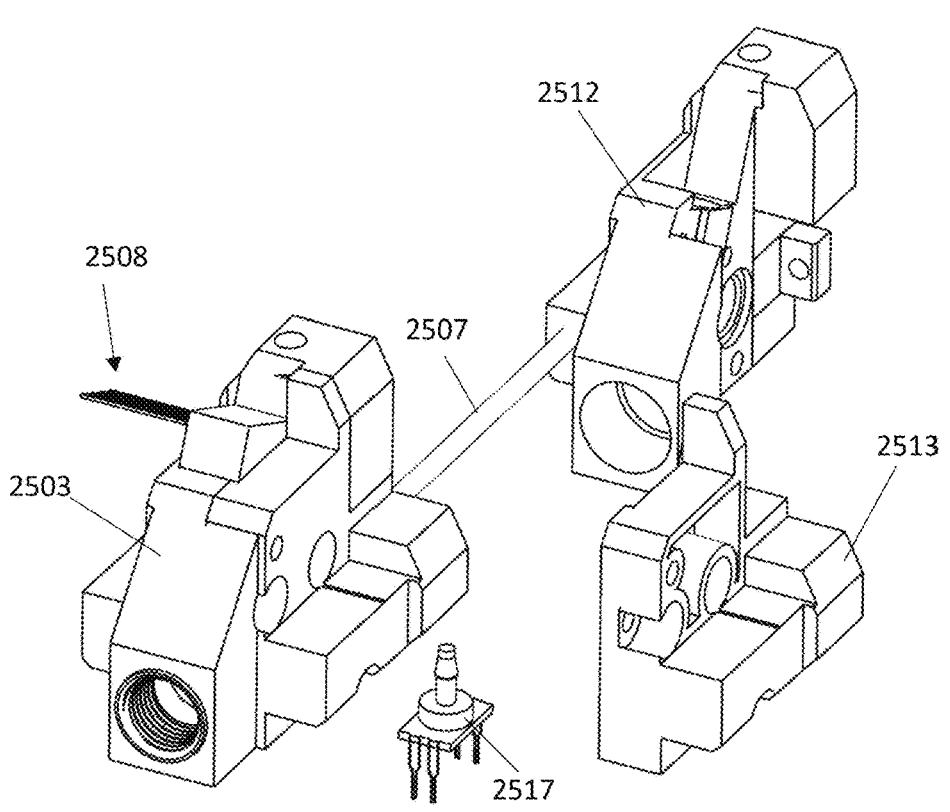
FIGS. 18A-18C illustrate partially exploded views of one example of an apparatus for automatically injecting fluid (including highly viscous fluids) as described herein.
Figure 18B:
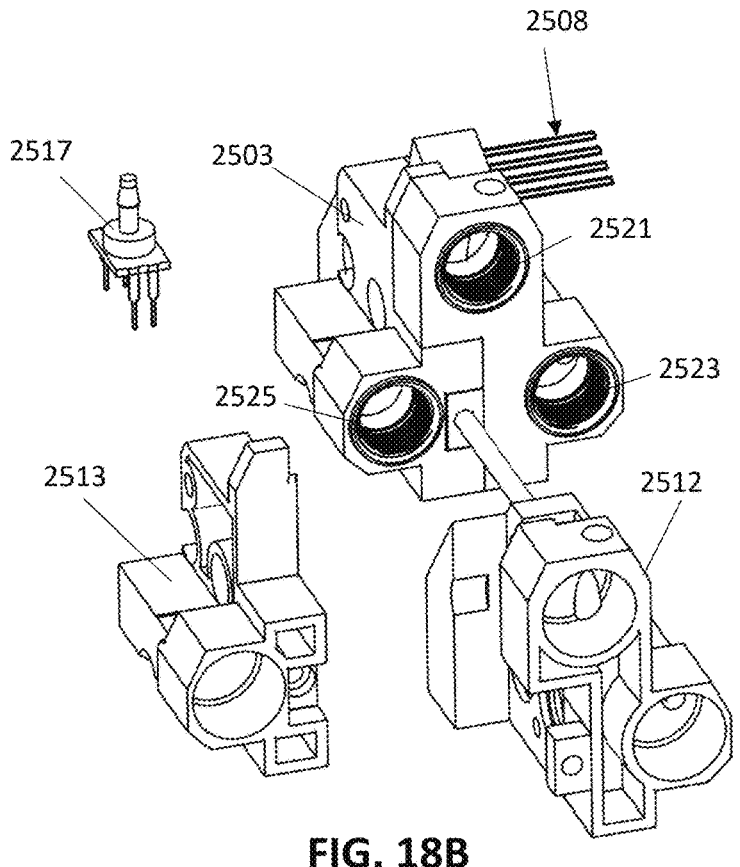
Figure 18C:
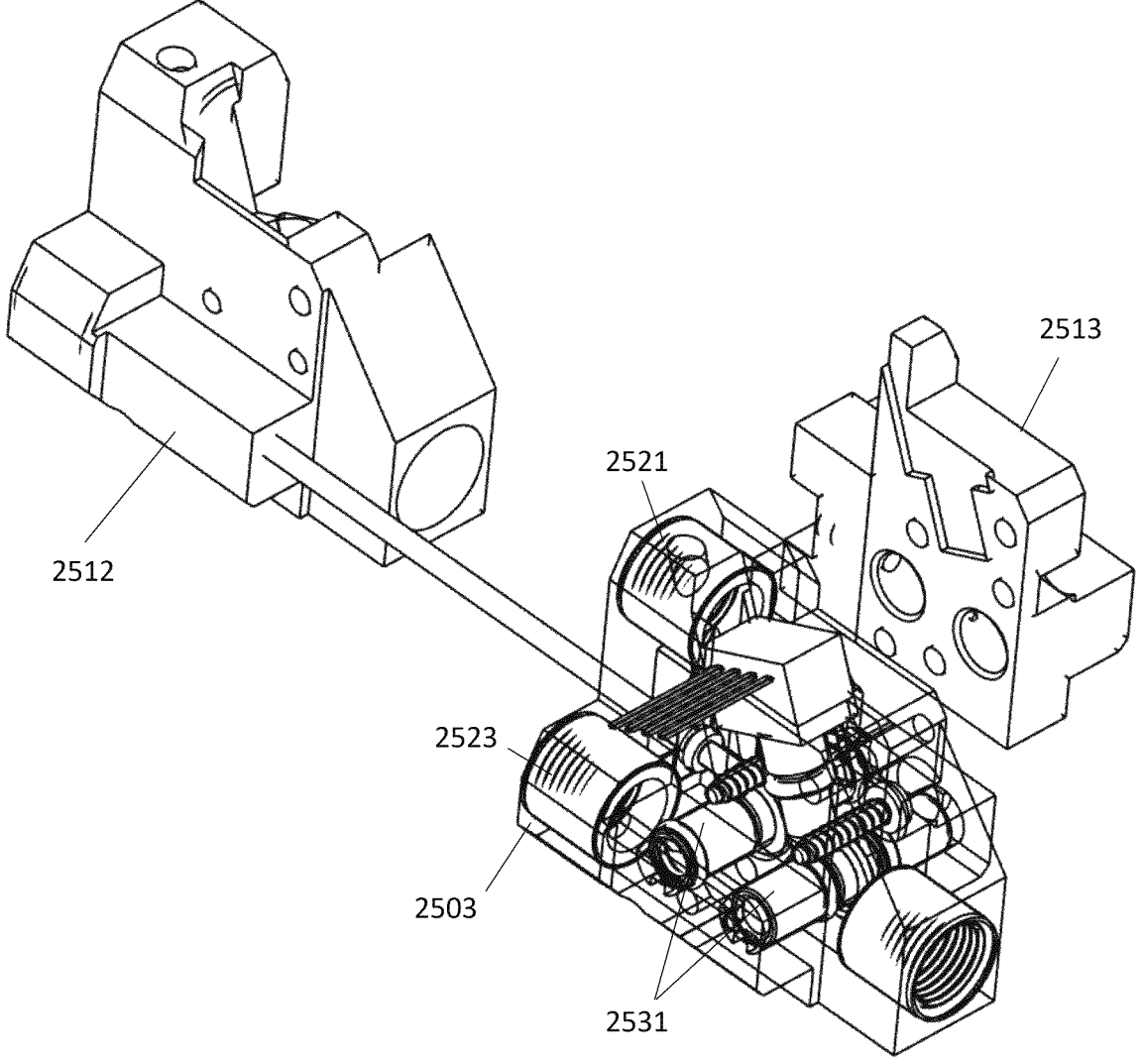

FIGS. 18A-18C illustrate another example of an apparatus, e.g., a device for automatic expulsion of a fluid that is configured to be held in a user's hand. In this example, the apparatus may include off-the-shelf commodity cartridge check valves. The assembly shown in this example is smaller than other examples, and uses injection molded parts. For example, FIG. 18A shows an exploded perspective view of the apparatus, showing a front master housing 2503, a right master housing 2512 and a left master housing 2513. The storage chamber, which may be a housing or bladder as described above, or a larger syringe, as described above, is not shown, but may be connected, e.g., to an upper threaded pipe 2521 within the front housing (as shown in FIG. 18C, in which the front housing 2503 has been made transparent). Similarly, the first delivery chamber and a second delivery chamber are not shown, but may be, e.g., 1 cc or 3 cc (or 5 cc) syringes that may be attached to threaded pipe connections 2523, 2525 on the front housing 2503. These pipe connections may be connected to the cartridge check valves 2531 mentioned above, which may be controlled by an electronics assembly 2508 that is electrically coupled with and controlled by a controller (not shown). The apparatus may also include sensors, additional valves 2518 to connect to the storage chamber and/or the delivery chamber, etc.

In FIGS. 18A-18C, the apparatus includes a rod 2507 that projects from the assembly and acts as aspiration control. This rod may connect to a separate trigger to allowing one hand operation. As mentioned above, in some examples the storage chamber is configured as a bladder (e.g., bladder bag) that may be positioned in the handle of the apparatus. In some examples the storage chamber is a larger chamber (e.g., a 60 cc syringe).

Figure 18D:
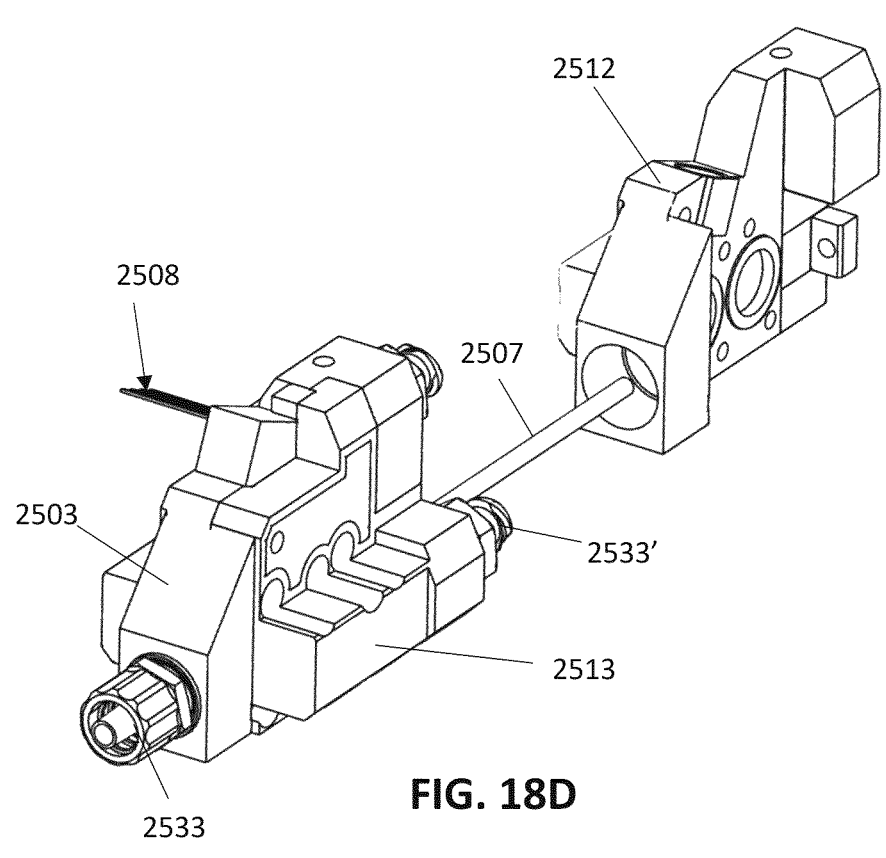
FIGS. 18D and 18E illustrate assembled views of the apparatus shown in FIGS. 18A-18C.
Figure 18E:
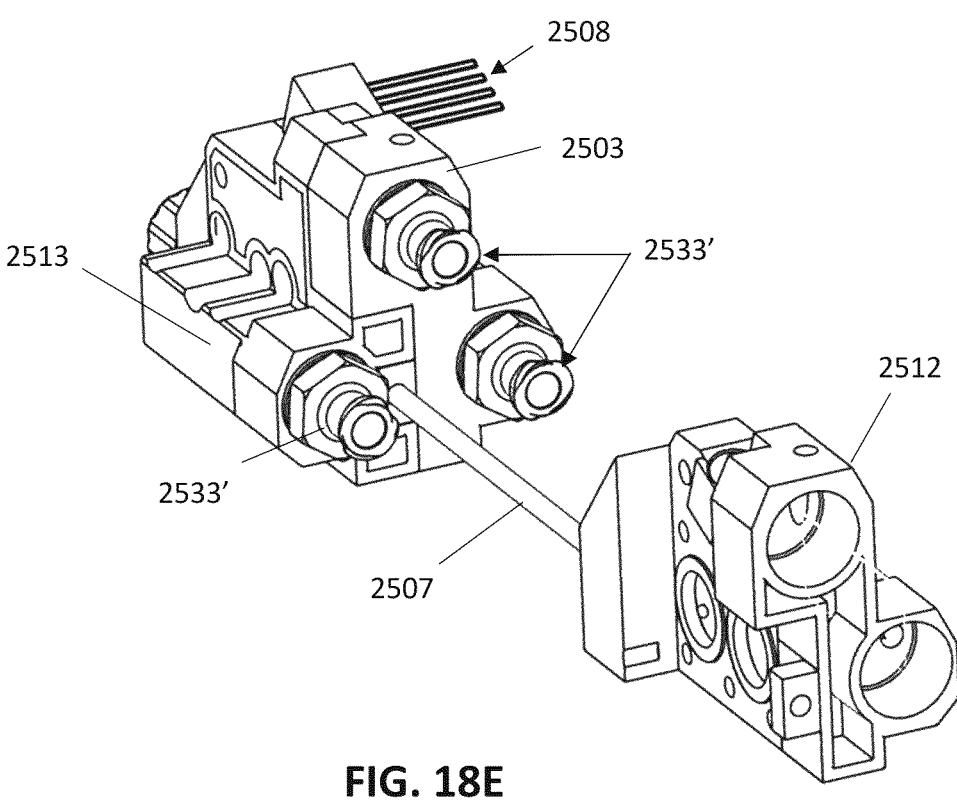

FIG. 18D shows a front perspective view of an (at least partially) assembled view of the apparatus of FIG. 18A-18C showing the front master housing 2503 coupled with the left master housing 2513, and the right master housing 2512 positioned behind the front housing. FIG. 18E shows a back perspective view of the apparatus of FIG. 18D. In FIGS. 18D and 18C, couplings (e.g., plastic quick-turn couplings 2533, 2533' are coupled to the pipe fittings.

Figure 19A:
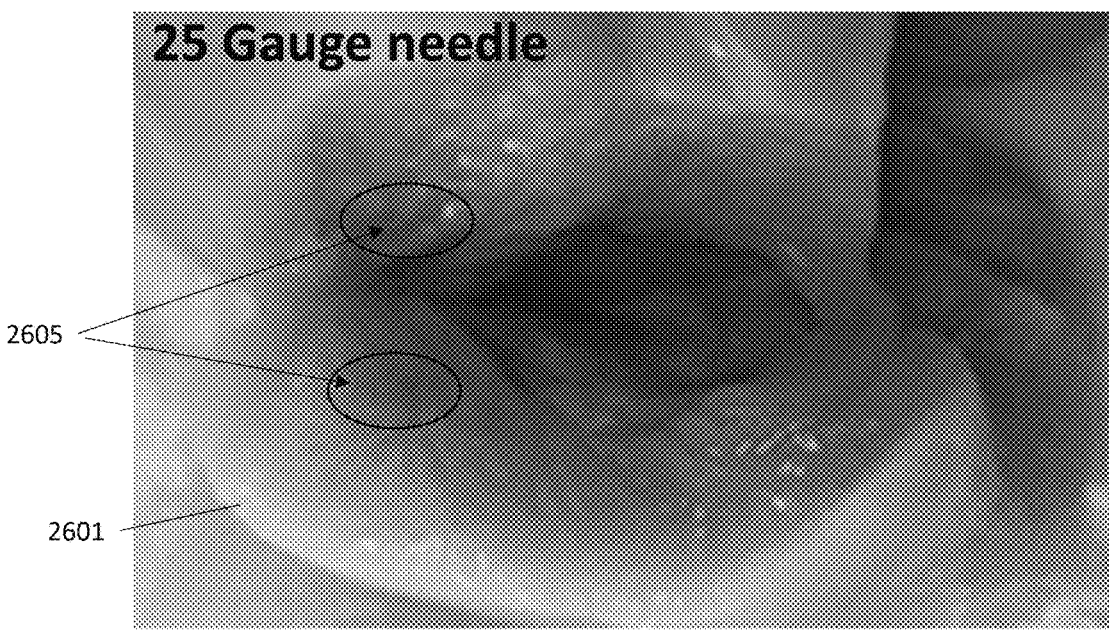
FIGS. 19A-19B illustrate examples of tissue injected with a dye solution using a prototype of one of the apparatuses as described herein.
Figure 19B:
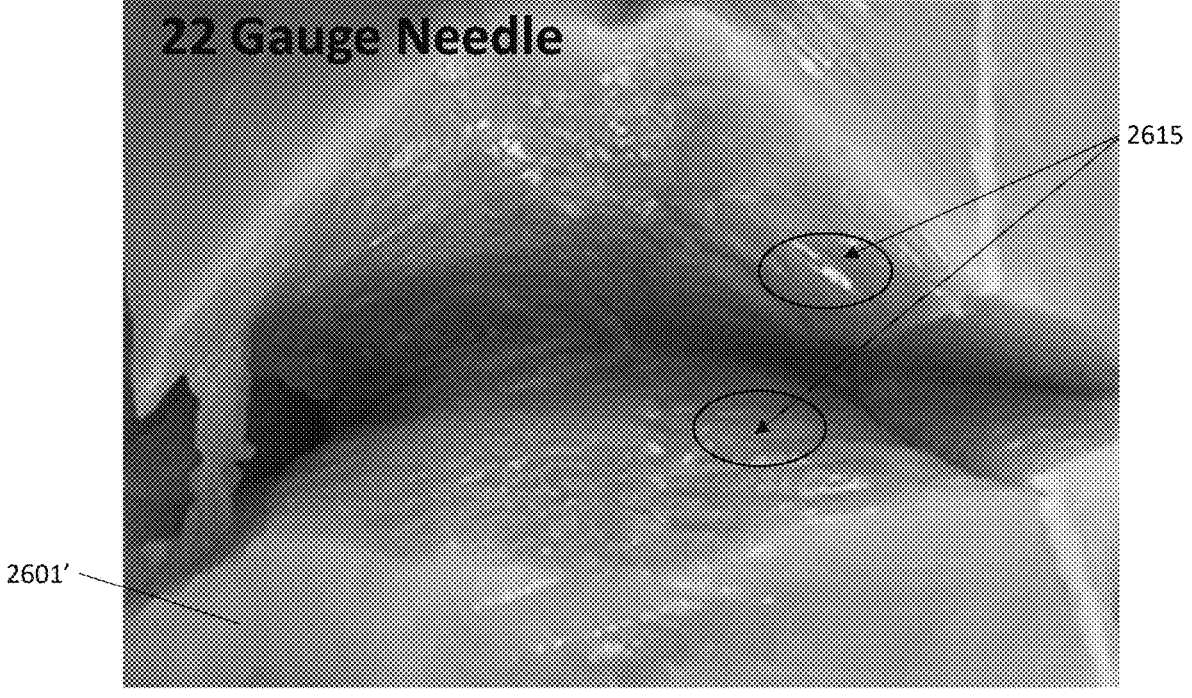

FIG. 19A-19B illustrate the results of the operation of one example of a device as described herein in injecting fluid material into a tissue. In this example, an animal tissue model (e.g., raw chicken breast) was injected with a fluid material, such a highly viscous material, using a battery powered injection device as described above. In this experiment, the apparatus was a battery powered device and included a reciprocating drive (e.g., a pair of pistons each within a piston chamber) coupled to a manifold as described herein. Both 22-gauge and 25-gauge needles were tested with the apparatus. Water mixed with food coloring was injected into uncooked chicken breast 2601. The injection chicken breast was sectioned at the sites of injection performed and examined. The tissue was sectioned along each vertical path. FIG. 19A shows an example of a chicken breast into which the dilute dye solution was injected with a 25 Gauge needle using the prototype device, showing effective dying 2605 of the tissue to the desired depth. During the injection, resistance to the injection of the fluid was minimal. FIG. 19B, shows the results of the animal model (chicken breast 2601') injected with dye 2615 using a 22 Gauge needle on the prototype device. Penetration of injection was excellent with both 22G and 25G needles.

Overall, the example device functioned very well. The device did not stall with injection with either 22 or 25 gauge needle. The tissue was injected multiple times in 2 rows, each row with a different gauge needle (e.g., 22G and 25G). There was no discernable difference between either needles. The syringe did not stall secondary to increased resistance given the gauge difference.

Figure 20A:
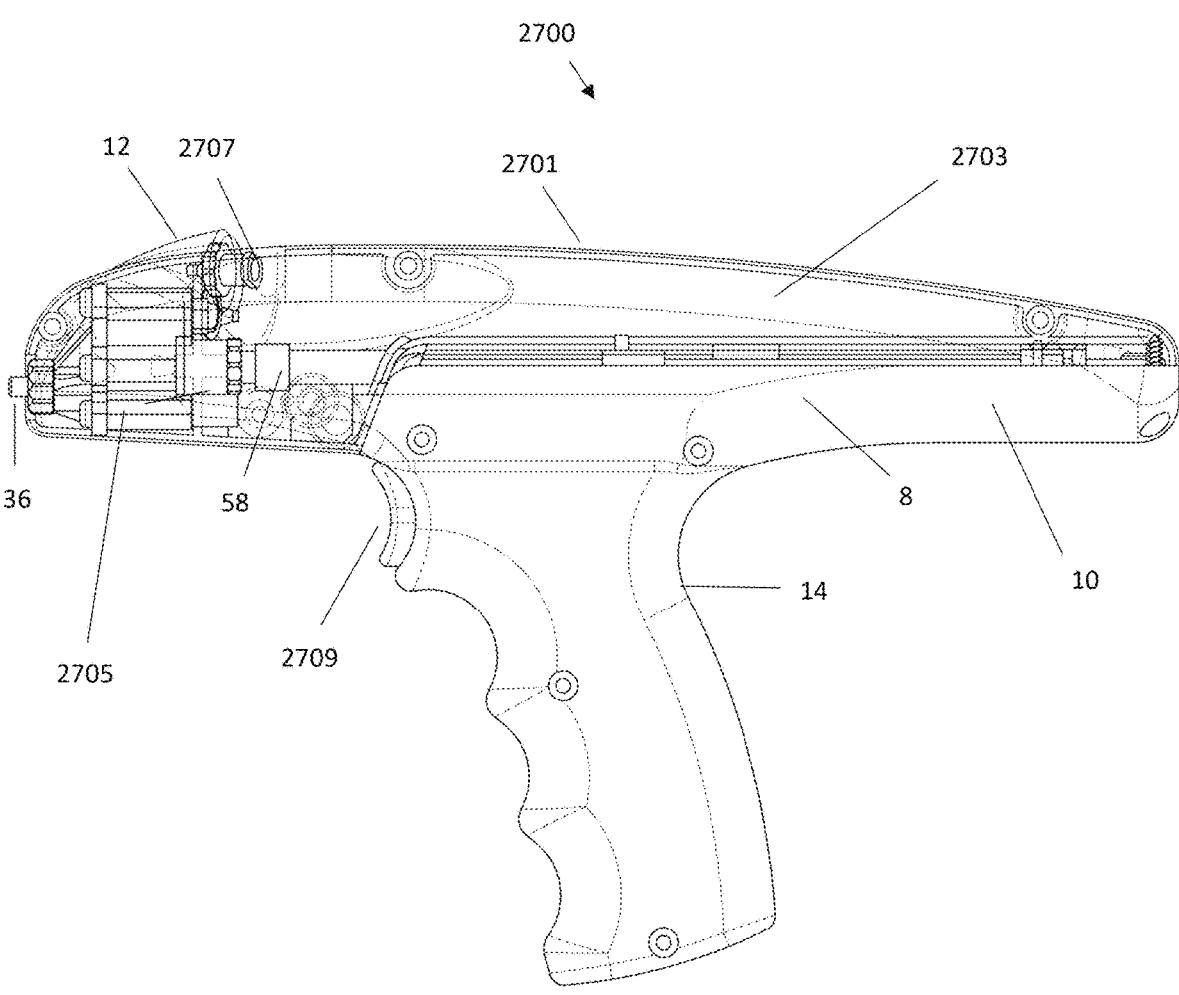
FIG. 20A is a side view of an example of an injection apparatus as described herein.

FIGS. 20A-FIG. 20D show side (FIG. 20A) and side perspective views (FIGS. 20B-20D) of an example of an injection device 2700 for delivering a fluid (e.g., a viscus fluid). FIG. 20A shows a side view of the device 4. The device 4 has a housing 8 (e.g., a first housing), a body region 10, a head (anterior) region 12, and a storage chamber (reservoir) 2703. In this example, the upper portion of the housing is transparent, so that the reservoir, configured as a bag, is visible as are other fluid-handling components including the manifold 2705 and the drive assembly. The device also includes a trigger control 2709 and a fill port 2707.

Figure 20B:
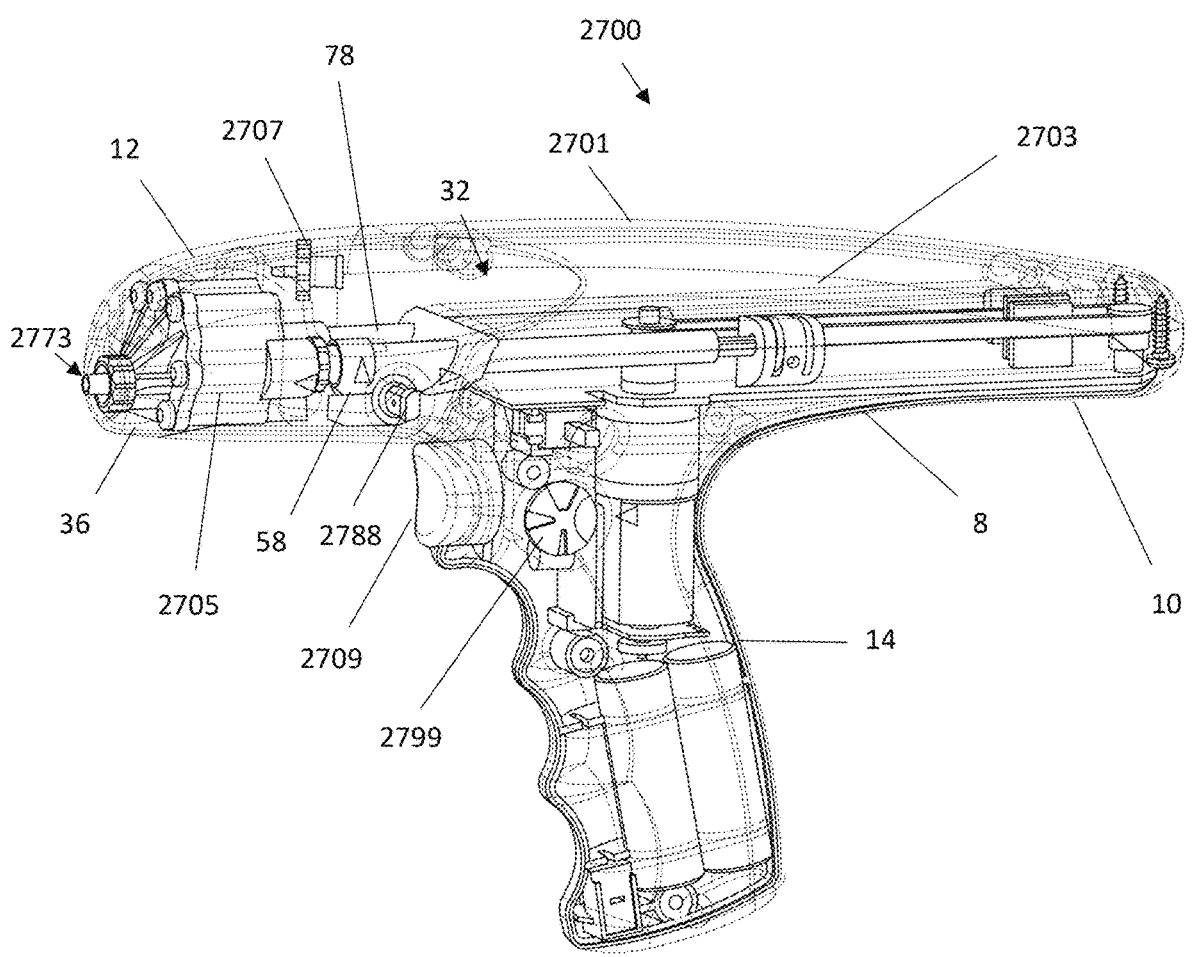
FIGS. 20B-20D illustrate side perspective views of the injection apparatus similar to that of FIG. 20A.
Figure 20C:
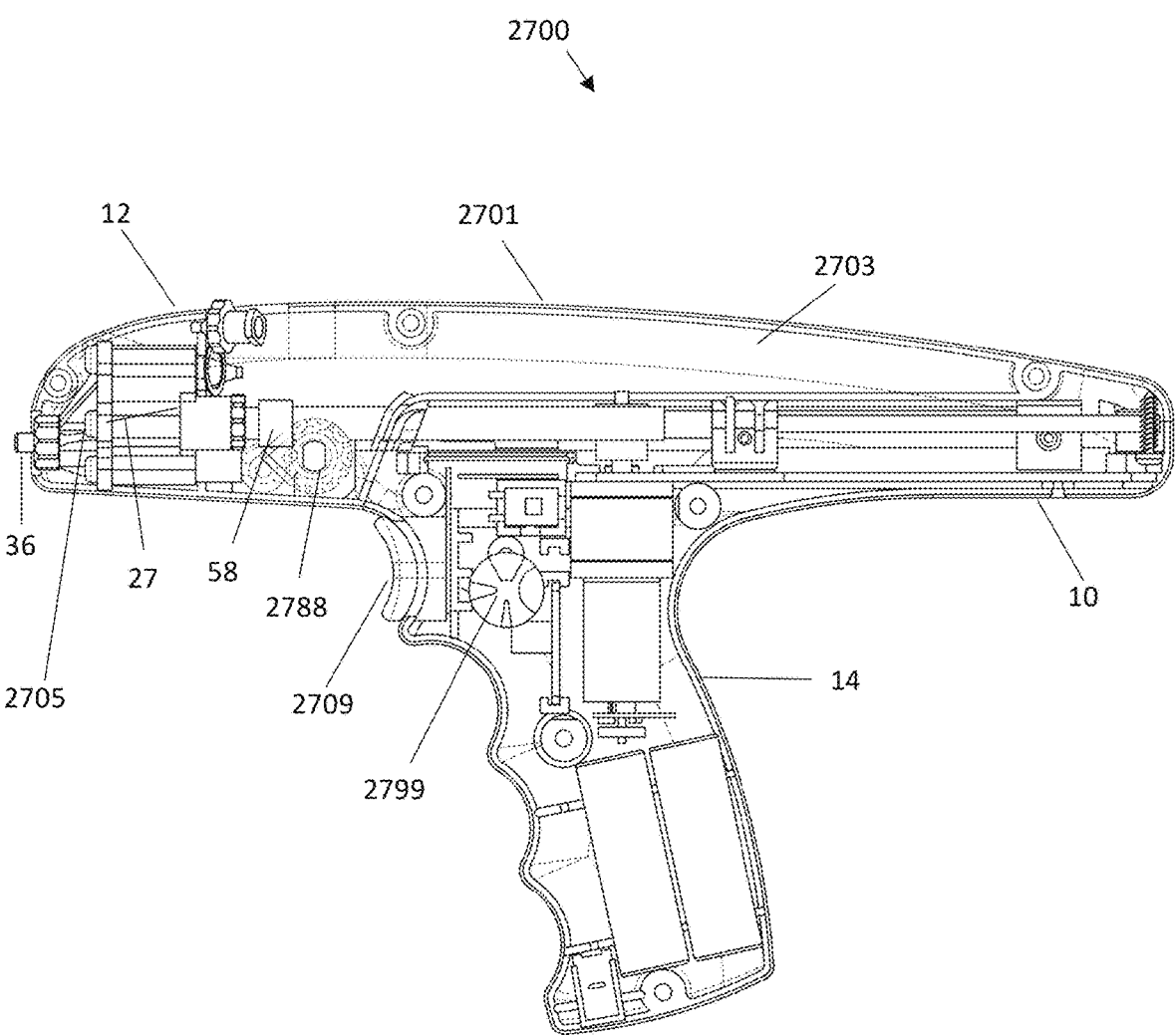
Figure 20D:
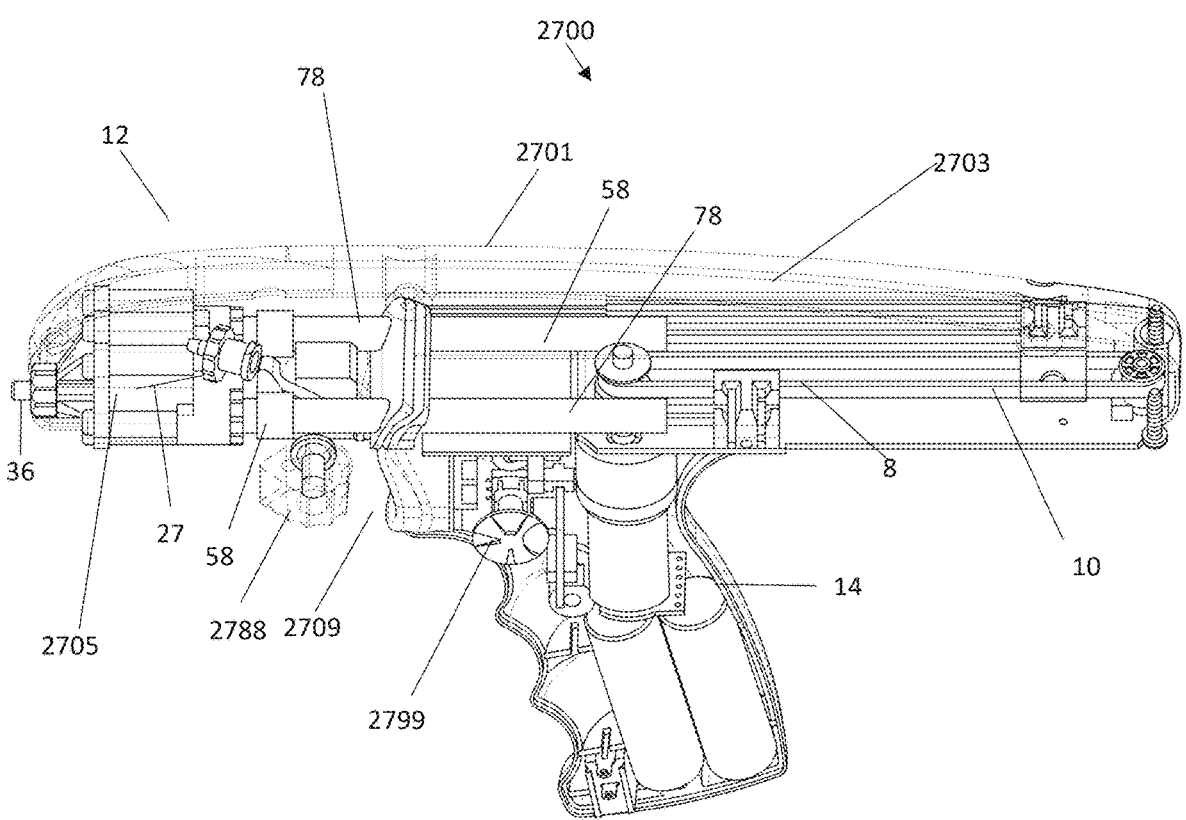

FIG. 20B illustrates a side perspective view of the device 2700 showing the first delivery chamber (first piston chamber) 58. FIG. 20C illustrates another transparent side perspective view of the device 2700 showing the both the first and the second delivery chamber 58 and 78 respectively. FIG. 20D illustrates another transparent side perspective view of the device 2700 showing the both the piston chambers 58 and 78.

The device 2700 is similar to that shown in FIG. 1A. The body region 10 of the device 2700 includes a housing 2701. Within the housing reservoir (configured as a pliable bag 2703), also referred to as a bladder bag, may be filled with a fluid for delivery. The anterior region 12 of the device includes a fluid transfer manifold 2705. In general, the reservoir 2703 may be filled with fluid to be injected into patient's body. The bag 2703 may be refilled via the fill port 2707, and fluidically connects to the two piston chambers 58 and 78 via the manifold and various valves 140, 142, 144, 146. The valves may be check valves (e.g., allowing fluid to pass in one direction but not the opposite direction). The bag 2703 may also be connected through the manifold to a quick turn tube coupling (fill port 2707), which can be opened or closed for filling the bag 2703 with the fluid. The two piston chamber 58 and 78 are configured to be filled with the fluid from the reservoir 2703 in an alternating fashion, so that as the piston is withdrawn from the piston chamber, fluid from the reservoir is drawn into the piston chamber. By alternating the movement of the pistons (e.g., pulling one while pushing the other, and vice versa) the piston chambers may be alternately filled from the reservoir and injected from the injection port 2773. In one example, the two piston chambers 58 and 78 are configured to work in an alternating pattern to take in the fluid from the reservoir 2703 through the fluid transfer manifold 2705 and back out of the manifold and out of the delivery port, using the valves 140, 142, 144, and 146 (not shown). As mentioned, these valves may be check valves. The dispensing of the fluid from the piston chambers 58 and 78 may be accomplished when the manifold is in a first configuration (an injection configuration). A selector (control 2788) on the device may be used to select between the different modes (e.g., fill, inject, aspirate).

In the example shown in FIG. 20B, the device 2700 is configured to operate in these three initial modes namely, fill, aspirate, and inject. The device 2700 can be manually switched into any of the above modes using the selector (e.g., control knob 2711). Before injecting, the reservoir may be filled, e.g., by selecting the fill mode from the selector which may modify the configuration of the manifold (in some cases advancing all or a portion of the manifold, such as a spool within the manifold) to fluidically couple the fill port to the reservoir (e.g., bag). Once filled, the device may be primed, for example by setting the selector (e.g., knob) to inject and running the device for a moment (e.g., while the needle is pointed up) to remove air and move the fluid out through the manifold. In some examples, the device may also or alternatively be operated in an aspiration mode, in which the selector is adjusted to select the aspiration mode in which the manifold is adjusted so that the fill port is in fluid communication with the injection port (delivery port) and not with the piston chambers. In some cases when the device is in the fill and/or aspirate mode the drive assembly may be disabled. In the fill mode, the reservoir may be filled by coupling a source of fluid to the fill port, such as from a larger syringe, that can be added to the reservoir. The opening of the fill port may be larger so that material may be injected quickly and easily. When the selector is set to the injection mode, the piston chambers 58 and 78 can be filled from the fluid from the reservoir.

In the aspiration mode, negative pressure may be applied to the fill port by, e.g., a small (1 cc, 3 cc, 5 cc, etc.) syringe to draw fluid out of the delivery port. Aspiration can be performed to confirm that a needle attached to the delivery port is position in a desired location within the structure being injected, and the material aspirated may be viewed through the walls of the syringe or in some cases sampled using one or more sensors coupled to the fill port.

FIGS. 20B-20D also illustrate a control (e.g., a fluid volume control 2799) configured to select between one or more predetermined delivery volumes and a continuous mode. When the device 2700 is in the inject mode, it may be placed in the continuous inject mode by setting the fluid volume control 2799 to a continuous injection position. In the continuous mode, when the trigger 2709 is pressed, the apparatus will deliver fluid continuously, until the trigger is released (or until it runs out of fluid, and/or an overpressure event or other error event occurs). Alternatively, the fluid volume control may be set to a preset inject mode (e.g., calibrated to inject a predetermined amount, such as 1 cc, 2 cc, 3 cc, 4 cc, 5 cc, 10 cc, etc.) when the trigger is activated. The trigger does not need to be held during delivery of the injected does. After the injection is complete, additional trigger actuation may cause the delivery of another dose. In the example shown in FIGS. 20B-20D, the fluid volume control is a rotary switch (knob) 2799 that may be actuated by the user's finder (e.g., thumb).

Any of these apparatuses may also include circuitry, such as a microcontroller, for controlling the operation of the device. The controller (e.g., control circuitry) may receive inputs from the controls (e.g., the trigger control 2709, the fluid volume control 2799, etc.) and one or more sensors (e.g., pressure sensor, force sensors, etc.). In the example shown in FIGS. 20A-20D, the knob 2799 may communicate with the microcontroller (printed circuit board) or dedicated control circuitry, to set the specific mode and to engage the driver (e.g., motor) to actuate the drive assembly.

In the continuous mode, the fluid may be injected continuously at a rate determined by the controller, in some cases by a dedicated circuit. In any of the preset modes, the fluid may be injected at a fixed rate (and therefore volume) to specifically inject the predetermined amount of the fluid. The fixed rate and the predetermined amount of fluid may be pre-calibrated (e.g., factory calibrated). In some examples the controller may receive input from one or more encoders encoding movement of the drive (e.g., motor) and/or the drive assembly. The controller may determine the volume delivered based on the encoder input. For example, when the apparatus is operating in the injection mode, the piston chambers 58 and 78 have a fixed volume (e.g., 1 cc each, 1.5 cc each, 2 cc each, 2.5 cc each, etc.) and may therefore deliver a metered amount of fluid per stroke. Thus the encoder (sensor 100) may determine the number of full or partial strokes and therefore the volume. For example, a single physical stroke of fluid may relate to a specific number of an encoder counts. Any appropriate encoder and control circuitry may be used to determine, and limit, the volume delivered per actuation.

An encode may be on the motor, the drive assembly (e.g., drive sprocket, gearing, etc.) and/or the idler. In some examples the encoder is on the motor itself, so that rotational movement of the motor may be detected providing a fine control for movement of the drive assembly and therefore the pistons driving fluid injection. In some examples an encoder may not be used, but instead bang-bang control loop may be used to control, e.g. continuous ejection of fluid.

The trigger (trigger control 2709) shown in FIGS. 20A-20D includes a rubber insert. In some examples, the trigger control may be coupled to force and/or pressure sensor. For example, the opposite side of the rubber insert forming the trigger control may be connect to a force/pressure sensing resistor. In one example, the resistance of the pressure sensing resistor may be infinite with no pressure and may reduce to approximately 500 ohms when a pressure is applied. In this way, the apparatus may determine how much force the user is applying to the trigger; this force may be used to adjust the rate of movement of the driver (e.g., motor) and therefore the drive assembly; this may therefore set the flow rate and/or pressure of the fluid delivered from the delivery port.

As mentioned in FIGS. 20A-20C, the reservoir 2703 is a bag or bladder that is collapsible. The bag may expand when filled, and may collapse as it empties. This may prevent the delivery of air (bubbles) by the apparatus. In some examples the apparatus may include an air release or removal portion, such an air-permeable membrane covering an air-venting region in fluid communication with the reservoir and/or manifold (or part of the manifold. As will be described in greater detail below, the apparatus may also include a compression mechanism, such as a compressible foam, to apply pressure against the reservoir so that it collapses when emptying. The compression mechanism (e.g., collapsible foam) may be selected and/or chosen so that the force applied against the reservoir is sufficient to collapse it when emptying, but may still be sufficiently weak so as to allow it to be filled easily (e.g., without requiring so much force that it is too difficult to overcome the pressure applied by the compression mechanism. The bag, the manifold, and the piston chambers may therefore work together as the reservoir is filled so that the collapsed reservoir can expand as fluid fills it and collapses as the fluid is transferred into the manifold and the piston chambers. Thus, in some examples, the compression mechanism is an open-cell foam that may be placed around the bag so that it is under a positive pressure so that the reservoir is collapsed when empty; this may also aid in driving fluid from the reservoir into the manifold. In one example, an open cell foam is positioned underneath the reservoir, so that the reservoir is compressed but can spring back with nearly constant force as it is filled. The foam always a near-constant pressure. The foam may generally have a very low compression set resistance, so that it returns to the initial, fully expanded configuration. Examples of foams may include (but are not limited to) cellular (poly) urethane foams (open cell foams with excellent compression set resistance), and soft/medium density open cell silicone foams.

Any of these apparatuses may also include an indicator, such as an LED indicator, display, etc., to indicate certain safe operating conditions. In some examples the LED may include different color indicators (e.g., green, blue, red, white, etc.) which may correspond to different alters, such as low/no fluid in the reservoir, pressure too high, power on/off, battery low, etc. In some cases, multiple LEDs, which may be labeled, may be present at different locations on the housing.

In some examples, as discussed above, pressure applied on the trigger 2709 in the continuous injection mode may change the injection rate of the fluid. For example, higher pressure applied by the user to the trigger may result in a higher the injection rare and vice versa. The device can be operated at a pressure of 100 psi or higher; in some cases pressure may be limited or prevented from exceeding a pressure limit threshold to prevent harm to tissue when treating a patient. For example, in some cases the output pressure of the apparatus from the delivery port may be limited, e.g., to 600 psi or less, 500 psi or less, 400 psi or less, 300 psi or less, 200 psi or less, 150 psi or less, 100 psi or less, 90 psi or less, 80 psi or less, 70 psi or less, etc. Pressure may be limited by controlling the speed (or rate) of actuating the driver (e.g., motor) and/or the drive assembly that drives the pistons within their respective piston chambers. Pressure may be detected within the manifold, including with a pressure detection chamber as will be described in greater detail below in reference to FIGS. 22A-22C.

In some examples the apparatus may be adapted for use with hydrodissection, e.g., application in which high pressure injection may be used for the treatment of dense connective tissue lesions including rheumatoid nodules, Dupuytren's contracture, and trigger finger. In these cases, the apparatus may be configured to deliver a high pressure between about 200 psi and 600 psi specifically. For example, the apparatus may be configured to deliver a higher pressure output which may be set by a control on the device. The liquid delivered may be saline or other therapeutic liquid (e.g., drug).

An indicator on or associated with the apparatus may be used to indicate conditions such as "fluid low" or "high pressure" as mentioned. For example, a yellow light can indicate that the device low on fluid. or a flashing red color may indicate that the applied pressure (which translates to a the injection rate) exceeds a safe threshold value which can lead to too much tissue resistance. This may signal and prompt the user to remove the device from the tissue and restart.

In operation, the device may first be primed and the trigger pressed. To prime, the device may be loaded (filled), for example, the reservoir may be filled by setting the selector to the fill mode (or confirming that it is already in the fill mode) to place the manifold in the filling configuration, and then attaching a source of fluid to the fill port, such as a 60 cc syringe of fluid material to be injected. With the device in the fill mode, the fill port is connected to the reservoir, which may start out collapsed. The fluid may then be added into the reservoir through the fill port, expanding the reservoir. After filling, the selector may be set to the injection mode, and the device may be primed by aiming it upright (e.g., pointing the delivery port up) which will drive any air bubbles in the manifold and/or reservoir towards the delivery port. In the injection mode, the fluid volume control may optionally be set to continuous delivery mode and the trigger may be pressed to operate the device in continuous mode until fluid flows continuously out of the device (e.g., in a continuous stream).

In some examples, such as that shown in FIGS. 20A-20D, the upper housing (or upper portion of the housing) is transparent, and/or may include one or more windows, allowing a view of the reservoir. This may also allow a clear indication of the remaining fluid volume. In some examples the reservoir may also be transparent and/or opaque, to allow the user to see approximately how much fluid is left. In some examples the controller may be configured to detect the fluid amount in reservoir. A gauge may be included to indicate approximately the amount of fluid within the device and/or the number of injections (e.g., when using in one or more of the discrete dosing modes) remain.

For example, the apparatus may detect the pressure, e.g., in the manifold, which may be used to indicate the amount of fluid (or at least the presence of fluid). For example, if the pressure within the manifold is negative (or approaches zero for examples in which pressure is applied against the reservoir) the reservoir may be empty. A negative pulling pressure (e.g., vacuum) can be detected, indicating no more fluid in the bag.

FIGS. 21A-21D illustrate one example of a manifold that may be used. The manifold, which may also equivalently be referred to herein as a manifold assembly, a plenum, a fluid plenum, or a fluid manifold, may include inputs or connectors to the piston chambers.

For example, in FIGS. 21A-21D, the manifold assembly includes an outer housing 2102 forming the manifold body that encloses the fluid pathways between the fill port 2104 and the piston chambers. The fill port may be integrally formed as part of the manifold assembly or may be separately formed and attached thereto. The manifold assembly also connects to and/or is formed integrally with the delivery port 2108. The delivery port is formed as a Luer lock. Any of the ports described herein may be Luer locks. In this example, the manifold is assembled from a manifold body (manifold housing 2102) and a manifold cover or cap 2110. The manifold cover or cap in this example is attached via a plurality of screws.

Figures 21A, 21B, 21C:
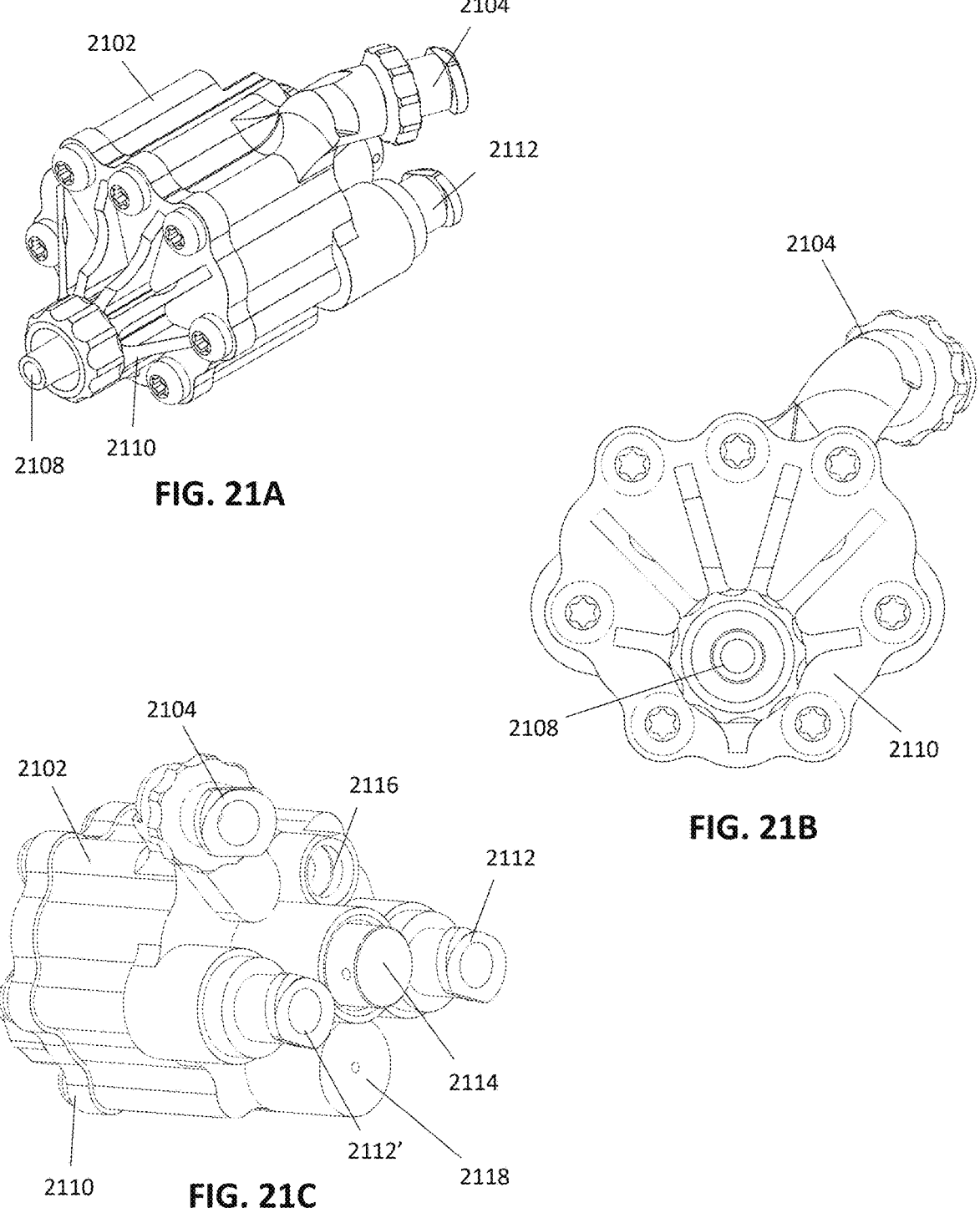
FIGS. 21A-21C illustrate front perspective, front plan and back perspective views, respectively, of one example of a manifold assembly ("manifold") for an injection apparatus as described herein.

Generally two or more piston chambers may be used. Each piston chamber may be connected to the manifold, e.g., via a piston manifold connector 2112, 2112' (as shown in FIG. 21C). The manifold may also include a connector to connect to the reservoir (e.g., reservoir connector 2116). FIG. 21C also shows the spool 2114 that fits into a cylindrical chamber of the manifold. The spool can be displaced relative to the manifold body to change the operational mode of the manifold (e.g., between filling, injecting, and/or aspirating). The manifold may also include a pressure sensing and/or regulating chamber that includes one or more vents 2118.

FIG. 21D is an exploded view of the example manifold shown in FIG. 21D. In general, the manifold assembly may be relatively compact, and appropriately scaled for use in a hand-held, and lightweight injection device as described and shown herein. In this example the manifold has s length (in the proximal-to-distal axis of the injector apparatus) that is between about 2 cm and about 10 cm (e.g., 3 cm or less, 4 cm or less, 5 cm or less, 6 cm or less, between about 4 cm and 6 cm, etc.), and a width this is between 4 cm and 12 cm (e.g., about 4 cm or less, about 5 cm or less, about 6 cm or less, about 7 cm or less, about 8 cm or less, about 9 cm or less, between about 5-10 cm, between about 6-8 cm, etc.).

In the exploded view of FIG. 21D, the manifold body, the manifold assembly includes a plurality of valves 2120, 2120', 2120", which may be check valves, that permit fluid flow in just one direction. The check valves are in fluid communication with the ports for the piston chambers and may allow fluid to pass from the reservoir and into the piston chambers (but not from the piston chambers to the reservoir) or from the piston chambers to the delivery port 2108. In the examples manifold shown in FIG. 21D four check valves are included within the manifold. The manifold also includes the spool 2122 that may switch the configuration of the manifold between filling, injection and aspiration. In general, as used herein a spool is a rod or cylinder that can move axially within the manifold. The spool may include one or more sealing rings (e.g., O-rings) around its perimeter. The spool may have one or more openings through a side of the body into a chamber within the spool. In some examples, multiple chambers may be present. One or both of the distal and proximal ends of the spool may be open into the chamber within the spool. In this example the spool is an elongate cylinder that includes a plurality of sealing rings dividing the outside of the spool into discrete regions. The spool also includes a hollow central region that is closed at one end, but is open on the opposite end and may be connected to a ball valve (not visible in FIG. 21D) between the distal end of the spool and the cap of the manifold.

FIG. 21D also include components of a pressure sensor assembly, including a displaceable body 2132 that is held within a pressure sensing chamber of the manifold (not visible in FIG. 21D). where it is held between the anterior and posterior ends by a pair of biases (e.g., springs 2134, 2136). One or more sealing rings (e.g., o-rings, gaskets, etc.) 2142, 2144 encircles the displaceable body and divides the pressure sensing chamber into a distal pressure sensing region that receives fluid in the manifold (e.g., in the injection mode) and a proximal pressure vent region that is vented 2118 to the atmosphere. As shown in FIGS. 22B and 22C, showing a side perspective and side sectioned view of the pressure sensor assembly 2160. The pressure sensor assembly includes a magnet 2140 within the displaceable body of the pressure sensor assembly. The entire pressure sensor assembly 2160 may be held within the pressure sensing chamber in the manifold. As pressure in the manifold increases or decreases, it may drive the displaceable body either distally or proximally against the proximal 2136 and distal 2134 biases (e.g., springs); movement of the magnet may be detected by a magnetic field sensor assembly 2138 (e.g., including a hall effect transistor 2139 or other magnetic mounted to or near the baes of the manifold, as will be described in greater detail below, the movement of the magnet may therefore be easily and inexpensively read and the sensed pressure within the manifold using to determine that the pressure is within a desired range, and/or that there is fluid in the reservoir (e.g., not negative pressure).

For example, as described, the pressure sensor may be configured as a pressure-sensing chamber (e.g., bore) that is fluidly connected at one end to the high pressure side of the manifold. The pressure sensor may include a plunger with an o-ring seal. The end of the bore opposite the high pressure side may be vented to atmosphere (e.g., the proximal end). Two biases, such as two precision springs, may locate the plunger within the bore. As pressure increases in the manifold (e.g., within the spool), the plunger may move to the vented side of the bore against the first spring. If pressure falls below atmosphere, the plunger moves toward the high pressure side. The spring rates may be selected such that the plunger moves a pre-determined distance at a given pressure. For example, the plunger may move 2 mm at a pressure inside the manifold of 107 psi.

In this example, a magnet may be concentrically housed inside the plunger. For example, an N54 magnet may be axially polarized. The device may include a linear hall effect sensor. This sensor may be disposed, e.g., about 1 mm away from the pressure sensing bore which may be about 3 mm from the magnet surface. The sensor may be offset from the active hall element such that when the magnet moves, the sensor produces a maximized output signal. This offset may be approximately 3 mm and may provide approximately ¼ full scale ratiometric output from 0-107 psi as the magnet moves about 2 mm. This corresponds to about 300 LSB counts on a 10 bit A/D convertor inside an embedded controller reading the signal. This output is approximately linear and sufficient to allow the controller to sense over and under pressure conditions using lower cost and robust components.

The fluid manifold assembly may include, e.g., four check valves and one or more additional valves (e.g., a ball valve), as described in addition, the body of the manifold assembly may include two chambers when assembled and sealed including a low pressure chamber connected to the reservoir through the spool residing in the chamber. The check valves and the high pressure chamber may be connected to the delivery port (which may be configured as an output needle Luer fitting), through one or more (e.g., two) output check valves.

In some examples, a ball valve may be positioned at the distal end of the spool, so that fluid passing into the spool is selectively operated to either separate the high-pressure chamber from the output chamber, or to allow fluid to pass from the high pressure to the low pressure (outlet) side. The ball valve may be combined with a spring element to provide a pressure relief valve functionality if the pressure at the output half exceeds some predetermined value. When opening against the spring, fluid returns to the bladder saving the device from damage.

As described above, the apparatus includes three distinct states of the fluid system: injection, filling and aspiration. A selector control ("selector) on the device may include positions corresponding to each of these states ("modes"). For example, if the selector control (e.g., knob) is in the fully counterclockwise position, this may correspond to the injection position; if the selector control is oriented vertically, this may correspond to the injection position; while if the selector control is oriented clockwise, this may correspond to the aspiration position. In the injection state, the reservoir is connected to low pressure side, a fill/aspirate second Luer may be shut off, and the ball valve may be held closed. In the fill configuration, the reservoir is fluidly connected to the fill port (which may be a Luer connection) and the ball valve may be either open or closed. Finally, in the aspiration configuration the reservoir connection is closed, the fill port is connected to the low pressure side (the delivery port), and the ball valve is open.

As described above, in some variations the apparatus may include a plurality of pinch valves having multiple states, and a cam may be rotatable inside the housing with a tube on each side of the housing that may either shut off one tube while opening the other or open both tubes. That operation also satisfies the three states described above. The variation shown in FIGS. 20A-20D and 21A-21D does not include tubing or require a pinch valve sub-assembly or barbed fittings.

Figure 23A:
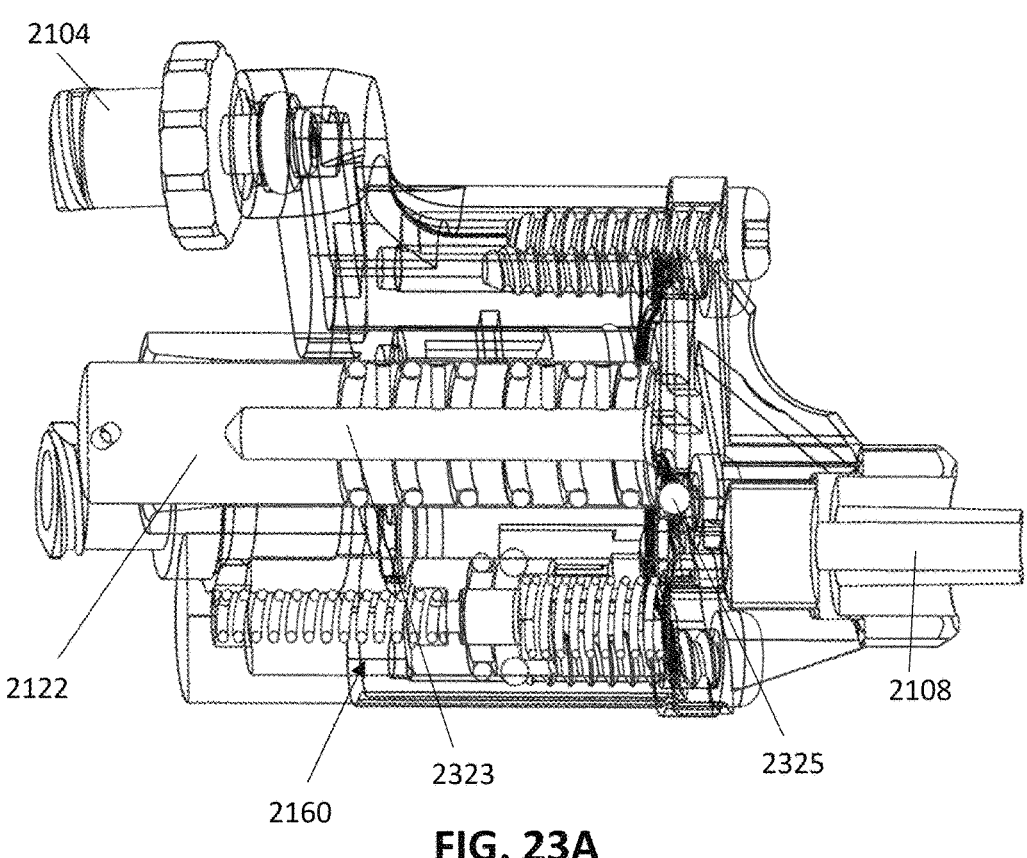
FIGS. 23A and 23B show side sectional views, respectively, of a manifold assembly of an injection apparatus as described herein.
Figure 23B:
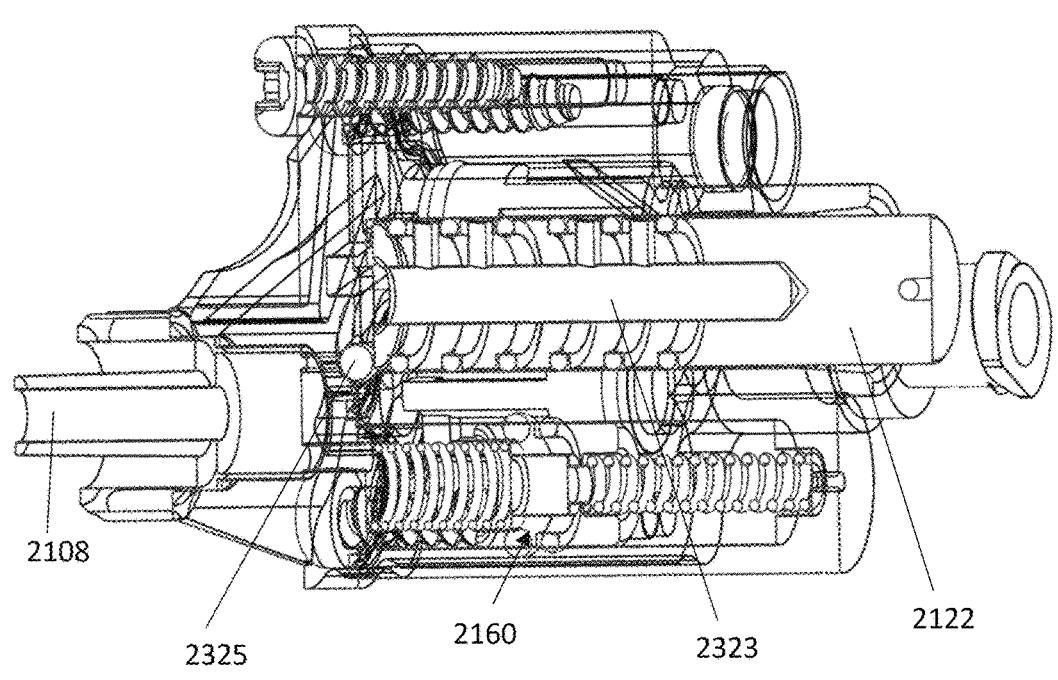

FIGS. 23A and 23B illustrate cross-sectionals view through an example of a manifold assembly similar to that shown in FIGS. 20A-20D and 21A-21D. FIG. 23A shows the left side of the manifold assembly, while FIG. 23B shows the right side of the manifold assembly. These sectional views show the section through the manifold body forming the high pressure chamber in which the spool 2122 resides. The spool including openings along its length (four are shown) that pass into the hollow interior 2323 of the spool. These openings are each separated from each other by a sealing ring. As the spool is moved axially (e.g., distally-to-proximally), e.g., by a cam coupled to the selector, these openings may reconfigure the manifold to couple the delivery port 2108 to the piston chambers (in the injection configuration) through the ball valve 2325, or to instead couple the delivery port 2108 to the aspiration port 2104.

The manifold body may house four cartridge check valves in four bores. The manifold body may also include the pressure sensing chamber (e.g., a large space central to those bores and housing a movable pressure sensor assembly 2160). FIGS. 22B and 22C show the pressure sensor assembly, and it is shown in context in the sectional views of FIGS. 23A-23B.

As shown in the example of FIGS. 23A-23B, an 8 mm bore in the manifold body includes an opening (proximal opening) into which the spool may fit. When assembling the manifold, a plastic ball (for ball valve 2325) may be inserted. This bore may have two radial fluid passages; one fluid path radiates out to a reservoir tube bore where it communicates with the reservoir, and the second fluid path radiates out to the fill/aspirate bore where is communicates with the fill port 2104.

In this example, a 7.95 mm O.D. spool (e.g., spool valve 2122) is disposed concentric within the 8 mm bore. This spool may have five or more o-rings that form three separate fluid chambers that would be sealed from each other in the 8 mm bore. As mentioned above, the spool includes a central bore that opens to the distal end. Additionally, two passages connect the central bore to the separated areas between the o-rings. The spool in this example, includes a proximal end incorporating a cage. This cage feature has two vertical internal walls that are separated by a defined distance. The cage engages with a cam lobe integral to the selector knob shaft. As the selector knob rotates from the 9 o-clock position to the 12 o-clock to the 3 o-clock position the cam translates the spool valve assembly through three states. Each position may have a detent provided by the knob and the product housing. These three rotation positions may correspond to three linear translational positions for the spool valve. Each position selects a distinct fluid connection within the manifold (thereby reconfiguration the manifold to operate under each of these distinct configurations). As mentioned, in the inject configuration, the reservoir may be fluidly connected to the spools central bore, the passage to the fill/aspirate is completely isolated, and the ball valve is held closed. In this state, only the reservoir can supply the input check valves. In the fill configuration, the ball valve is open, the reservoir is fluidly connected via the spool valve central passage to the fill port (which may also be referred to as an aspirate port or a fill/aspirate port). In this position, a syringe connected to the fill port (e.g., a Luer fitting on the fill port) can push fluid into the reservoir. In some examples a shut off valve at the delivery port may be engaged (turned off) to prevent flow during bladder filling. In the aspirate configuration, the ball valve is open, the reservoir is completely fluidly isolated, and the fill port is fluidly connected to the spool valve central bore. In this position, fluid is allowed to flow from the delivery port (e.g., through a needle connect to the delivery port), through the ball valve, and into a syringe connected to the fill port. As the surgeon draws the syringe, if the needle is in a blood vessel, a tinge of blood may be observed inside the clear needle connection or in the clear valve body.

Figure 24A:
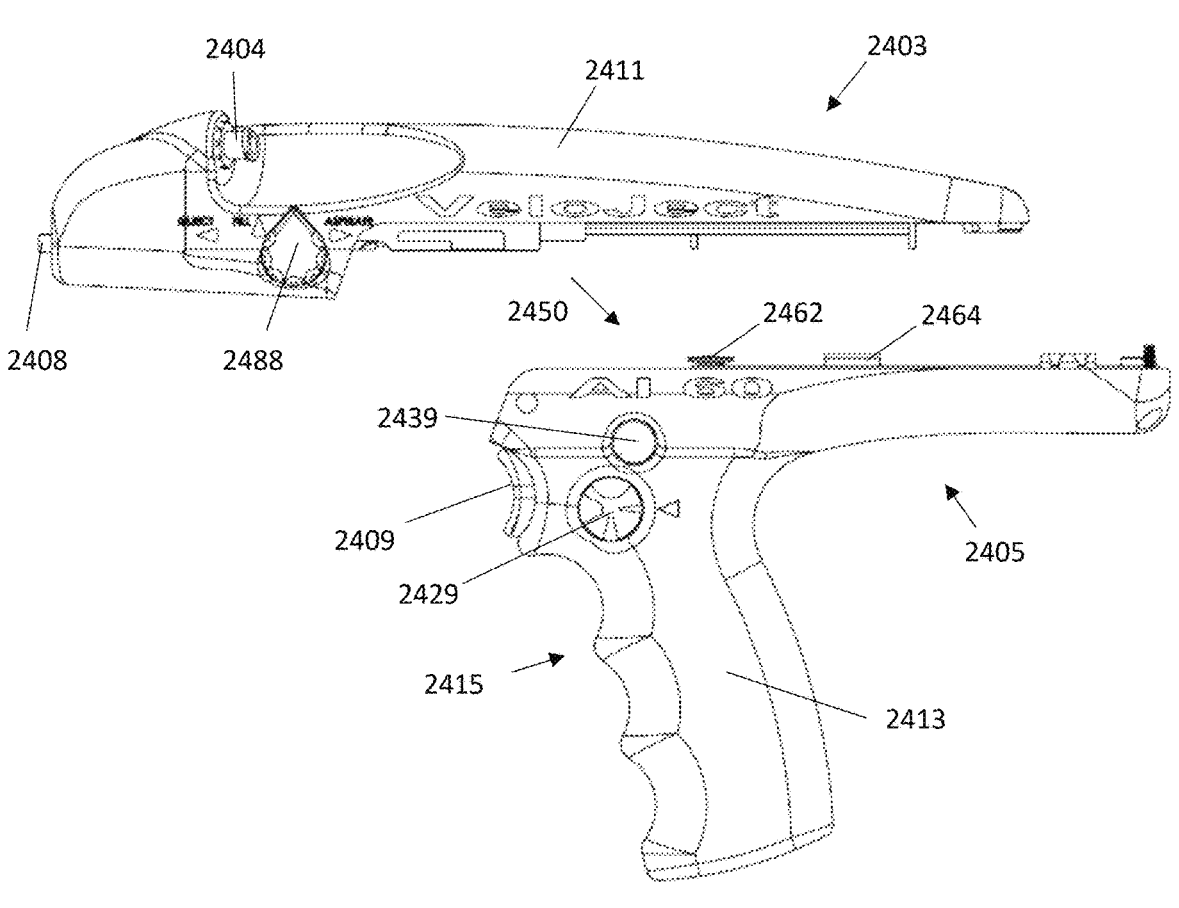
FIG. 24A shows an unassembled injection apparatus including a fluid handling portion and a handle portion that may be assembled together to form a functional injection apparatus as described herein.
Figure 24B:
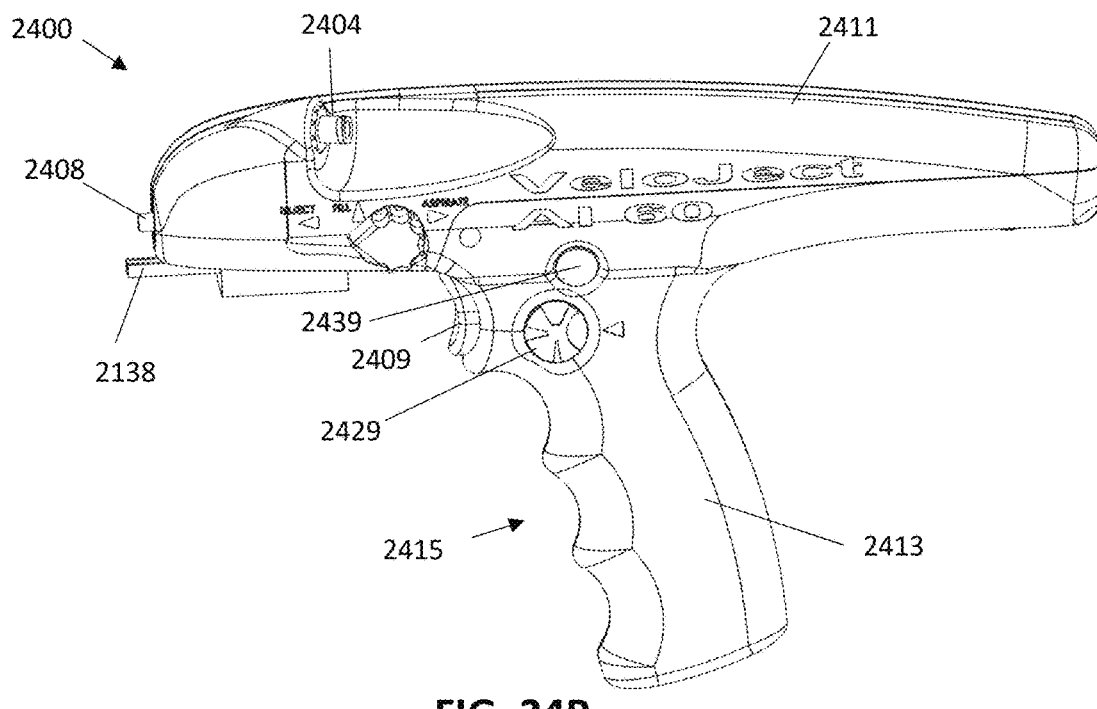
FIG. 24B shows the assembled injection apparatus of FIG. 24A.

Any of the injection apparatuses (devices, systems, etc.) described herein may be configured as two or more component devices that may be combined prior to use. For example, FIGS. 24A and 24B illustrate an example of a two-component (two-part) apparatus having an upper, fluid-handling portion 2403 and a lower handle portion 2405 in this example, the fluid-handling portion includes the portions that contact and direct fluid in the device. For example the first (upper) housing 2411 of the fluid-handling portion may enclose a reservoir, and a first and second piston chamber, as well as a manifold including the plurality of check valves (not visible in FIGS. 24A-24B). The fluid-handling portion also includes a delivery port and a fill port 2404. In addition, the fluid-handling portion also drive assembly (not visible in FIGS. 24A-24B) including a transmission that is operatively connected to a first piston in the first piston chamber and a second piston in the second piston chamber so that the drive assembly can reciprocally move the first and second pistons.

In FIG. 24A, the fluid-handling portion also includes a selector control 2488 that includes three positions (inject, fill, and aspirate), shown marked on the housing.

The fluid-handling portion may be coupled 2450 to the lower, handle portion 2405, as shown in FIG. 24B, showing the fully assembled apparatus 2400. The handle portion may include a second housing 2413 that includes a grip region 2415. The handle portion may also include one or more controls for operating the device, such as a trigger control 2409 and a fluid volume control 2429. In this example, the fluid volume control is configured as a dial that may be rotated to select between three fixed-volume settings a continuous flow setting (e.g., 1 cc, 2 cc, 3 cc and continuous). The handle portion may enclose or partially enclose the driver (e.g., motor) and control circuitry (e.g., controller). The handle portion (or in some examples, the fluid-handling portion) may include one or more indicators, such as an indicator light (e.g., LED) 2439 that may indicate, for example, power status (on/off, etc.), error (over-pressure, empty reservoir, etc.), in use/ready, etc.

These two portions, the fluid-handling portion and the handle portion may be combined together by engaging one or more coupling features 2464 on the fluid-handling portion and/or the handle portion. In particular, the driver in the handle portion may engage 2462 with the drive assembly (including the transmission operatively connected to the pistons of the piston chambers) so that the driver may controllably drive fluid out of the injection port of the device. Thus, in some examples the apparatus may include an upper fluid subassembly (fluid-handling portion) and a lower handle portion. This configuration may allow different sterilization methods for each portion, such as gamma sterilization for the fluid-handling portion and ethylene oxide gas sterilization for the handle portion (containing electronics that may be sensitive to some sterilization techniques).

The multiple parts (the fluid-handling portion and the handle portion) of the apparatus may be packaged separately, in sterile packaging, and may be combined prior to use. In some examples combining the two parts may activate the device (e.g., turn it "on") and separating the two parts may de-activate the device (e.g., turn it "off") so that a separate "on" switch is not needed. In some variations a separate "on/off" switch may be included. In some examples the fluid-handling portion may be disposable, single-patient use and the handle portion may be re-usable with multiple fluid-handling portions (including with multiple patients). Thus the handle portion may include rechargeable batteries and may be re-charged during use. In some examples a separate "battery" portion may be swapped into the handle portion, allowing already-charged batteries to be swapped into the handle (e.g., the apparatus may include three components, rather than just two). Any of the apparatuses described herein may be used with a cord that may provide power from a wall source (e.g., plug or plug and adapter).

The controller may be configured to operate autonomously or it may be configured to communicate, e.g., wireless (via Wi-Fi, Bluetooth, etc.) to a remote server. In some examples the apparatus may transmit status information to a remote server and/or to a handheld device (e.g., phone, etc.). For example, the apparatus may transmit cycle counts, power status, fill status, error status, etc. Alternatively or additionally the apparatus may include a display on the device (e.g., on the handle portion) for displaying any of this information.

In some examples the fluid-handling portion may be locked (including releasably locked) to the handle portion. The lock may be a latch (e.g., including a hook, snap, clasp, etc.) and may include a release on either or both of the fluid-handling portion and/or the handle portion. In some examples the lock may be on the housing (shell) portion or may be coupled to the housing(s), such as the housing for the fluid-handling portion and the housing for the handle portion. The lock may prevent separation of the handle portion and the fluid-handling portion unless and until the lock is disengaged.

As mentioned, the handle portion may include the controller or control circuitry. In some examples the apparatus includes firmware that may incorporate a calibration function (e.g., performed at the factory) where pressure and vacuum are alternately cycled and sensor values tabulated. The firmware may linearize the data and store permanent coefficients in EEPROM memory to use for monitoring routines when the apparatus is operating. The calibration process may reduce the need for precision assembly and tight tolerances.

The pressure-sending subassembly within the apparatus may allow the processor to detect when pressure exceeds a safe threshold and it may alert the user and/or protect the apparatus, e.g., by disabling the driver and/or venting the device. Additionally, if the device is being operated with and empty reservoir, vacuum may be detected and the device may issue an alert and/or disable the driver.

Figure 25A:
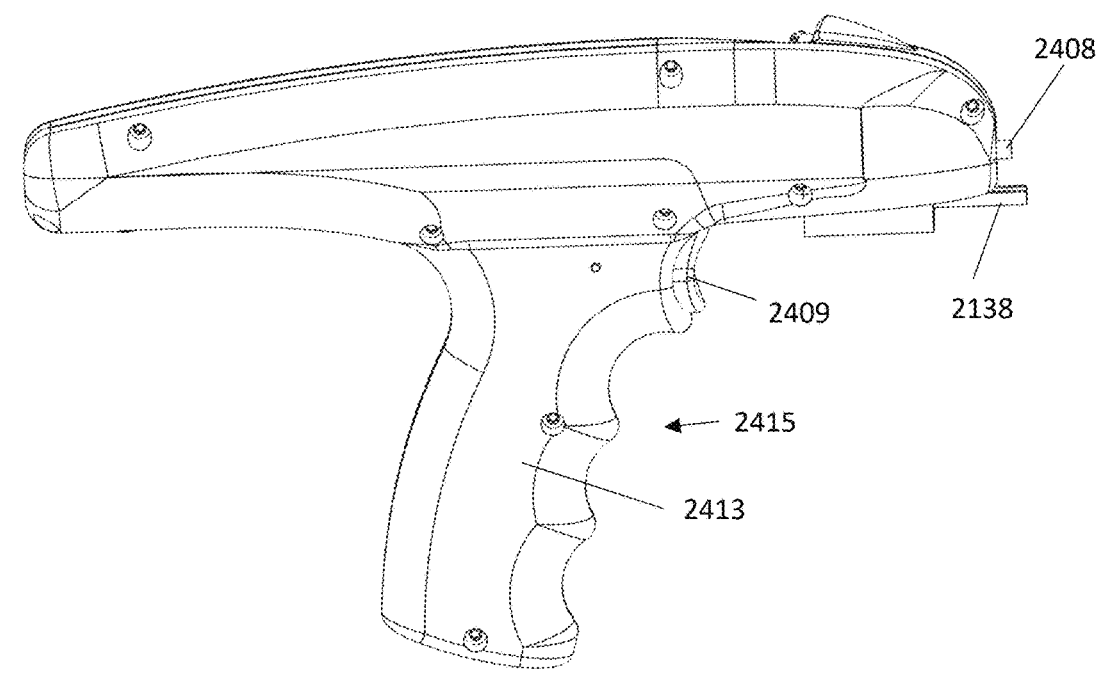
FIGS. 25A, 25B and 25C show side, top and bottom plan views, respectively, of an injection apparatus.
Figure 25B:
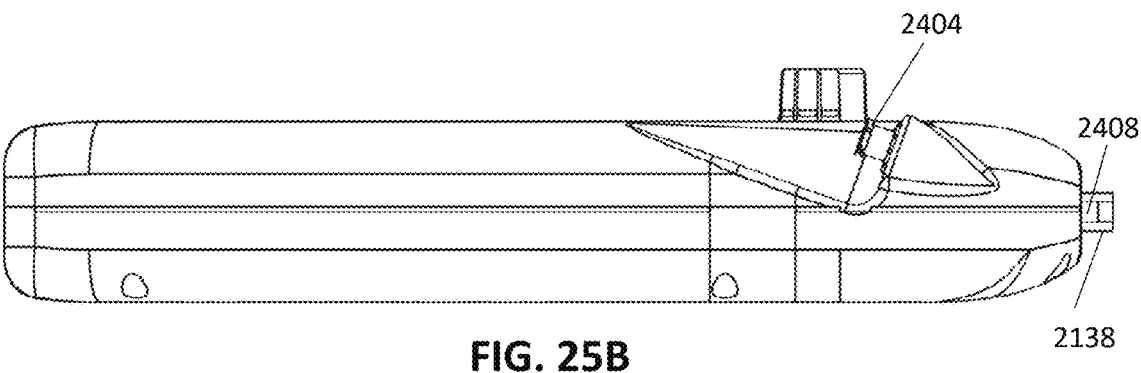
Figure 25C:
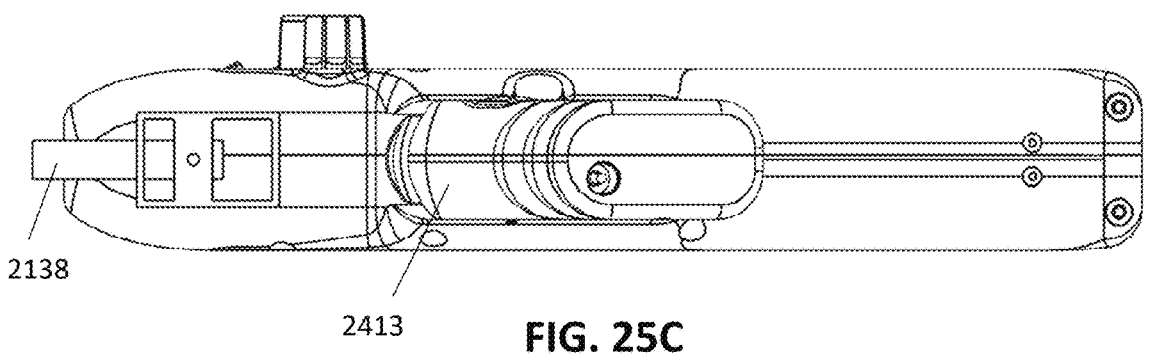

FIGS. 25A-25C illustrate side, top and bottom views of one example of an injector apparatus as described herein, similar to that shown in FIGS. 24A-24B. FIG. 25A shows the left side of the device; the controls, such as the fluid volume control, on the rights side (shown in FIG. 24B) may be instead located on the left side in some examples. For example, devices may be configured as left-handed or right-handed. The overall form factor may be compact and lightweight, allowing the user to hold and operate the device with one hand, if desired.

Figure 26:
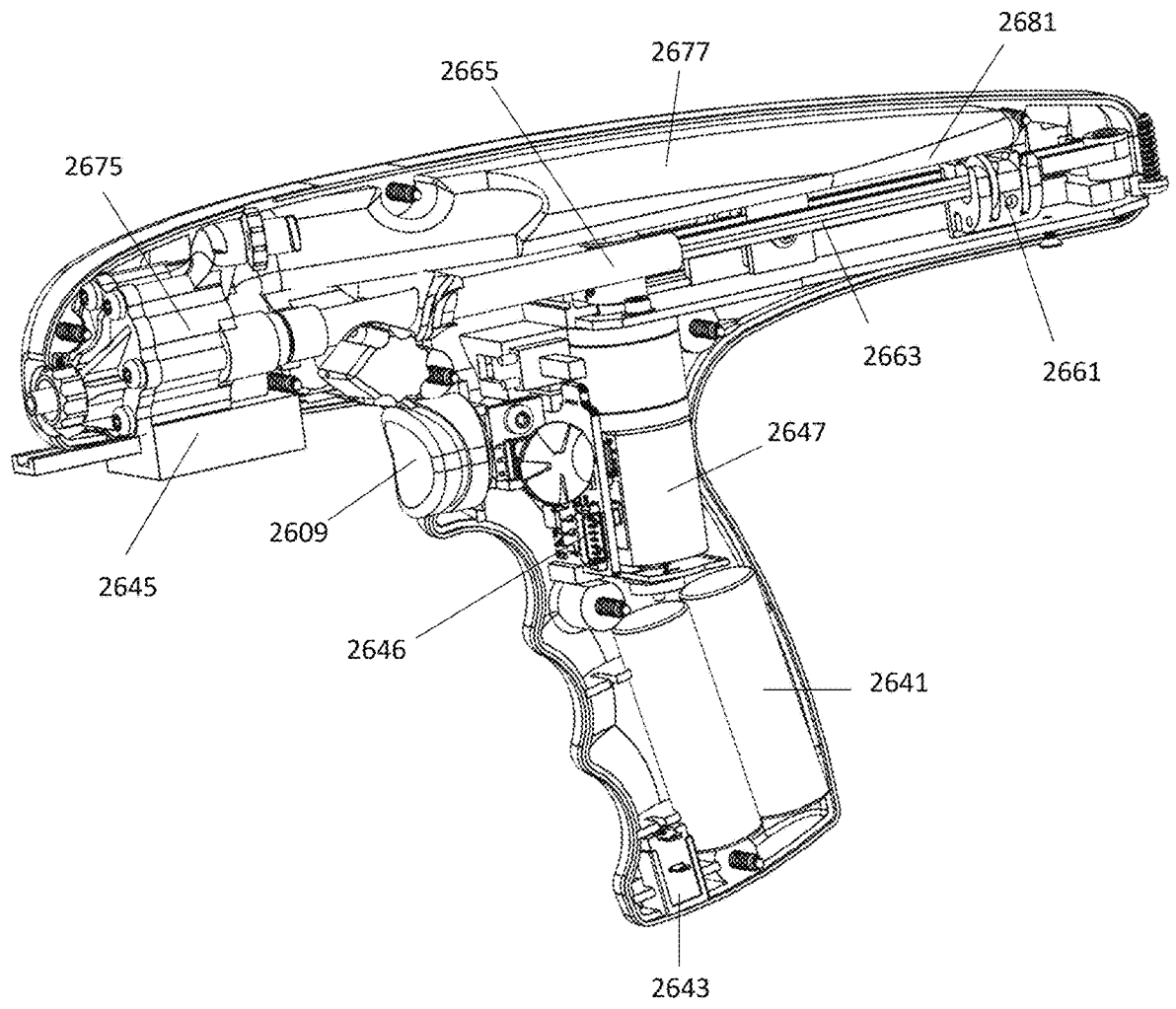
FIG. 26 is an example of an injection apparatus similar to that shown in FIGS. 24A-24B and 25A-25C with the front of the housing over the handle and fluid handling portions removed.

FIG. 26 shows a side perspective view of the apparatus of FIGS. 25A-25C, with a portion of the housing(s) made transparent to show the arrangement of components within. In FIG. 26 the handle region encloses the power supply (shown as a pair of batteries 2641) as well as power control components, such as a charging port 2643. In this example, the housing region also encloses control circuitry 2646 that receives inputs from the one or more sensors (including pressure/forces sensors coupled to the trigger control 2609 and/or pressure sensors 2645 detecting pressure within the manifold and/or force/pressure sensors for detecting the force applied by a user to the trigger, and/or encoders for encoding movement of the driver (e.g., motor 2647). The example shown in FIG. 26 also shows a partial view of the drive assembly, including an interface 2661 coupling the drive assembly to the plunger (piston 2663) within one of the piston chambers 2665 that is coupled to the manifold 2675. The apparatus shown also include a reservoir that has been filled, so that it displaces a pressure-applying component (shown here as a compressible ballistic foam 2681).

Figure 27A:
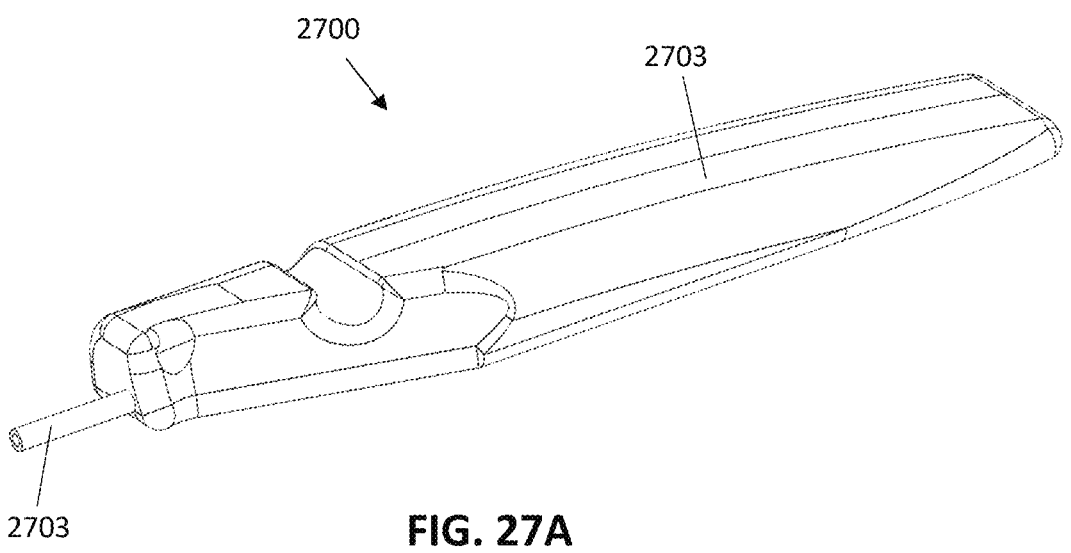
FIG. 27A shows one example of a reservoir, configured as a collapsible bag.
Figure 27B:
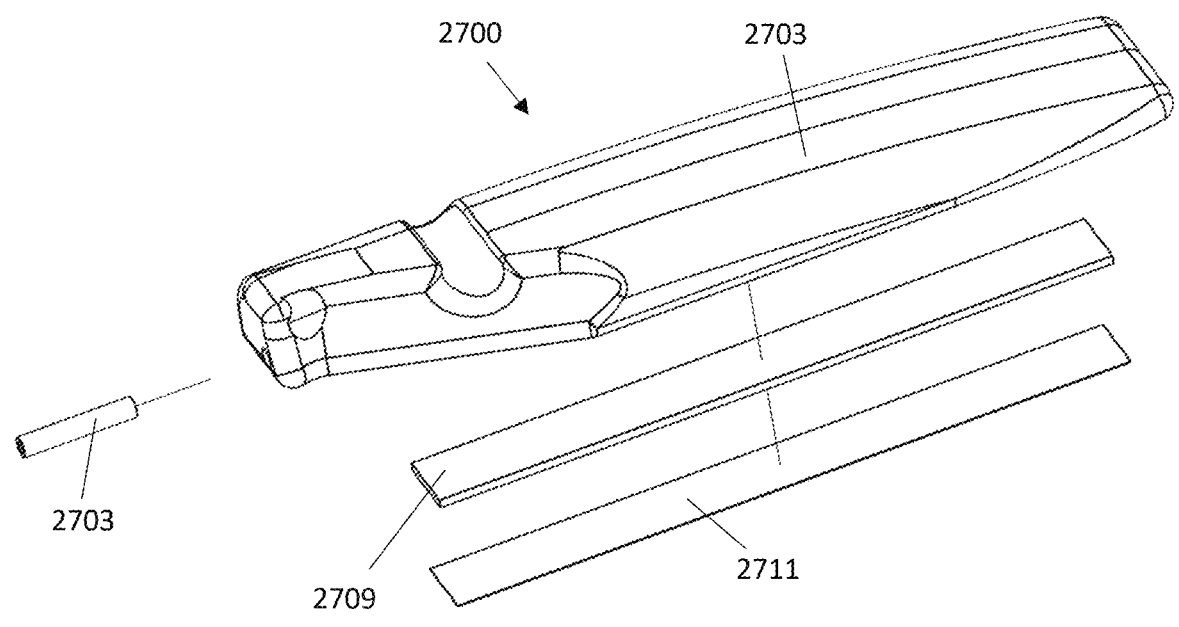
FIG. 27B shows an exploded view of the reservoir of FIG. 27A.

FIGS. 27A-27B illustrate an example of a reservoir assembly including a reservoir chamber 2701 and a reservoir inlet/outlet 2703. The reservoir assembly in this example also include a compressible foam 2709 (shown in the compressed state in the exploded view of FIG. 27B). An additional attachment or support layer 2711 may also be included. The reservoir in this example is a polyethylene bag that may be collapsed by the expansion of the foam when fluid is not present within the reservoir.

Figure 28A:
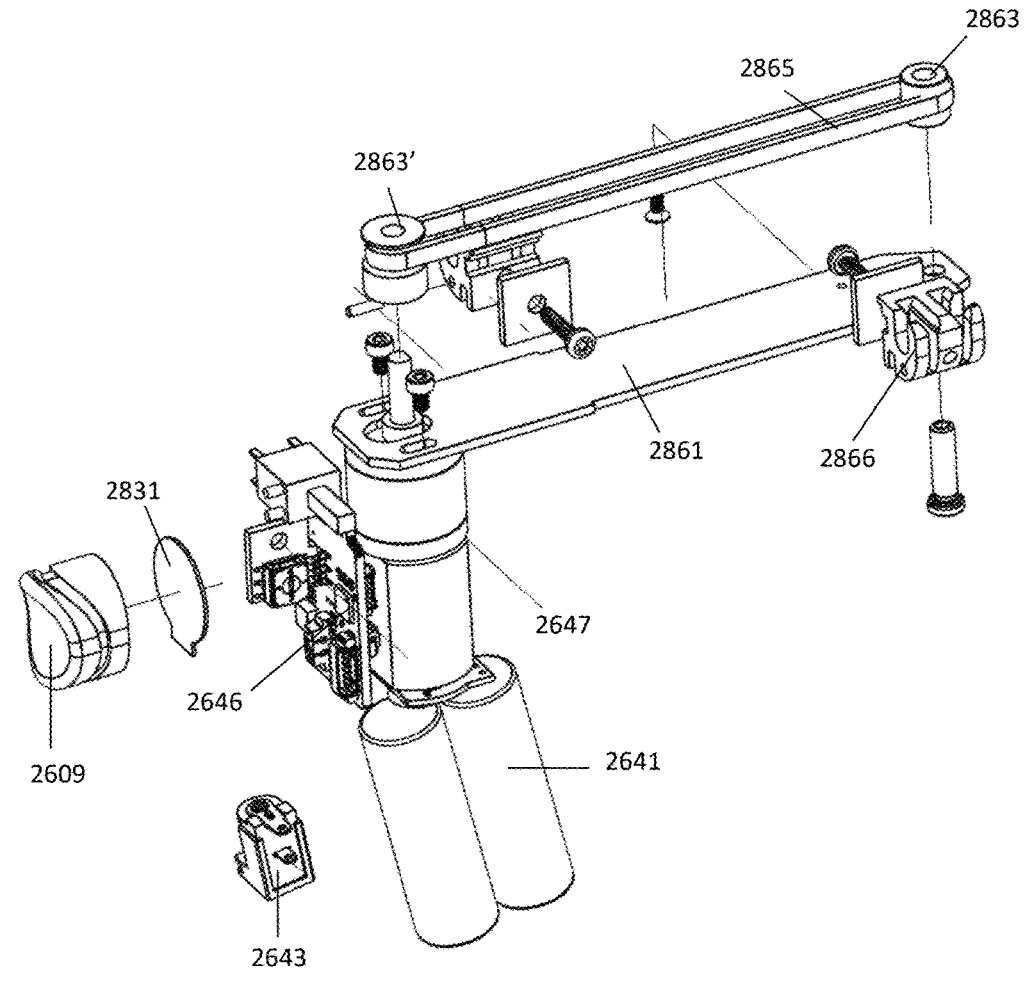
FIG. 28A illustrates one example of a drive assembly, driver, controller, and trigger control for an injection apparatus as described herein.

FIG. 28A shows an example of a driver (e.g., motor) engaged with a drive assembly of one example of an injector apparatus. In this example, the drive assembly includes a belt 2865, and a pair of pulleys 2863, 2863'; each piston within the piston chambers may be coupled to the belt, e.g., using an interface 2866. In the example shown, the drive assembly is mounted to a support 2861. The motor 2647 in this example engages with the pulleys of the drive assembly and may rotate in either clockwise or counterclockwise directions to reciprocate the pistons (plungers) of the piston chambers. The power supply (e.g., batteries 2641) and charger 2643 are also shown, as well as the controller 2646, trigger control 2609 and pressure/force detector 2831 reading the user-applied force to the trigger control. Thus this example apparatus includes a recharging port and also a fixed battery. A typical shelf-life of charge is one year.

Figure 28B:
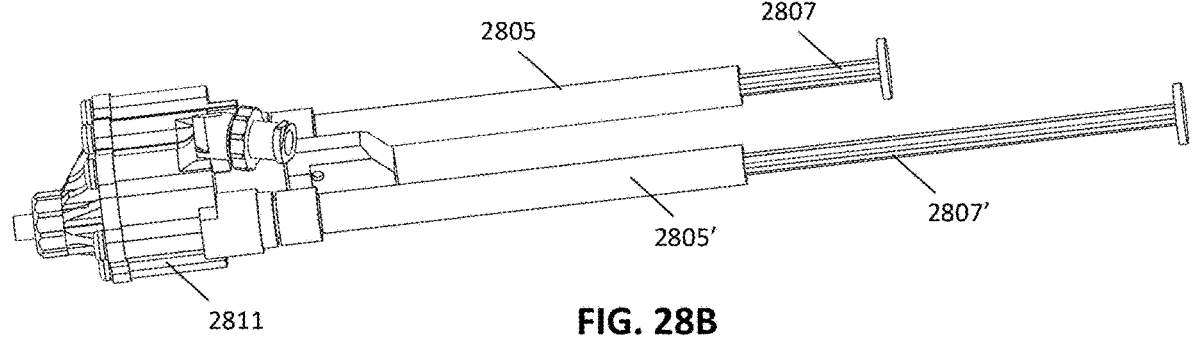
FIG. 28B illustrates an example of a pair of piston chambers, pistons and manifold that may be used with (e.g., coupling the pistons to the drive assembly) the drive assembly of FIG. 28A.

FIG. 28B shows one example of the first and second piston chambers 2805 and pistons (plungers 2807) within each piston chamber. As mentioned, the pistons (plungers) may be coupled to the drive assembly by an interface; in some examples the interface engages with the ends of the plungers. The distal ends of the piston chambers is shown coupled to a manifold 2811 as described above.

The drive system shown in FIG. 28A may include a home position. In one example there may be direction sensing implemented using a hall sensor, a magnet, and encoder on the moving block. When the power is turned on, the moving block may run until the sensor detects a signal. If (e.g., in the turned-on condition) the home position is not detected, then the motor can run in one direction. Once home position is detected, the system may initialize based on the magnetic encoder count; if the trigger is pressed, the direction the drive systems turns is known from the detected home position.

Any of the apparatuses described herein may include hardware, software and/or firmware that may track the operation of the device, including the number of cycles performed. The controller/control circuitry may include one or more memories or registers that may record the number of cycles. In some examples if the number of cycles exceeds a cycle limit threshold, the apparatus may shut down (a warning may be issued a fixed number of cycles before shut-down). For example, after 400 cycles, after 425 cycles, after 450 cycles, after 500 cycles, after 550 cycles, after 600 cycles, etc.

In some examples the apparatus may track the number of cycles from filling of the reservoir. As mentioned, these cycles may be displayed (e.g., in a display on the device or in communication with the device, including in wireless communication with the device).

Any of the apparatuses described herein may include valves at one or more of the ports (e.g., the fill port, the deliver port). For example, the fill port may include a Luer lock with a valve that may prevent backflow when removing the filling source from the fill port. For example, the fill port and/or the delivery port may include a manually operated valve (switch) to open/close the port.

Thus, the injection apparatuses described herein may be battery/motor powered apparatuses to deliver fluid into tissues of varying resistance in a controlled manner while relieving the physiological stress imparted on the surgeon/operator. Any of the apparatuses described herein may be configured for use with an external device, such as a navigation unit, robot and/or artificial intelligence system. For example, these apparatuses may be fitted with external arrays and registration/check points and internal inclinometer/microsensors that may record fluid velocity/volume/resistance to help identify anatomic location of the injection, volume/resistance of the fluid injected. Any of these apparatuses may emit data (e.g., by radiofrequency, Wi-Fi 33, etc.). The apparatus may record/provide feedback on the volume, velocity, resistance during injection, and anatomical location of the material delivered. Any of these apparatuses may include an inclinometer to describe the orientation of the device during usage. In some examples the apparatus may be fitted with arrays/registration points to interact with robotic and navigation devices to allow these devices to interpret the dimension/location/orientation of the device at the time of the injection. This may allow for an understanding, recording and/or analysis of the anatomical location where the device was delivering its intended product. The use of position/orientation and/or applied pressure/force may be implemented with either a single-use disposable apparatus and/or with a modular (e.g., partially disposable) apparatus.

For example, injection volume, velocity and/or resistance data from the apparatus can be transmitted in real-time wirelessly (e.g., via radiofrequency, Bluetooth, Wi-Fi, etc.) and/or uploaded at a later time to a remote processor that may analyze the data. For example, the remote processor may receive the gauge of needle used, the type of material injected, location/volume of injected material, time(s) during the procedure that materials were injected, composition of injected material, etc. The remote processor may analyze this data in conjunction with the anatomical location of injection, velocity, resistance and/or volume of injection and pre/post-operative functional outcomes.

For example, any of the apparatuses descried herein may work with a database of injection information that may be generic (e.g., not specific to a particular patient). Thus, these apparatuses may be configured to contribute to a database of injection information as described above. This database, which may be maintained in one or more remote locations, may be analyzed and used to optimize treatments for patients, and/or to optimize the functioning of the injection apparatuses. For example, a system including a database of injection information may identify specific locations, volumes and/or substrates that may be indicated for use in order to improve pre-operative through post-operative outcomes for patients. Thus, these databases may receive information regarding pain, immediate post-op function, and consumption of pain medication post-operatively; this information may be correlated with the functional aspects of the apparatuses delivering the treatment. A machine learning agent may interpret this information and may indicate one or more: locations to deliver treatment, delivery rates, delivery volumes, etc. These systems and methods may also or alternatively identify the efficacy of substrates injected, as it pertains to the specific composition, volume and/or location of the injection; for example, these systems may determine if a local anesthetic, e.g., Exparel, is an effective pain medication for a particular patient or class of patients.

Thus, any of the apparatuses described herein may be configured to provide operational information to a remote database for processing; the operational information may be correlated with treatment information (that may be patient specific or unaffiliated with a particular patient). For example, the apparatus may be uniquely identified via a code specific to the apparatus or to a particular operation of the device. A particular operational instance (e.g., use) of the device may include information (which may be transmitted to the remote database by the user or a party working with the user) that may include pre- and post-operative functional data for the patient, a location of the procedure being performed with the apparatus (e.g., hospital/hospital outpatient department/ambulatory surgery center), pre- and post-operative consumption of NSAIDS, Tylenol, narcotic, etc. medications by the patient, etc. The apparatus may also transmit with the same identifier, intra-operative data obtained through the use of this apparatus, as described above. The remote processor may assess the efficacy of the method and/or the type of substrate injected and/or the location of the injection/volume of substrate injected.

Thus, a system (which may include hardware/software and/or firmware) may analyze information such as that described above, including all or some of: patient profile (age, sex, BMI, bone density), pre/post-operative functional/psychological/etc. scores, pre-operative x-ray evaluation, pre-operative physical exam, post-operative x-ray, post-operative physical exam, medication utilized pre- and post-operatively, location where surgery was performed procedure (hospital/hospital outpatient department/ambulatory surgery center), (orthopedic, or other) implant used, type of substrate injected (anesthetic, filler, etc.), and/or anatomical location/volume/speed/resistance of injection. This system, when used in conjunction with an orthopedic robot and/or navigation system, may utilize identify treatment parameters for treating patients, including treating patient's to restore anatomical alignment/range of motion/balance of a knee replacement, location of where a procedure is performed (hospital vs ASC), type of anesthetic used (spinal vs general+/−peripheral nerve block), location/volume injected/type of anesthetic injected, peri-operative medication utilized, which type of orthopedic implant/design to use (e.g., cruciate retaining vs posterior stabilized), etc. These systems may also provide expected functional outcomes specific to a particular patient's profile. For example, these systems may also or alternatively provide treatment parameters for operation of the injection apparatus, such as injection location(s), and/or injection volumes, rate o injection, etc.

Figure 29:
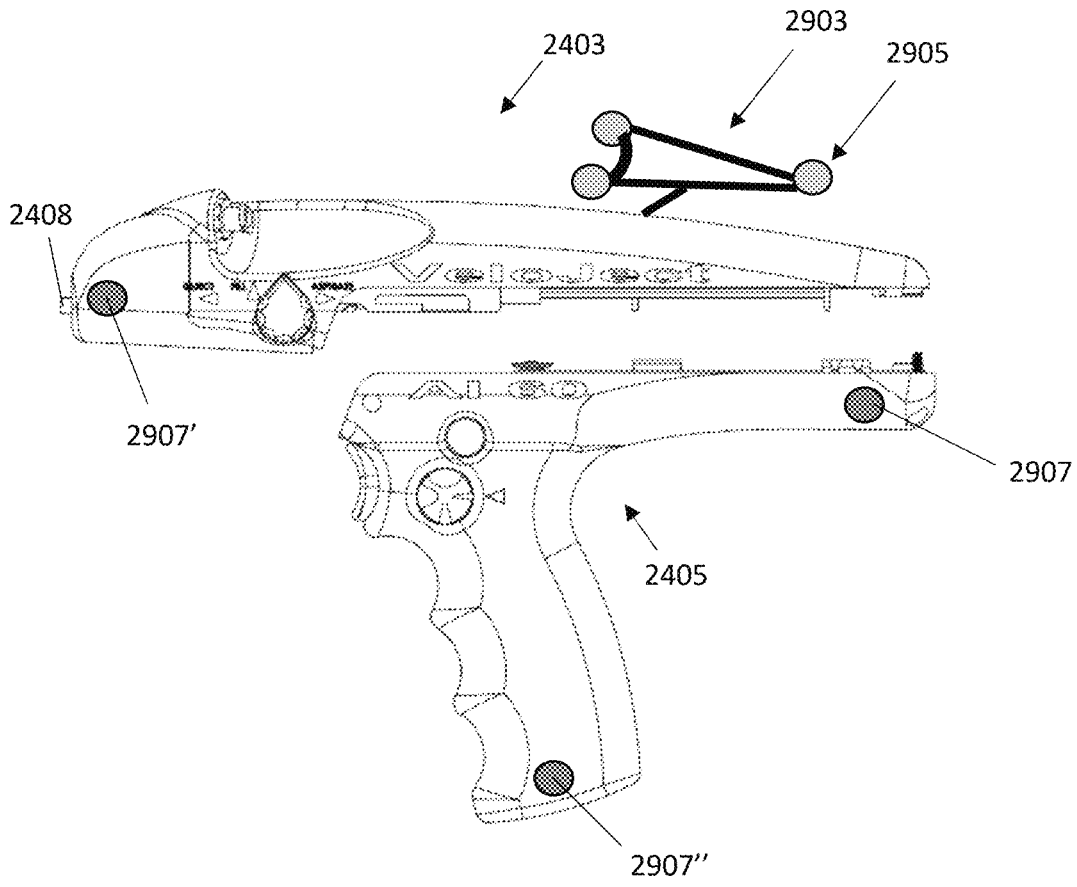
FIG. 29 is an example of an injection apparatus similar to that shown in FIG. 24A including tracking markers for tracking the position and/or orientation of the apparatus during use.

As mentioned, any of these apparatuses described herein may be configured to operate with a system including a database of injection treatment parameters. For example, any of these apparatuses may include a communications sub-system, such as a wireless communication circuitry; the controller of the apparatus may use the wireless circuitry to communicate with a remote database. The controller may also include timing information (e.g., clock, calendar, etc. information). Any of the injection apparatuses described herein may include one or more tracking components. The tracking data may be stored, modified (e.g., filtered, compressed, etc.) and/or transmitted, etc. to a remote processor as described. FIG. 29 illustrates one example of tracking components one or more of which may be included in any of the apparatuses described herein.

In FIG. 29, a two-component apparatus (similar to that shown in FIG. 24A-24B) is show, however, the tracking components may be included in any of these apparatuses. In FIG. 29, the apparatus may include a tracking array 2903, which may be, e.g., an infrared reflective material 2905 (e.g., sphere, disk, etc.), which may be on the apparatus. A tracking system may be positioned near the patient to track movement and/or orientation of the injection apparatus during a procedure, including tracking the one or more (preferably three or more) IR tracking markers (e.g., IR reflective materials). In some examples the apparatus (e.g., either or both the fluid-handling portion and/or the handle portion) may include one or more registration checkpoints. In FIG. 29, three registration checkpoints 2907, 2907', 2907" are shown, located on the distal end (near the delivery port), the proximal end (on the fluid-handling portion), and at the base of the handle portion. These registration checkpoints may be tracked using, e.g., an external tracking apparatus. The tracking information may be correlated (and stored, transmitted, etc.) with operational information from the injection apparatus (including injection flow rates, amounts, etc.), as well as with additional patient-specific data (procedures, outcomes, etc.).

Any of the apparatuses described herein may be further adapted for use with a robotic system. For example, the injection apparatus may be adapted for use with a robotic arm that may position and deliver an injection from the apparatus. Thus, the handle portion may be adapted for interacting with a robotic arm; the robotic arm may engage with the handle portion, including the trigger, and may position and actuate the apparatus. The tracking markers on the apparatus (e.g., FIG. 29) may assist the navigation and/or control system for the robotic apparatus.

EXAMPLES

Also described herein are apparatuses having alternative configurations for the fluid delivery and aspiration components of the apparatuses described herein. For example, FIG. 30 illustrate another example of an apparatus as described herein. In this example, the core components of the injection apparatus are show, showing the drive assembly, tubing and multiple check valves; in this example the apparatus does not include a dedicated manifold as described above. The apparatus shown in FIG. 30 include an aspiration port 3005, a delivery port 3001, a shuttle dual check valve 3007, top fill port 3009, trigger control 3015, piston chamber(s) 3019, and cylindrical reservoir 3011. FIGS. 30B and 30C show side perspective and bottom views, respectively, of the same apparatus.

This example of an injection apparatus may have a plunger that can be activated by the finger of the user while holding he handle of the device. The retraction of the shaft with the trigger and plunger would create a vacuum at the tip of the device pulling fluid from the needle back into the clear tube at the end of the device. A blush would show informing the user that the tip of the needle is in the vascular system.

The apparatus can also be configured to block fluid flow during the filling operation of the device. For example, the user can hold the device, retract the trigger blocking the flow of fluid out of the needle port and forcing the liquid to fill the reservoir. The trigger could then be released allowing the user to prime the system using the fill port.

Figure 30A:
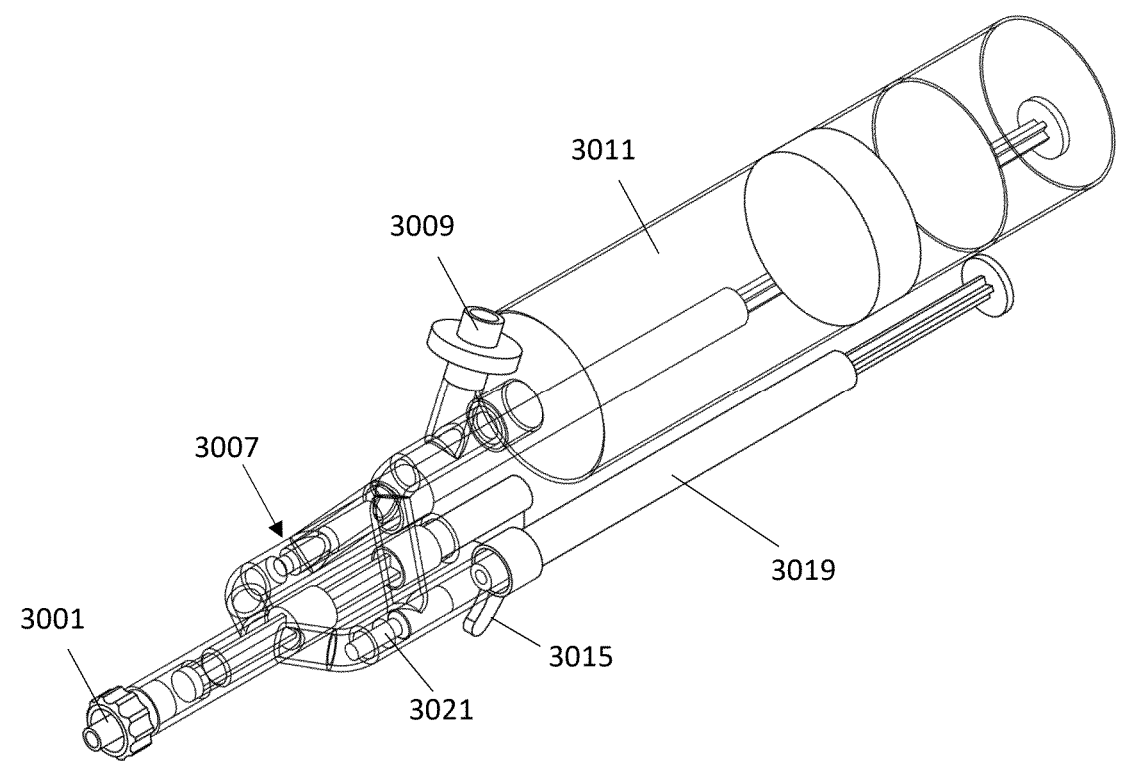
FIGS. 30A-30C illustrate side perspective, side and bottom views, respectively, of another example of a portion of an injection apparatus as described herein.
Figure 30B:
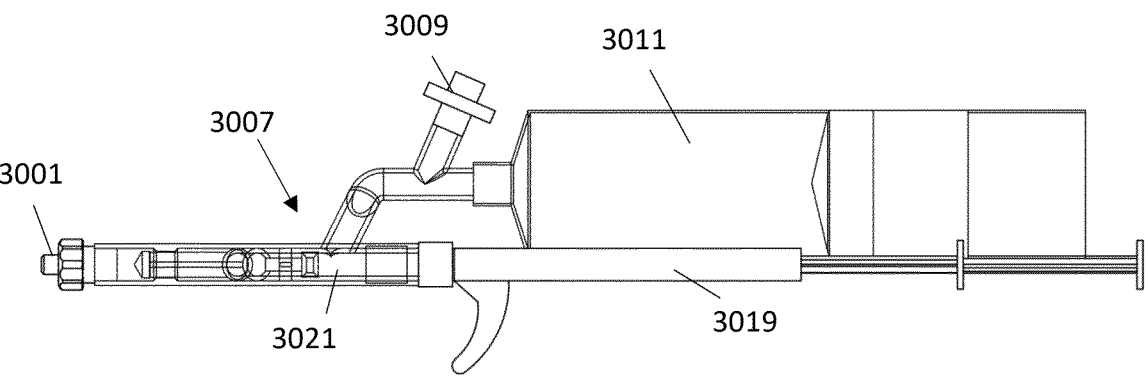
Figure 30C:
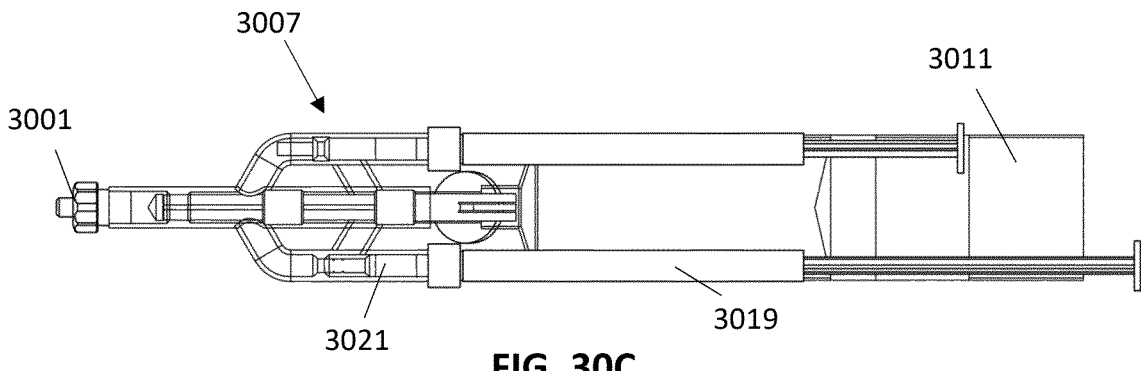

Any of these apparatuses, including the apparatus shown in FIG. 30A, may be configured to include a plurality of shuttles within the fluid path to act as a dual check valve for directing fluid from the reservoir to the smaller piston chambers (e.g., syringes) and out the piston chambers to the needle as the plungers of the small syringes are drawn back and forth. The shuttles may have a hollow center portion from the back end to a through hole in the front section. The outer surface of the shuttle and the inner surface may be configured such that fluid cannot pass around the shuttle. This can be accomplished with matching diameters or with a mechanical bushing. The shuttle can be in two states at the extreme of its travel; one state when the shuttle is drawn back toward the small syringe in line with the shuttle. This may occur when the plunger on that shuttle is being pulled out expanding the volume of the syringe and pulling a vacuum to draw fluid into the syringe. The vacuum draws the shuttle back toward the syringe, closing off the fluid path to the needle exit port and opening the path from the reservoir to the smaller syringe. When the plunger switches direction and begins to expel fluid from the syringe, the shuttle is pushed all the way forward. The outer diameter of the back portion of the shuttle blocks flow into the reservoir and the path is through the body of the shuttle out the exit hole in the front of the shuttle into the exit path of the needle. Because the two syringes are set to be moving always in opposite directions there will always be fluid pumping from the reservoir into a small syringe and fluid being expelled from a small syringe out of the needle.

For example, FIG. 31 shows an enlarged view of the shuttle 3021 from FIGS. 30A-30C. In FIG. 31, the shuttle includes a thru hole and a front section port.

FIGS. 32A and 32B show schematic illustrations of two different fluid systems including an aspirate valve. The apparatuses described herein may be configured according to either of these schematics. In FIG. 32A, the fluid-handing circuit includes a pair of piston chambers 3211, a reservoir 3205, a fill port 3207, a delivery port 3209, and five check valves 3213. FIG. 32B shows an alternative arrangement, including an aspiration port 3219. These apparatuses can be filled from the top with a port that can accept a large syringe, for example. The access line may have an inline check valve to allow fluid into the system without allowing back flow.

In any of these apparatuses, the reservoir can be a larger syringe with the plunger extension removed. This may decrease the length requirement of a full syringe, but allows the advantages of a piston configuration such as a clear tube to identify air in the system, clear visualization of the amount of fluid remaining in the reservoir, and familiarity of the device by the user. Markings on the cylinder can indicate the accrual of fluid volume during filling and the expelling of fluid during injection. This may also provide feedback to the user. The user can see if the plunger is moving as they dispense fluid indicating proper operation and warning that fluid is running low.

Figure 35:
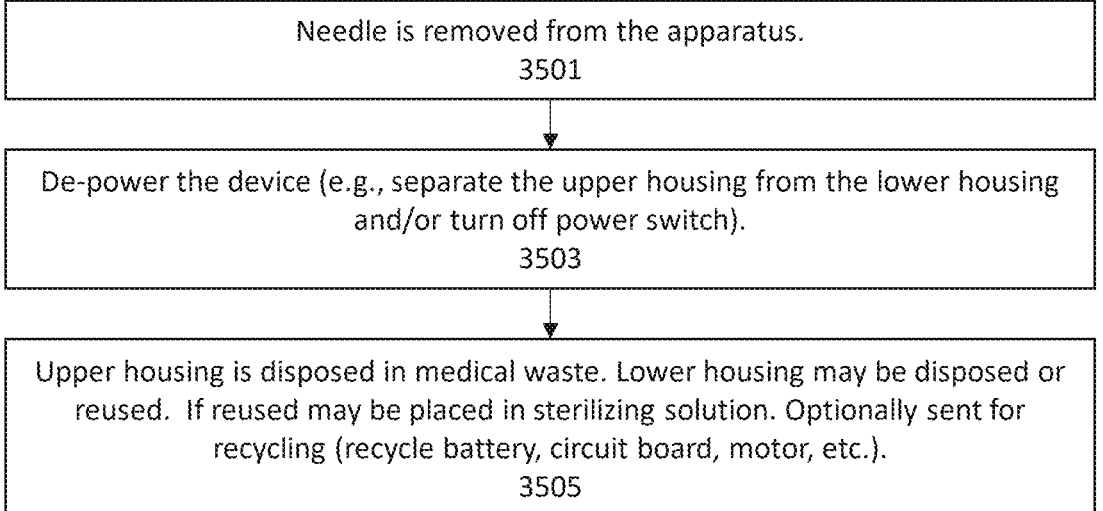
FIG. 35 is a chart illustrating a method of ending an injection session.

FIGS. 33, 34 and 35 illustrate methods for preparing for use, using and completing use of an injection apparatus as described herein. These methods, and/or any or all of the component steps of these methods, may be combined for an overall method of use. These methods may be used with any of the apparatuses described herein. For example, FIG. 33 illustrates a method of preparing an injection apparatus for use. For injection apparatuses that include multiple portions that may be kept separate before use (such as shown and described in FIG. 24A-24B, above), the apparatus may first be assembled 3301. For example, an upper half (e.g., a disposable portion), such as a fluid-handling portion and a lower half (e.g., reusable) portion such as a handle portion, may be kept separately in sterile conditions and may be assembled by attaching together. Combining upper half and lower half may power on the apparatus. In some examples a light, e.g., an LED, may illuminate to indicate the device is assembled, powered and ready for use. In some examples the apparatus may be initially set so that it is in a fill mode; alternatively, the device may be set into the fill mode by setting a selector (e.g., knob) to a "fill" position 3303. The device may then be filled. In some cases, the user may manually close the delivery port (e.g., by attaching a cap and/or by switching a valve on the delivery port to closed 3305. Alternatively in some examples the apparatus may automatically close off the delivery port.

Prior to filling the fluid to be injected may be prepared. For example, if a drug (e.g., Exparel, Bupivacaine, Marcaine, etc.) is to be injected, it may be premixed to the appropriate concentration. The fluid may then be loaded into the reservoir of the apparatus. 3307. In some examples, the fluid may be added by a syringe or other filling device that may couple to the fill port on the apparatus. For example, a 60 cc syringe full of fluid (e.g., liquid drug) may be attached to the Luer connection of the fill port and the piston of the 60 cc syringe pushed in to deliver the liquid into the reservoir, which may expand as it receives the liquid (preventing air bubbles). Once filling is complete, in some examples the apparatus may be switched to an injection or aspiration mode, which may close the path between the fill port and the reservoir (preventing back flow from the reservoir. As mentioned above, in some examples the path between the reservoir and the fill port may include a check valve preventing back flow; alternatively a manual valve (switch) may be included to shut off the connection between the fill port and the reservoir.

A needle of any appropriate size may then be attached to the injection port (e.g., via a Luer lock) 3309. The apparatus may then be primed 3311, to remove air within the device. For example, the apparatus may be primed by aiming the apparatus up and, with the device in the continuous flow mode, the trigger depressed until a continuous stream of fluid is ejected.

Once loaded and optimally primed, the apparatus may be used to inject fluid. For example, as shown in FIG. 34, the device may be placed in the injection mode (or configured that it is in the injection mode) 3401. Further, the type of injection, such as continuous or preset volume, may be selected, e.g., by the user adjusting a fluid volume control to select from one or more predefined volumes (e.g., 1 cc, 2 cc, 3 cc, 4 cc, 5 cc, 6 cc, 7 cc, 8 cc, 9 cc, 10 cc, etc.) and/or a continuous injection mode ("freestyle") 3403.

The needle may then be inserted into the region to be injected (e.g., in some examples, a patient tissue) 3405. In some cases the user may wish to confirm that, e.g., when injecting into a body, that the region of the body in which the needle is inserted is not in a blood vessel (or other region) by aspirating from the body out of the device. The selector of the apparatus may be set to an aspirate mode so that the needle (through the delivery port) is fluidly connected to the fill port (or in some examples, a separate aspiration port); a syringe may be attached to the fill/aspiration port and may be used to withdraw fluid from the body 3407. Once confirmed, the selector may be set to the inject mode and the user may apply pressure to the trigger control of the device to expel fluid from the apparatus 3409. During operation, the apparatus may confirm that the pressure within the apparatus (e.g., within the manifold in variations including a manifold) is within a safe range. Negative pressure within the apparatus may indicate that the reservoir is empty. If the pressure exceeds a pressure threshold, the apparatus may enter a fault mode, e.g., disabling the drive or drive subsystem.

When a predetermined volume injection has been selected, triggering the device may deliver the predetermined volume 3411. Alternatively a continuous mode may allow the user to inject fluid continuously. In some examples, the user may adjust the rate of injection (of the fluid being injected) by increase or decreasing the pressure on trigger control. The user may repeatedly remove and re-insert the needle into different sites to be injected 3413. The apparatus may be re-filled, either before or after the apparatus has indicated that the reservoir is empty, by coupling a source of filling material (e.g., drug) to the fill port and placing the apparatus in the fill configuration (e.g., by changing the selector setting) 3415. The steps for filing and/or priming described in FIG. 33 may be repeated.

Once the injections are complete, the apparatus may be prepared for disposal and/or reuse or partial re-use. For example, the needle may be removed 3501. The device may be de-powered 3503 (either before or after removing the needle). In examples in which the apparatus includes multiple portions (such as a fluid-handling portion and a handle portion), the handle portion may be separated from the fluid-handling portion 3505 and, if desired, reused, while the fluid-handling portion may be disposed of (as medical waste). If the handle portion is to be reused, it may be recharged, or the batteries replaced. If the handle portion is to be disposed of, the components (e.g. battery, circuitry, motor, etc.) may be removed and recycled.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

What is claimed is:

1. A method, the method comprising:
   assembling a fluid-handing portion of an injection system with a handle portion of the injection system by coupling the fluid-handling portion to the handle portion so that a motor in the handle portion engages a drive assembly in the fluid-handling portion;
   filling a reservoir within the fluid-handling portion with a fluid while a manifold within the fluid-handling portion is in a fill configuration with the reservoir in fluid communication with a fill port on the fluid-handling portion;
   selecting a control to an aspiration position and aspirating, so that fluid is drawn from the patient to an aspiration window to detect blood;

setting the control to an injection position so that the manifold is in an injection configuration in which a delivery port of the fluid-handing portion is in fluid communication with a first piston chamber, a second piston chamber and the reservoir through a plurality of check valves; and
   ejecting fluid from the delivery port by reciprocally driving a first piston in the first piston chamber and a second piston in the second piston chamber to alternately transfer fluid from the reservoir and into the first piston chamber and the second piston chamber, and to alternately drive fluid from the second piston chamber and the first piston chamber out of the delivery port in a continuous flow.

2. The method of claim 1, wherein assembling the fluid-handling portion turns on power to the injection system.

3. The method of claim 1, further comprising attaching an injection needle to the delivery port.

4. The method of claim 1, further comprising setting a selector to a fill position prior to filling the reservoir.

5. The method of claim 1, further comprising priming the injection system.

6. The method of claim 1, further comprising closing the delivery port before filling the reservoir.

7. The method of claim 1, further comprising setting a fluid volume control to a pre-set volume mode or to a continuous delivery mode prior to ejecting fluid from the delivery port.

8. The method of claim 1, wherein ejecting fluid from the delivery port comprises ejecting fluid to a predefined volume when a fluid volume control is set to a predefined volume mode.

9. The method of claim 8, wherein ejecting fluid to the predefined volume comprises encoding movement of the drive assembly and comparing the encoded movement to a predefined value.

10. The method of claim 1, wherein ejecting fluid from the delivery port comprises adjusting a rate of movement of the drive assembly based on force applied to a trigger control.

11. The method of claim 1, wherein ejecting fluid from the delivery port comprises continuously ejecting fluid from the delivery port while a trigger control is activated by a user.

12. The method of claim 1, wherein ejecting fluid from the delivery port comprises reciprocating the motor so that the motor is driven alternately clockwise and counterclockwise.

13. The method of claim 1, further wherein in the aspiration configuration the delivery port is in fluid communication with the fill port and the reservoir, and the first piston chamber and the second piston chamber are not in fluid communication with the delivery port.

14. A method, the method comprising:
   filling a reservoir within a hand-held injection system with a fluid while the hand-held injection system is set to a fill position so that a manifold within the hand-held injection system is in a fill configuration with the reservoir in fluid communication with a fill port on the hand-held injection system through the manifold;
   setting the hand-held injection system to aspirate and aspirating a patient with the hand-held injection system, so that fluid is drawn from the patient to an aspiration window to allow detection of blood when aspirating; and
   setting the hand-held injection system to inject so that the manifold is in an injection configuration in which a delivery port of the hand-held injection system is in fluid communication with a first piston chamber, a second piston chamber and the reservoir through a plurality of check valves; and ejecting fluid from the delivery port when a trigger control on a handle of the hand-held injection system is activated so that a drive assembly reciprocally drives a first piston in the first piston chamber and a second piston in the second piston chamber to alternately transfer fluid from the reservoir and into the first piston chamber and the second piston chamber, and to alternately drive fluid from the second piston chamber and the first piston chamber out of the delivery port in a continuous flow.

15. The method of claim 14, further comprising priming the hand-held injection system.

16. The method of claim 14, further comprising closing the delivery port before filling the reservoir.

17. The method of claim 14, further comprising setting a fluid volume control on the hand-held injection system to a pre-set volume mode or to a continuous delivery mode prior to ejecting fluid from the delivery port.

18. The method of claim 14, wherein ejecting fluid from the delivery port comprises ejecting fluid to a predefined volume when a fluid volume control is set to a predefined volume mode.

19. The method of claim 14, wherein ejecting fluid to the predefined volume comprises encoding movement of the drive assembly and comparing the encoded movement to a predefined value in a controller of the hand-held injection system.

20. The method of claim 14, wherein ejecting fluid from the delivery port comprises adjusting a rate of movement of the drive assembly based on force applied to the trigger control.

\* \* \* \* \*